US010716859B2

(12) United States Patent
Drew et al.

(10) Patent No.: US 10,716,859 B2
(45) Date of Patent: *Jul. 21, 2020

(54) EXCIPIENTS FOR STABILISING VIRAL PARTICLES, POLYPEPTIDES OR BIOLOGICAL MATERIAL

(71) Applicant: Stabilitech Biopharma Ltd, West Sussex (GB)

(72) Inventors: Jeffrey Drew, London (GB); David Thomas Woodward, London (GB); John Bainbridge, London (GB); Amanda Corteyn, London (GB)

(73) Assignee: Stabilitech Biopharma Ltd, West Sussex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/147,114

(22) Filed: May 5, 2016

(65) Prior Publication Data
US 2016/0317665 A1 Nov. 3, 2016

Related U.S. Application Data

(63) Continuation of application No. 13/637,913, filed as application No. PCT/GB2011/000493 on Mar. 31, 2011, now abandoned.

(30) Foreign Application Priority Data

Mar. 31, 2010 (GB) .................................. 1005517.6
Mar. 31, 2010 (GB) .................................. 1005521.8
Oct. 19, 2010 (GB) .................................. 1017648.5

(51) Int. Cl.
*A61K 47/20* (2006.01)
*A61K 39/145* (2006.01)
*C12N 7/00* (2006.01)
*A61K 47/18* (2017.01)
*A61K 47/26* (2006.01)
*A61K 47/34* (2017.01)
*A61K 9/00* (2006.01)
*C07K 16/24* (2006.01)
*A61K 39/12* (2006.01)
*A61K 41/10* (2020.01)
*A61J 1/06* (2006.01)
*A61J 1/10* (2006.01)
*A61K 9/08* (2006.01)
*A61K 39/235* (2006.01)
*A61K 39/285* (2006.01)
*A61K 39/00* (2006.01)

(52) U.S. Cl.
CPC .............. *A61K 47/20* (2013.01); *A61J 1/06* (2013.01); *A61J 1/10* (2013.01); *A61K 9/0019* (2013.01); *A61K 9/08* (2013.01); *A61K 39/12* (2013.01); *A61K 39/145* (2013.01); *A61K 39/235* (2013.01); *A61K 39/285* (2013.01); *A61K 41/10* (2020.01); *A61K 47/183* (2013.01); *A61K 47/186* (2013.01); *A61K 47/26* (2013.01); *A61K 47/34* (2013.01); *C07K 16/241* (2013.01); *C12N 7/00* (2013.01); *A61K 2039/525* (2013.01); *A61K 2039/5254* (2013.01); *C07K 2317/55* (2013.01); *C07K 2317/76* (2013.01); *C12N 2710/10334* (2013.01); *C12N 2710/10351* (2013.01); *C12N 2710/24134* (2013.01); *C12N 2710/24151* (2013.01); *C12N 2760/16134* (2013.01); *C12N 2760/16151* (2013.01)

(58) Field of Classification Search
None
See application file for complete search history.

(56) References Cited

U.S. PATENT DOCUMENTS

| 3,927,208 A | 12/1975 | Zygraich et al. |
| 4,631,189 A | 12/1986 | Kendall et al. |
| 4,639,339 A | 1/1987 | Murashige et al. |
| 4,808,700 A | 2/1989 | Anderson et al. |
| 4,816,568 A | 3/1989 | Hamilton, Jr. et al. |
| 4,950,596 A | 8/1990 | Cheng et al. |
| 5,109,026 A | 4/1992 | Hoskinson et al. |
| 5,169,758 A | 12/1992 | Fischer et al. |
| 5,240,843 A | 8/1993 | Gibson et al. |
| 5,580,856 A | 12/1996 | Prestrelski et al. |
| 5,618,539 A | 4/1997 | Dorval et al. |

(Continued)

FOREIGN PATENT DOCUMENTS

| CA | 2083407 A1 | 5/1993 |
| CN | 101670104 A | 3/2010 |

(Continued)

OTHER PUBLICATIONS

Breteler, Paul; "The MSM miracle" available online at http://www.msm-info.com/, available online Jul. 2001.*
Mateu, Mauricio, "Assembly, stability and dynamics of virus capsids." Arch. Biochem. Biophys. (2013) 531 p. 65-79.*
Izutsu, Ken-ichi, "Stabilization of therapeutic proteins by chemical and physical methods." Thereapeutic proteins, Smales and James, ed. ISBN 1-58829-390-4, p. 287-292.*
Izutsu, Ken-ichi; "Stabilization of therapeutic proteins by chemical and physical methods." in Therapeutic Proteins (2005), Smales C. Mark and James, David C, ed, ISBN 1-58829-390-4, p. 287-292.*

(Continued)

Primary Examiner — Fred H Reynolds
(74) Attorney, Agent, or Firm — Clark & Elbing LLP; Susan M. Michaud

(57) ABSTRACT

A sterile pharmaceutically acceptable aqueous solution, which solution is provided in a sealed container and comprises:
a pharmaceutically acceptable aqueous solvent;
viral particles or a physiologically active polypeptide;
an excipient selected from a polyethyleneimine; a compound of formula (I) or a physiologically acceptable salt or ester thereof; or a compound of formula (II) or a physiologically acceptable salt or ester thereof; and
optionally, one or more sugars.

17 Claims, 37 Drawing Sheets

(56) References Cited

U.S. PATENT DOCUMENTS

| | | | |
|---|---|---|---|
| 5,691,163 A | 11/1997 | Cameron et al. | |
| 6,037,116 A | 3/2000 | Wiggins et al. | |
| 6,127,181 A | 10/2000 | Kadkade | |
| 6,194,136 B1 | 2/2001 | Livesey et al. | |
| 6,248,588 B1 | 6/2001 | Crespo et al. | |
| 6,689,600 B1 | 2/2004 | Wu et al. | |
| 7,235,391 B2 | 6/2007 | Wu et al. | |
| 9,101,607 B2 | 8/2015 | Drew et al. | |
| 10,029,007 B2 | 7/2018 | Drew et al. | |
| 10,086,064 B2 | 10/2018 | Drew | |
| 10,206,960 B2* | 2/2019 | Drew | C12N 7/00 |
| 2004/0110267 A1 | 6/2004 | Sundar | |
| 2004/0253574 A1 | 12/2004 | Schuler et al. | |
| 2005/0048058 A1 | 3/2005 | Yamazaki et al. | |
| 2005/0239705 A1 | 10/2005 | Dake et al. | |
| 2006/0073182 A1 | 4/2006 | Wong et al. | |
| 2006/0154858 A1 | 7/2006 | Mattson et al. | |
| 2006/0228334 A1 | 10/2006 | Rosa-Calatrava et al. | |
| 2006/0247167 A1 | 11/2006 | Schlein et al. | |
| 2007/0253941 A1 | 11/2007 | Naidu et al. | |
| 2008/0107631 A1 | 5/2008 | Wu et al. | |
| 2008/0299168 A1 | 12/2008 | Dadey et al. | |
| 2009/0123436 A1 | 5/2009 | Opperman | |
| 2010/0029569 A1 | 2/2010 | Bjorn et al. | |
| 2010/0260796 A1 | 10/2010 | Belin-Poput et al. | |
| 2011/0081363 A1 | 4/2011 | Whitney et al. | |
| 2013/0071431 A1 | 3/2013 | Drew et al. | |
| 2013/0129685 A1* | 5/2013 | Drew | A61K 35/76 424/93.6 |
| 2013/0156797 A1 | 6/2013 | Drew et al. | |
| 2013/0164296 A1 | 6/2013 | Drew et al. | |
| 2014/0294757 A1 | 10/2014 | Drew et al. | |
| 2016/0317665 A1 | 11/2016 | Drew et al. | |
| 2017/0021008 A1* | 1/2017 | Drew | A61K 9/0019 |
| 2019/0307819 A1* | 10/2019 | Drew | C12N 7/00 |
| 2019/0350846 A1 | 11/2019 | Drew | |

FOREIGN PATENT DOCUMENTS

| | | |
|---|---|---|
| EP | 0130619 A2 | 1/1985 |
| EP | 0156242 A2 | 10/1985 |
| EP | 0312114 A2 | 4/1989 |
| EP | 0376361 A2 | 7/1990 |
| EP | 0890362 A1 | 1/1999 |
| EP | 1946776 A1 | 7/2008 |
| EP | 1961761 A1 | 8/2008 |
| EP | 1133316 B1 | 1/2009 |
| JP | 60-193925 | 10/1985 |
| JP | 61189228 A | 8/1986 |
| JP | 2003095956 A | 4/2003 |
| JP | 2003-261591 A | 9/2003 |
| JP | 2007-524592 A | 8/2007 |
| JP | 2008513438 A | 5/2008 |
| JP | 2009510136 A | 3/2009 |
| JP | 2009526856 A | 7/2009 |
| JP | 2011-516608 A | 5/2011 |
| WO | WO-89/11297 A1 | 11/1989 |
| WO | WO-90/05182 A1 | 5/1990 |
| WO | WO-93/00807 A1 | 1/1993 |
| WO | WO-94/04174 A1 | 3/1994 |
| WO | WO-95/10605 A1 | 4/1995 |
| WO | WO-95/11700 A1 | 5/1995 |
| WO | WO-97/04801 A1 | 2/1997 |
| WO | WO-97/15331 A1 | 5/1997 |
| WO | WO-99/27071 A1 | 6/1999 |
| WO | WO-00/29024 A1 | 5/2000 |
| WO | WO-01/29198 A1 | 4/2001 |
| WO | WO-01/93829 A2 | 12/2001 |
| WO | WO-02/101412 A2 | 12/2002 |
| WO | WO-03/035827 A2 | 5/2003 |
| WO | WO-2004/002534 A1 | 1/2004 |
| WO | WO-2004/007537 A2 | 1/2004 |
| WO | WO-2004/035818 A1 | 4/2004 |
| WO | WO-2004/105790 A1 | 12/2004 |
| WO | WO-2004/108753 A1 | 12/2004 |
| WO | WO-2005/042029 A2 | 5/2005 |
| WO | WO-2005/056808 A2 | 6/2005 |
| WO | WO-2005/062709 A2 | 7/2005 |
| WO | WO-2006/081587 A2 | 8/2006 |
| WO | WO-2006/085082 A1 | 8/2006 |
| WO | WO-2006/092668 A2 | 9/2006 |
| WO | WO-2006/094974 A2 | 9/2006 |
| WO | WO-2006/127150 A2 | 11/2006 |
| WO | WO-2007/035455 A2 | 3/2007 |
| WO | WO-2007/038926 A1 | 4/2007 |
| WO | WO-2007/056847 A1 | 5/2007 |
| WO | WO-2007/095337 A2 | 8/2007 |
| WO | WO-2007/138135 A1 | 12/2007 |
| WO | WO-2007/149287 A2 | 12/2007 |
| WO | WO-2008/051245 A2 | 5/2008 |
| WO | WO-2008/058035 A1 | 5/2008 |
| WO | WO-2008/114021 A1 | 9/2008 |
| WO | WO-2008/118691 A2 | 10/2008 |
| WO | WO-2008/150479 A2 | 12/2008 |
| WO | WO-2009/006097 A1 | 1/2009 |
| WO | WO-2009/015343 A2 | 1/2009 |
| WO | WO-2009/129101 A1 | 10/2009 |
| WO | WO-2010/035001 A1 | 4/2010 |
| WO | WO-2010/146598 A2 | 12/2010 |
| WO | WO-2011/109415 A2 | 9/2011 |
| WO | WO-2011/121301 A1 | 10/2011 |
| WO | WO-2011/121305 A2 | 10/2011 |
| WO | WO-2011/121306 A1 | 10/2011 |
| WO | WO-2013/050780 A1 | 4/2013 |
| WO | WO-2018/206930 A1 | 11/2018 |

OTHER PUBLICATIONS

"Composition of Medium 199," XP002596423 (2009). Retrieved from the Internet: <URL:http://www.fishersci.com/wps/downloads/segment/Scientific/pdf/cmbrex_medium_199.pdf>.

"Renaturation (Molecular Biology)," <http://what-when-how.com/molecular-biology/renaturation-molecular-biology/>, retrieved on Oct. 15, 2015 (2 pages).

Andersson et al., "Protein stabilising effect of polyethyleneimine" J Biotech. 72(1-2):21-31 (1999).

Andersson et al., "Stabilizing effect of chemical additives against oxidation of lactate dehydrogenase," Biotechnol Appl Biochem. 32:145-53 (2000).

Arakawa et al., "Factors affecting short-term and long-term stabilities of proteins ," Adv Drug Deliv Rev. 10:1-28 (1993).

Arakawa et al., "Factors affecting short-term and long-term stabilities of proteins," Adv Drug Deliv Rev. 46(1-3):307-26 (2001).

Berge et al., "Preservation of enteroviruses by freeze-drying," Appl Microbiol. 22(5):850-3 (1971).

Braun et al., "Development of a freeze-stable formulation for vaccines containing aluminum salt adjuvants," Vaccine. 27(1):72-9 (2009).

Brown et al., "Assembly of hybrid bacteriophage Qbeta virus-like particles," Biochemistry. 48(47):11155-7 (2009).

Bryjak et al., "Storage stabilization and purification of enzyme by water-soluble synthetic polymers," Enzyme Microb Technol. 16:616-21 (1994).

Bryjak, "Storage stabilization of enzyme activity by poly(ethyleneimine)," Bioprocess Eng. 13:177-81 (1995).

Carpenter et al., "The mechanism of cryoprotection of proteins by solutes," Cryobiology. 25(3):244-55 (1988).

Chen et al., "Stabilization of recombinant human keratinocyte growth factor by osmolytes and salts," J Pharm Sci. 85(4):419-22 (1996).

Cleland et al., "Glycine betaine as a cryoprotectant for prokaryotes," J Microbiol Methods. 58(1):31-8 (2004).

Cosquer et al., "Nanomolar levels of dimethylsulfoniopropionate, dimethylsulfonioacetate, and glycine betaine are sufficient to confer osmoprotection to *Escherichia coli*," Appl Environ Microbiol. 65(8):3304-11 (1999).

Costantino et al., "Effect of excipients on the stability and structure of lyophilized recombinant human growth hormone," J Pharma Sci. 87(11):1412-20 (1998).

(56) References Cited

OTHER PUBLICATIONS

Drew et al., "Stable vaccine technology," displayed in Vienna Oct. 3-5, 2010.
Foreman et al., "Effects of charged water-soluble polymers on the stability and activity of yeast alcohol dehydrogenase and subtilisin Carlsberg," Biotechnol Bioeng. 76(3):241-6 (2001).
Greiff et al., "Effects of freezing, storage at low temperatures, and drying by sublimation in vacuo on the activities of measles virus," Nature. 202:624-5 (1964).
Gupta et al., "Stabilization of respiratory syncytial virus (RSV) against thermal inactivation and freeze-thaw cycles for development and control of RSV vaccines and immune globulin," Vaccine. 14(15):1417-20 (1996).
Holtmann et al., "Thermoprotection of Bacillus subtilis by exogenously provided glycine betaine and structurally related compatible solutes: involvement of Opu transporters," J Bacteriol. 186(6):1683-93 (2004).
Hubálek, "Protectants used in the cryopreservation of microorganisms," Cryobiology. 46(3):205-29 (2003).
Izutsu, "Stabilization of therapeutic proteins by chemical and physical methods" in *Therapeutic Proteins, Smales and James* ed. Humana Press ISBN 1-58829-390-4, 287-292 (2005).
Land et al., "The Challenges of Antimicrobial Preservation of a Sugar-free Liquid Risedronate Sodium Formulation for US and EMEA Pediatric Use," Post No. M1187. Procter & Gamble Pharmaceuticals, 2009 AAPS Natual Meeting and Exposition, Los Angeles, CA (2009).
Larski et al., "Stabilization of Newcastle disease virus by dimethyl sulfoxide," Acta Virol. 16(4):349-52 (1972).
Lever et al., "Using high-performance liquid chromatography to measure the effects of protein-stabilizing cosolvents on a model protein and fluorescent probes," Anal Biochem. 367(1):122-33 (2007).
Liao et al., "Influence of the active pharmaceutical ingredient concentration on the physical state of mannitol—implications in freeze-drying," Pharm Res. 22(11):1978-85 (2005). Abstract provided.
Liao et al., "Protective mechanism of stabilizing excipients against dehydration in the freeze-drying of proteins," Pharm Res. 19(12):1854-61(2002).
Manual of Policies and Procedures, Center for Drug Evaluation and Research, "Applications for Parenteral Products in Plastic Immediate Containers," MAPP 6020.2 (2007).
McGann et al., "Cryoprotection by dimethyl sulfoxide and dimethyl sulfone," Cryobiology. 24(1):11-6 (1987).
Nishigushi et al., "Temperature- and concentration-dependence of compatibility of the organic osmolyte beta-dimethylsulfoniopropionate," Cryobiology. 29(1):118-24 (1992).
Paleg et al., "Proline and glycine betaine influence protein solvation," Plant Physiol. 75(4):974-8 (1984).
Peek et al., "A rapid, three-step process for the preformulation of a recombinant ricin toxin A-chain vaccine," J Pharm Sci. 96(1):44-60 (2007).
Rathore et al. "Current perspectives on stability of protein drug products during formulation, fill and finish operations." Biotechnol Prog. 24(3):504-14 (2008).
Reichert et al., "Development trends for monoclonal antibody cancer therapeutics," Nat Rev Drug Discov. 6(5):349-56 (2007).
Sigalov, "Cryopreservation and long-term storage of human low density lipoproteins," Eur J Clin Chem Clin Biochem. 33(2):73-81 (1995).
Singh et al., "The osmoprotectants glycine and its methyl derivatives prevent the thermal inactivation of protective antigen of Bacillus anthracis," Biochem Biophys Res Comm. 316(2):559-64 (2004).
Sjölander et al., "ISCOMs: an adjuvant with multiple functions," J Leukoc Biol. 64(6):713-23 (1998).
Suntanto, et al. "Home delivery of heat stable vaccines in Indonesia: outreach immunization with a prefilled single use injection device" Bull. World. Health. Organ. 77(2):119-126 (1999).
The class notes from Indiana University on viral structure, http://courses.bio.indiana.edu/M430-Taylor/structure.html, available online Jun. 2007.
Tiyaboonchai et al., "Insulin containing polyethylenimine-dextran sulfate nanoparticles," Int J Pharm. 255(1-2):139-51 (2003).
Wallis et al., "Stabilization of enveloped viruses by dimethyl sulfoxide," J Virol. 2(9):953-4 (1968).
Wolff et al., "Protection of aluminum hydroxide during lyophilisation as an adjuvant for freeze-dried vaccines," Colloids and Surfaces A: Physicochem. Eng Aspects. 330:116-26 (2008).
Wolff et al., "Comparative stability study of lyophilised aluminium hydroxide aduvanted vaccine formulations containing a monoclonal antibody as a model antigen and methods used for their characterisation," Colloids and Surfaces A: Physicochem. Eng Aspects. 339:82-93 (2009).
Wolff et al.,"Development of a formulation protecting aluminum hydroxide adjuvant vaccines during lyophilisation," 6th World Meeting on Pharmaceutics, Biopharmaceutics and Pharmaceutical Technology, Barcelona, Apr. 7-10, 2008.
Yancey, "Organic osmolytes as compatible, metabolic and counteracting cytoprotectants in high osmolarity and other stresses," J Exp Biol. 208:2819-30 (2005).
Michaelis et al., "Dimethylglycine buffer," J Biol Chem. 115:221-2 (1936).
Santoro et al., "Increased thermal stability of proteins in the presence of naturally occurring osmolytes," Biochemistry. 31(23):5278-83 (1992).
Schiefner et al., "Structural basis for the binding of compatible solutes by ProX from the hyperthermophilic archaeon Archaeoglobus fulgidus," J Biol Chem. 279(46):48270-81 (2004).
U.S. Appl. No. 13/637,828, Drew et al.
U.S. Appl. No. 13/637,913, Drew et al.
U.S. Appl. No. 14/349,481, Drew et al.
Burke et al., "Formulation, stability, and delivery of live attenuated vaccines for human use," Crit Rev Ther Drug Carrier Syst. 16(1):1-83 (1999).
Chang et al., "Mechanisms of protein stabilization in the solid state," J Pharm Sci. 98(9):2886-908 (2009).
Communication pursuant to Article 94(3) EPC for European Application No. 12772389.8, dated Oct. 21, 2015 (7 pages).
Davidson et al. "Effect of sucrose/raffinose mass ratios on the stability of co-lyophilized protein during storage above the Tg" Pharm Res. 18(4):474-9 (2001).
Izutsu et al., "Stabilization of protein structure in freeze-dried amorphous organic acid buffer salts," Chem Pharm Bull (Tokyo). 57(11):1231-6 (2009).
Kim et al., "Counteracting effects of renal solutes on amyloid fibril formation by immunoglobulin light chains," J Biol Chem. 276(2):1626-33 (2001).
Lloyd, et al. "A comparison of glycine, sarcosine, N,N-dimethylglycine, glycinebetaine and N-modified betaines as liposome cryoprotectants" J Pharm Pharmacol. 44(6):507-11 (1992).
Maltesen et al., "Drying methods for protein pharmaceuticals," Drug Disc Today Technol. 5(2-3):e81-8 (2008).
Pikal et al., "The effects of formulation variables on the stability of freeze-dried human growth hormone," Pharm Res. 8(4):427-36 (1991).
Popova et al., "Cryoprotective effect of glycine betaine and glycerol is not based on a single mechanism," Cryo Letters. 22(5):293-8 (2001).
Roy et al., "Freeze-drying of proteins: some emerging concerns," Biotechnol Appl Biochem. 39(Pt 2):165-77 (2004).
Stabilitech: "Stabilitech Technology," Innovations in Health. XP002635295. Nov. 19, 2009 (21 pages).
Tang et al., "Measurement of the kinetics of protein unfolding in viscous systems and implications for protein stability in freeze-drying," Pharm Res. 22(7):1176-85 (2005).
Tang et al., "The effect of stabilizers and denaturants on the cold denaturation temperatures of proteins and implications for freeze-drying," Pharm Res. 22(7):1167-75 (2005).
Tesconi et al., "Freeze-drying above room temperature," J Pharm Sci. 88(5):501-6 (1999).

(56) References Cited

OTHER PUBLICATIONS

Vasudevamurthy, et al. "Enzyme stabilization using synthetic compensatory solutes" Biocat and Biotransform. 23(3/4):285-291 (2005).
Ishimaru et al., "Pressure-inactivated FMDV: a potential vaccine," Vaccine. 22(17-18):2334-9 (2004).
Abdul-Fattah et al., "Drying-induced variations in physicochemical properties of amorphous pharmaceuticals and their impact on Stability II: stability of a vaccine," Pharm Res. 24(4):715-27 (2007).
Abdul-Fattah et al., "The effect of annealing on the stability of amorphous solids: chemical stability of freeze-dried moxalactam," J Pharm Sci. 96(5):1237-50 (2007).
Publication by Lymphomation.org, <http://www.lymphomation.org/side-effect-HAMA.htm>, accessed Dec. 2, 2017 (2 pages).
Suzuki et al., "Mammalian lactoferrin receptors: structure and function," Cell Mol Life Sci. 62(22):2560-75 (2005).
International Search Report and Written Opinion for PCT/GB2015/051072, dated Jul. 10, 2015 (10 pages).
Reap et al., "Stimulation of the immune response by dimethylglycine, a nontoxic metabolite," J Lab Clin Med. 115(4):481-6 (1990).
Search Report for UK Application No. GB1406569.2, dated Nov. 27, 2014 (2 pages).
Stabilitech: "Innovations in Health," dated Nov. 19, 2009 (21 pages).

\* cited by examiner

FIG. 3

Influenza HA liquid stability

EXCIPIENTS FOR STABILISING VIRAL PARTICLES, POLYPEPTIDES OR BIOLOGICAL MATERIAL

FIELD OF THE INVENTION

The present invention is concerned with storage-stable formulations of viruses and polypeptides.

BACKGROUND TO THE INVENTION

Some biological molecules are sufficiently stable that they can be isolated, purified and then stored in solution at room temperature. However, this is not possible for many materials and techniques involving storage at low temperature, addition of stabilisers, freeze-drying, vacuum formation and air-drying have been tried to ensure shelf preservation. Despite the availability of these techniques, some biological materials still show unsatisfactory levels of stability during storage and some techniques lead to added cost and inconvenience. For example, refrigerated transportation and storage is expensive. Further, refrigerated transport is often not available for the transport of medicines such as vaccines in countries in the developing world.

In particular, the stresses of freeze-drying or lyophilisation can be very damaging to some biological materials. Freeze drying of biopharmaceuticals involves freezing solutions or suspensions of thermosensitive biomaterials, followed by primary and secondary drying. The technique is based on sublimation of water at subzero temperature under vacuum without the solution melting. Freeze-drying represents a key step for manufacturing solid protein and vaccine pharmaceuticals. The rate of water vapour diffusion from the frozen biomaterial is very low and therefore the process is time-consuming. Additionally, both the freezing and drying stages introduce stresses that are capable of unfolding or denaturing proteins.

Proteins are molecules with defined primary, secondary, tertiary and in some instances quaternary structures. The structure plays an important role in giving a protein its specific biological function. Unfortunately, the structural complexity of biological pharmaceuticals such as proteins makes them susceptible to various processes that result in structural and functional instability. Conformational integrity and functional groups must be protected from degradation Instability can be a consequence of a variety of covalent and non-covalent reactions or modifications in solution. Degradation is generally classified into two main categories: firstly physical degradation or non-covalent pathway degradation and secondly the covalent degradation pathway.

Proteins can degrade via physical processes such as interfacial adsorption and aggregation which can significantly reduce a protein drug's potency and stability. A second consequence is that unfolding mediated by adsorption at an interface can often be an initiating step for irreversible aggregation of the protein in solution. Exposure of the protein's core at a hydrophobic surface can result in adsorption as a consequence of agitation, temperature or pH induced stresses; all of which can lead to aggregation.

Proteins may be subject to chemical modification such as oxidation, isomerisation, hydrolysis, disulfide scrambling, beta elimination, deamidation, and adduct formation. The principal hydrolytic mechanisms of degradation include peptide bond hydrolysis, deamidation of asparagine and glutamine and the isomerisation of aspartic acid. A common feature of the hydrolytic degradation pathway is that one significant formulation variable, with respect of the rates of the reactions is the pH.

As protein stability can significantly affect the safety and efficacy of a therapeutic, the composition of components in a biopharmaceutical formulation can affect the extent of protein degradation. The method of formulation of a biopharmaceutical also can impact the ease and frequency of administration.

Due to problems with instability and aggregation, most current stable formulations of proteins are not liquid formulations. Typically proteins are freeze dried (lyophilised) to provide stable formulations of the proteins. A bulking agent is often present in the formulations. The freeze dried formulations are distributed and stored in dried form, typically as a powder, in a sealed vial, ampoule or syringe. For example, WO 97/04801 describes stable lyophilised formulations of anti-IgE antibodies which have to be reconstituted immediately prior to use.

WO-A-2006/0850082 reports a desiccated or preserved product comprising a sugar, a charged material such as a histone protein and a dessication- or thermo-sensitive biological component. The sugar forms an amorphous solid matrix. However, the histone may have immunological consequences if the preserved biological component is administered to a human or animal.

WO 2008/114021 describes a method for preserving viral particles. The method comprises drying an aqueous solution of one or more sugars, a polyethyleneimine and the viral particles to form an amorphous solid matrix comprising the viral particles. The aqueous solution contains the polyethyleneimine at a concentration of 15 μM or less based on the number-average molar mass ($M_n$) of the polyethyleneimine and the sugar concentration or, if more than one sugar is present, total sugar concentration is greater than 0.1M.

WO 2010/035001 describes a method for preserving a polypeptide in which an aqueous solution of the polypeptide is dried, for example freeze dried, in the presence of one or more sugars and a polyethyleneimine (PEI). The resulting dried composition is typically provided as a stable dry powder in a sealed vial, ampoule or syringe. A solution is reconstituted from the powder in order to administer the polypeptide to a patient e.g. by injection.

Drying and especially freeze drying are however costly and time-consuming processes. It would be advantageous if their use could be avoided. Biologically active materials often suffer a loss of activity following heating and drying. Additionally, the need to reconstitute a freeze dried powder in a solvent before use of the polypeptide is an inconvenience. Indeed, it can carry risks for the patient or medical professional who performs the reconstitution step if the procedure is not carried out correctly.

It is thus advantageous to provide liquid virus and protein formulations that do not require reconstitution in order to be used. Consequently, there is a demand for stable liquid injectable virus and protein formulations. There is a demand for highly concentrated stable liquid injectable antibody formulations.

SUMMARY OF THE INVENTION

It has now surprisingly been found that storage-stable ready-to-use aqueous solutions of viral particles or polypeptides can be provided by use of certain excipients and optionally one, two or more sugars. These formulations retain long term stability. They can be prepared without a drying or freeze drying step. They circumvent the need to reconstitute a solution from a freeze dried powder prior to use. It has also been found that these excipients and optionally one, two or more sugars can preserve viral particles or polypeptides during manufacture. Further, it has been found that these excipients and optionally one, two or more sugars can preserve samples taken from a human or animal.

Accordingly, the present invention provides a sterile pharmaceutically acceptable aqueous solution, typically suitable for parenteral administration, which solution is provided in a sealed container and comprises:
- a pharmaceutically acceptable aqueous solvent;
- viral particles or a physiologically active polypeptide;
- an excipient selected from a polyethyleneimine; a compound of formula (I) or a physiologically acceptable salt or ester thereof

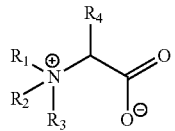
(I)

wherein:
$R_1$ represents hydrogen or $C_{1-6}$ alkyl; and
$R_4$ represents hydrogen; or
$R_1$ and $R_4$ together with the atoms to which they are attached form a pyrrolidine ring;
$R_2$ represents hydrogen, $C_{1-6}$ alkyl or $-(CH_2)_{2-5}NHC(O)(CH_2)_{5-15}CH_3$; and
$R_3$ represents $C_{1-6}$ alkyl; or
a compound of formula (II) or a physiologically acceptable salt or ester thereof

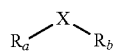
(II)

wherein:
X represents $-S(O)_2-$ or $-S^+(R_c)-$,
$R_a$ and $R_b$ independently represent $C_{1-6}$ alkyl; and
$R_c$ represents $C_{1-6}$ alkyl substituted with a carboxylate anion and with an amine ($-NH_2$) moiety; and
optionally, one or more sugars.

The present invention also provides a sterile pharmaceutically acceptable aqueous solution, which solution comprises:
- a pharmaceutically acceptable aqueous solvent;
- viral particles as defined in any one of claims 1, 3 or 4;
- an N—($C_{1-6}$ alkyl)-, N,N-di($C_{1-6}$ alkyl)- or N,N,N-tri($C_{1-6}$ alkyl)-glycine or a physiologically acceptable salt or ester thereof; and
- a sulfone compound of formula (IIC):

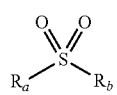
(IIC)

wherein $R_a$ and $R_b$ independently represent $C_{1-6}$ alkyl; and
optionally, one or more sugars.

The invention further provides:
a process for the preparation of a sterile pharmaceutically acceptable solution according to the invention, which process comprises:
(a) providing a sterile solution of the viral particles, excipient and, optionally, one or more sugars in a pharmaceutically acceptable aqueous solution;
(b) sealing the solution in a container;
a further process for the preparation of a sterile pharmaceutically acceptable solution according to the invention, which process comprises:
(a) sealing a solution of the viral particles, excipient and, optionally, one or more sugars in a pharmaceutically acceptable aqueous solvent in a container; and
(b) sterilising the solution in the container;
a ready-to-use, storage-stable aqueous solution which is provided in a sealed container and comprises:
an aqueous solvent;
viral particles or a physiologically active polypeptide;
an excipient of the invention; and
optionally, one or more sugars;
a process for the preparation of a ready-to-use, storage-stable aqueous solution of the invention, which process comprises:
(a) providing a solution of the viral particles or polypeptide, excipient and, optionally, one or more sugars in an aqueous solvent;
(b) sealing the solution in a container;
a further process for the preparation of a ready-to-use, storage-stable aqueous solution of the invention, which process comprises:
(a) sealing a solution of the viral particles or polypeptide, excipient and, optionally, one or more sugars in an aqueous solvent in a container; and
(b) sterilising the solution in the container;
a sealed container in which is provided a ready-to-use, storage-stable aqueous solution which comprises:
an aqueous solvent;
viral particles;
an N—($C_{1-6}$ alkyl)-, N,N-di($C_{1-6}$ alkyl)- or N,N,N-tri($C_{1-6}$ alkyl)-glycine or a physiologically acceptable salt or ester thereof;
a sulfone compound of the invention; and
optionally, one or more sugars; and
a process for producing a sealed container, which process comprises providing a solution of viral particles; an N—($C_{1-6}$ alkyl)-, N,N-di($C_{1-6}$ alkyl)- or N,N,N-tri($C_{1-6}$ alkyl)-glycine or a physiologically acceptable salt or ester thereof; a sulfone compound of formula (IIC) of the invention; and optionally, one or more sugars; in a pharmaceutically acceptable aqueous solvent; and sealing the solution in a container.

The invention further provides:
a process for the preparation of a pharmaceutically acceptable aqueous solution of viral particles or polypeptide, which process comprises: (a) providing a solution of the viral particles or physiologically active polypeptide, an excipient of the invention and, optionally, one or more sugars; and (b) removing the excipient;
use of an excipient of the invention and, optionally, one or more sugars to preserve viral particles or a polypeptide during manufacture of a pharmaceutically acceptable aqueous solution of said virus or polypeptide;
a process for preserving a sample taken from a human or animal, said process comprising providing an aqueous solution of (i) said sample, (ii) an excipient of the invention, and (iii) optionally one or more sugars.

a process for obtaining and preserving a sample from a human or animal, said process comprising (a) obtaining the sample from the human or animal, and (b) preparing an aqueous solution of said sample, an excipient of the invention, and optionally one or more sugars;

an aqueous solution which comprises (i) a sample taken from a human or animal, (ii) an excipient of the invention, and (iii) optionally one or more sugars;

use of an excipient of the invention and, optionally, one or more sugars to preserve a sample taken from a human or animal; and use of an excipient of the invention and, optionally, one or more sugars to preserve a solution comprising viral particles, prior to freeze-drying of said solution.

BRIEF DESCRIPTION OF THE FIGURES

FIG. 3 shows the results of an experiment investigating the effect of excipients in stabilising influenza hemagglutinin (HA) in liquid form.

FIG. 31A is a contour plot where a cross marks the predicted optimum. Colouring indicates level of variable. FIG. 31B is a graph highlighting region of model where predicted recovered viral activity is greater than or equal to that input.

FIG. 46A: Condition 1: Untouched FAb (positive control); FIG. 46B: Condition 2: FAb after 130 h at 56° C. in PBS (negative control); FIG. 46C: Condition 3: FAb after 130 h at 56° C. in SR mix; FIG. 46D: Condition 4: FAb after 130 h at 56° C. in SR mix & low (0.1M) DMG; FIG. 46E: Condition 5: FAb after 130 h at 56° C. in SR mix and high (1.0M) DMG; FIG. 46F: Condition 6: FAb after 130 h at 56° C. in SR mix & low (0.1M) TMG; and FIG. 46G: Condition 7: FAb after 130 h at 56° C. in SR mix & high (1.0M) TMG.

DETAILED DESCRIPTION OF THE INVENTION

Summary

Figure 1:
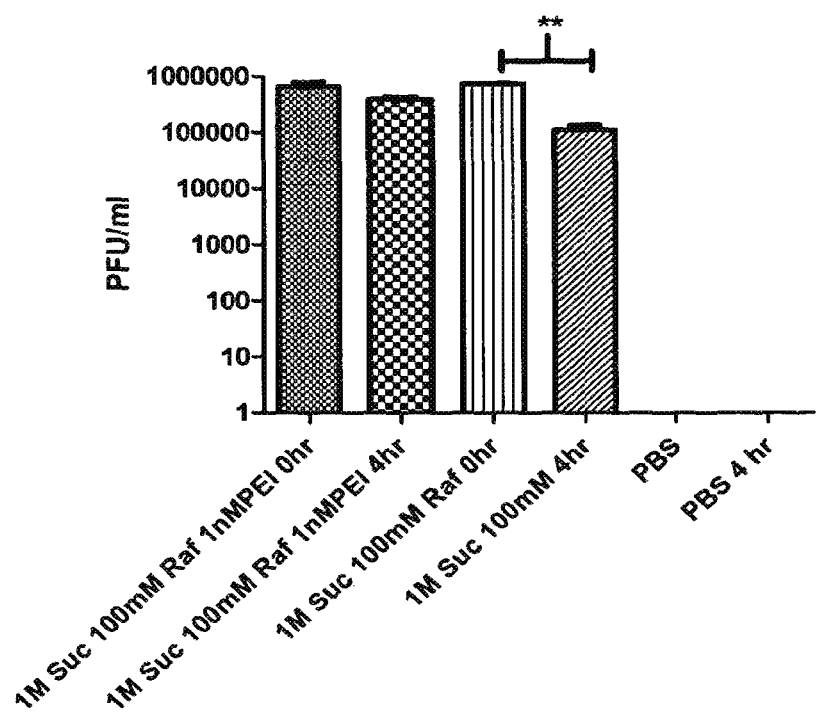
FIG. 1 shows the results of an experiment evaluating whether excipients enhance adenovirus stability in a liquid at room temperature for 4 hours prior to freeze drying. Suc=sucrose. Raf=raffinose. Statistical analysis was carried out using a one-way ANOVA followed by a Bonfferoni post test. P value summary, ** designates $P<0.01$. Error bars show standard error of the mean (n=3).

Stable aqueous solutions of viral particles or polypeptides are provided according to the invention. The solutions are sterile pharmaceutically acceptable liquids that can be administered to a patient without having to be reconstituted from e.g. a dried powder immediately prior to use.

In one embodiment, the present invention relates to the preservation of viral particles by a N-alkylated glycine derivative or a salt or ester thereof, and a sulfone compound of formula (ITC). The N-alkylated glycine derivative and the sulfone compound can interact synergistically to stabilise the viral particles in a liquid setting.

The solutions may take the form of small-volume parenterals of 100 ml or less or large-volume parenterals of 100 ml or more. The solutions are sterile pharmaceutically acceptable liquids that can be administered to a patient without having to be reconstituted from e.g. a dried powder immediately prior to use.

The solutions are capable of exhibiting long term storage stability. They can therefore be stored for 6 to 18 months or longer in a refrigerator, i.e. at temperatures of from 2 to 8° C. In some instances, the solutions can be stored at room temperature for such periods of time. The solutions thus possess sufficient stability to enable them to be manufactured in a factory, distributed e.g. to pharmaceutical wholesalers and pharmacies, and stored prior to use without an unacceptable level of degradation occurring.

Typically, the solutions are provided as clear liquids. The solutions are usually colourless. They may additionally comprise a physiologically acceptable buffer and/or a tonicity adjustment agent and/or a preservative. The solutions may thus be isotonic. The solutions are sealed in an appropriate container in a vial, ampoule, syringe, cartridge, flexible bag or glass bottle. They are thus manufactured in ready-to-use form in a factory. They have not therefore been reconstituted from a solid composition such as a lyophilisate immediately prior to use.

The excipients of the invention can additionally preserve virus particles or polypeptides during manufacture of solutions of said virus particles or polypeptides. Further, the excipients of the invention can preserve solutions of samples taken from a human or animal.

Viral Particles

The viral particles used in the present invention may be whole viruses such as live viruses, killed viruses, live attenuated viruses, inactivated viruses such as chemically inactivated viruses or virulent or non-virulent viruses. A live virus is capable of infecting and replicating within the host cell. A killed virus is inactivated and is unable to replicate within the host cell. The particles may be virus-like particles (VLPs) or nucleocapsids. The virus may be infectious to prokaryotic or eukaryotic cells. The virus may be a human or animal virus.

The viral particle may be, or may be derived from, a dsDNA virus, a ssDNA virus, a dsRNA virus, a (+)ssRNA virus, a (−)ssRNA virus, a ssRNA-RT virus or a dsDNA-RT virus. As an example but not intended to be limiting, the viral particle can be, or can be derived from, a virus of the following families:

Adenoviridae such as human adenovirus A, B, C, D, E or F including human Ad5, Ad2, Ad4, Ad6, Ad24, Ad35, Ad36 serotypes;
Caliciviridae such as the norwalk virus;
Coronaviridae such as human coronavirus 299E or OC43 and SARS-coronavirus;
Filoviridae such as ebola virus;
Flaviviridae such as yellow fever virus, west nile virus, dengue virus, hepatitis C virus;
Hepadnaviridae such as hepatitis B virus;
Herpesviridae such as herpes simplex virus e.g. HSV1 or HSV2, human herpesvirus 1, 3, 4, 5 or 6;
Orthomyxoviridae such as influenzavirus A, B, C including but not limited to influenza A virus serotypes H1N1, H2N2, H3N2, H5N1, H7N7, H1N2, H9H2, H7N2, H7N3 and N10N7;
Papillomaviridae such as human papilloma virus;
Paramyxoviridae such as human parainfluenza virus 1, measles virus and mumps virus;
Parvoviridae such as adeno-associated virus;
Picornaviridae such as human poliovirus, foot and mouth disease virus (including serotypes O, A, C, SAT-1, SAT-2, SAT-3 and Asia-1);
Poxviridae such as vaccinia virus, variola virus and avian poxvirus (fowlpox);
Reoviridae such as bluetongue virus group;
Retroviridae such as lentivirus including human immunodeficiency virus 1 and 2; and
Togaviridae such as rubella virus.

In a preferred embodiment, the viral particle can be or can be derived from an Adenoviridae, Orthomyxoviridae, Paramyxoviridae, Parvoviridae, Picornaviridae or Poxviridae virus. In a particularly preferred embodiment, the viral particle can be or can be derived from an adenovirus, vaccinia virus, influenza virus, or measles virus.

Virus-like particles (VLPs) include viral proteins derived from the structural proteins of a virus, but lack viral nucleic acid. When overexpressed, these viral structural proteins spontaneously self-assemble into particles. VLPs are replication incompetent. In some embodiments, the VLPs are viral proteins embedded within a lipid bilayer. Examples of VLPs includes phage-derived VLPs, human papillomavirus (HPV) L1 major capsid protein VLPs, Norwalk virus capsid protein VLPs and VLPs assembled from influenza virus structural proteins such as M1 protein, HA hemagglutinin protein and N1 neuraminidase protein.

Viral particles can be prepared using standard techniques well known to those skilled in the art. For example, a virus may be prepared by infecting cultured host cells with the virus strain that is to be used, allowing infection to progress such that the virus replicates in the cultured cells and can be released by standard methods known in the art for harvesting and purifying viruses.

Polypeptides

Any polypeptide such as a physiologically active polypeptide is suitable for use in the invention. For example, the polypeptide may be a small peptide of less than 15 amino acids such as 6 to 14 amino acids (e.g. oxytocin, cyclosporin), a larger peptide of between 15 and 50 amino acids (e.g. calcitonin, growth hormone releasing hormone 1-29 (GHRH)), a small protein of between 50 and 250 amino acids in length (e.g. insulin, human growth hormone), a larger protein of greater than 250 amino acids in length or a multisubunit protein comprising a complex of two or more polypeptide chains. The polypeptide may be a peptide hormone, growth factor or cytokine. It may be an antigen-binding polypeptide, receptor inhibitor, ligand mimic or receptor blocking agent. Typically, the polypeptide is in substantially pure form. It may thus be an isolated polypeptide. For example, the polypeptide may be isolated following recombinant production.

For example, the polypeptide may be a hormone selected from a growth hormone (GH), prolactin (PRL), a human placental lactogen (hPL), a gonadotrophin (e.g. lutenising hormone, follicle stimulating hormone), a thyroid stimulating hormone (TSH), a member of the pro-opiomelanocortin (POMC) family, vasopressin and oxytocin, a natriuretic hormone, parathyroid hormone (PTH), calcitonin, insulin, a glucagon, somatostatin and a gastrointestinal hormone.

The polypeptide may be a Tachykinin peptide (e.g. Substance P, Kassinin, Neurokinin A, Eledoisin, Neurokinin B), a vasoactive intestinal peptide (e.g. VIP (Vasoactive Intestinal Peptide; PHM27), PACAP (Pituitary Adenylate Cyclase Activating Peptide), Peptide PHI 27 (Peptide Histidine Isoleucine 27), GHRH 1-24 (Growth Hormone Releasing Hormone 1-24), Glucagon, Secretin), a pancreatic polypeptide-related peptide (e.g. NPY, PYY (Peptide YY), APP (Avian Pancreatic Polypeptide), PPY (Pancreatic PolY-peptide), an opioid peptide (e.g. Proopiomelanocortin (POMC) peptides, Enkephalin pentapeptides, Prodynorphin peptide, a calcitonin peptide (e.g. Calcitonin, Amylin, AGG01) or another peptide (e.g. B-type Natriuretic Peptide (BNP)).

The polypeptide may be a growth factor selected from a member of the epidermal growth factor (EGF) family, platelet-derived growth factor family (PDGF), fibroblast growth factor family (FGF), Transforming Growth Factors-β family (TGFs-β), Transforming Growth Factor-α (TGF-α), Erythropoietin (Epo), Insulin-Like Growth Factor-I (IGF-I), Insulin-Like Growth Factor-II (IGF-II). Typically, the growth factor is a Transforming growth factor beta (TGF-β), a Nerve growth factor (NGF), a Neurotrophin, a Platelet-derived growth factor (PDGF), Erythropoietin (EPO), Thrombopoietin (TPO), Myostatin (GDF-8), a Growth differentiation factor-9 (GDF9), Acidic fibroblast growth factor (aFGF or FGF-1), Basic fibroblast growth factor (bFGF or FGF-2), Epidermal growth factor (EGF) or a Hepatocyte growth factor (HGF).

The polypeptide may be a cytokine selected from Interleukin-1 (IL-1), Interleukin-2 (IL-2), Interleukin-6 (IL-6) Interleukin-8 (IL-8), Tumor Necrosis Factor-α (TNF-α), Tumor Necrosis Factor-β (TNF-β), Interferon-γ (INF-γ) and a Colony Stimulating Factor (CSF). Typically the cytokine is a Granulocyte-colony stimulating factor (G-CSF) or a Granulocyte-macrophage colony stimulating factor (GM-CSF).

The polypeptide may be a blood-clotting factor such as Factor VIII, Factor V, von Willebrand factor or coagulation factor III.

Antibodies

An antibody for use in the invention may either be a whole antibody or an antigen- or ligand-binding fragment thereof.

Whole Antibodies

In one embodiment, the antibody is an immunoglobulin (Ig) monomer, dimer, tetramer, pentamer, or other oligomer. Each antibody monomer may comprise four polypeptide chains (for example, a conventional antibody consisting of two identical heavy chains and two identical light chains). Alternatively, each antibody monomer consists of two polypeptide chains (for example, a heavy chain antibody consisting of two identical heavy chains).

The antibody can be any class or isotype of antibody (for example IgG, IgM, IgA, IgD or IgE) or any subclass of antibody (for example IgG subclasses IgG1, IgG2, IgG3, IgG4 or IgA subclasses IgA1 or IgA2). Typically, the antibody is an IgG such as an IgG1, IgG2 or IgG4 antibody. Usually, the antibody is an IgG1 or IgG2 antibody.

Typically the antibody or antigen-binding fragment is of mammalian origin. The antibody may thus be a primate, human, rodent (e.g. mouse or rat), rabbit, ovine, porcine, equine or camelidae antibody or antibody fragment. The antibody or antibody fragment may be of shark or chicken origin.

The antibody may be a monoclonal or polyclonal antibody. Monoclonal antibodies are obtained from a population of substantially homogenous antibodies that are directed against a single determinant on the antigen. A population of polyclonal antibodies comprises a mixture of antibodies directed against different epitopes.

Antigen- or Ligand-Binding Fragments

The antigen-binding fragment can be any fragment of an antibody which retains antigen- or ligand-binding ability, for example a Fab, F(Ab')$_2$, Fv, disulphide-linked Fv, single chain Fv (scFv), disulphide-linked scFv, diabody, linear antibody, domain antibody or multispecific antibody. Such fragments comprise one or more antigen or ligand binding sites. In one embodiment, the antigen- or ligand-binding fragment comprises four framework regions (e.g. FR1, FR2, FR3 and FR4) and three complementarity-determining regions (e.g. CDR1, CDR2 and CDR3). Methods suitable for detecting ability of a fragment to bind an antigen or ligand are well known in the art, for example immunoassays and phage display.

The antibody or binding fragment may be a monospecific, bispecific or multispecific antibody. A multispecific antibody has binding specificity for at least one, at least two, at least three, at least four or more different epitopes, antigens or ligands A bispecific antibody is able to bind to two different epitopes, antigens or ligands. For example, a bispecific antibody may comprise two pairs of $V_H$ and $V_L$, each $V_H/V_L$ pair binding to a single antigen or epitope. Methods for preparing bispecific antibodies are known in the art, for example involving coexpression of two immunoglobulin heavy chain-light chain pairs, fusion of antibody variable domains with the desired binding specificities to immunoglobulin constant domain sequences, or chemical linkage of antibody fragments.

The bispecific antibody "diabody" comprises a heavy chain variable domain connected to a light chain variable domain in the same polypeptide chain ($V_H$-$V_L$). Diabodies can be generated using a linker (e.g. a peptide linker) that is too short to allow pairing between the two domains on the same chain, so that the domains are forced to pair with the complementary domains of another chain and create a dimeric molecule with two antigen- or ligand-binding sites.

A suitable scFv antibody fragment may comprise $V_H$ and $V_L$ domains of an antibody wherein these domains are present in a single polypeptide chain. Generally, the Fv polypeptide further comprises a polypeptide linker between the $V_H$ and $V_L$ domains, which enables the scFv to form the desired structure for antigen binding.

A domain antibody for use in the methods of the invention may essentially consist of a light chain variable domain (e.g. a $V_L$) or of a heavy chain variable domain (e.g. a $V_H$). The heavy chain variable domain may be derived from a conventional four-chain antibody or from a heavy chain antibody (e.g. a camelidae $V_{HH}$).

Modifications

The whole antibody or fragment thereof may be associated with other moieties, such as linkers, which may be used to join together two or more fragments or antibodies. Such linkers may be chemical linkers or can be present in the form of a fusion protein with a fragment or whole antibody. The linkers may thus be used to join together whole antibodies or fragments, which have the same or different binding specificities.

In a further embodiment, the antibody or antigen- or ligand-binding fragment is linked to a further moiety such as a toxin, therapeutic drug (e.g. chemotherapeutic drug), radioisotope, liposome or prodrug-activating enzyme. The type of further moiety will depend on the end use of the antibody or antigen-binding fragment.

The antibody or antigen- or ligand-binding fragment may be linked to one or more small molecule toxins (e.g. calicheamicin, maytansine, trichothene and CC1065) or an enzymatically active toxin or fragment thereof (e.g. diphtheria toxin, exotoxin A chain from *Pseudomonas aeruginosa*, ricin A chain, abrin A chain, modeccin A chain, alpha-sarcin, *Aleurites fordii* proteins, dianthin proteins, curcin, crotin, gelonin, mitogellin, restrictocin, phenomycin, enomycin or tricothecenes).

Radioisotopes suitable for linking to the antibody or antigen-binding fragments include, but are not limited to $Tc^{99}$, $At^{211}$, $I^{131}$, $I^{125}$, $Y^{90}$, $Re^{186}$, $Re^{188}$, $Sm^{153}$, $Bi^{212}$ and $P^{32}$.

The antibody or antigen- or ligand-binding fragment may be linked for example, to a prodrug-activating enzyme that converts or is capable of converting a prodrug to an active anti-cancer drug. For example, alkaline phosphatase can be used to convert phosphate-containing prodrugs into free drugs, arylsufatase may be used to convert sulfate-containing prodrugs into free drugs, cytosine deaminase may be used to convert non-toxic 5-fluorocytosine into the anti-cancer drug 5-fluorouracil; and proteases such as serratia protease, thermolysin, subtilisin, carboxypeptidases and cathepsins are useful for converting peptide-containing prodrugs into free drugs. The enzyme may be a nitroreductase which has been identified as useful in the metabolism of a number of prodrugs in anti-cancer gene therapy. Alternatively, antibodies or antigen- or ligand-binding fragments with enzymatic activity can be used to convert prodrugs into free active drugs.

A suitable chemotherapeutic agent may include, but is not limited to an alkylating agent such as thiotepa and cyclosphosphamide; an alkyl sulfonate such as busulfan, improsulfan and piposulfan; an aziridine such as benzodopa, carboquone, meturedopa and uredopa; a nitrogen mustard such as chlorambucil, chlornaphazine, ifosfamide, melphalan; a nitrosurea such as carmustin and fotemustine; an anti-metabolite such as methotrexate and 5-fluorouracil (5-FU); a folic acid analogue such as denopterin and pteropterin; a purine analogue such as fludarabine and thiamiprine; a pyrimidine analogue such as ancitabine, azacitidine, carmofur and doxifluridine; a taxoid such as paclitaxel and doxetaxel; and pharmaceutically acceptable salts, acids or derivatives of any of the above.

In another embodiment, the antibody or antibody fragment may be PEGylated. Thus, one or more polyethylene glycol molecules may be covalently attached to the antibody molecule or antibody fragment molecule. From one to three polyethylene glycol molecules may be covalently attached to each antibody molecule or antibody fragment molecule. Such PEGylation is predominantly used to reduce the immunogenicity of an antibody or antibody fragment and/or increase the circulating half-life of the antibody or antibody fragment.

Chimeric, Humanized or Human Antibodies

In one embodiment the antibody or antigen- or ligand-binding fragment is a chimeric antibody or fragment thereof comprising sequence from different natural antibodies. For example, the chimeric antibody or antibody fragment may comprise a portion of the heavy and/or light chain identical or homologous to corresponding sequences in antibodies of a particular species or antibody class, while the remainder of the chain is identical or homologous to corresponding sequences in antibodies of another species or antibody class. Typically, the chimeric antibody or antibody fragment comprises a chimera of mouse and human antibody components.

Humanized forms of non-human antibodies are chimeric antibodies that contain minimal sequence derived from non-human immunoglobulin. A suitable humanized antibody or antibody fragment may comprise for example, immunoglobulin in which residues from a hypervariable region (e.g. derived from a CDR) of the recipient antibody or antigen- or ligand-binding fragment are replaced by residues from a hypervariable region of a non-human species (donor antibody) such as mouse, rat, rabbit or non-human primate having the desired specificity, affinity and/or capacity. In some instances, some framework region residues of the human immunoglobulin may be replaced by corresponding non-human residues.

As an alternative to humanization, human antibodies or antigen-binding fragments can be generated. For example, transgenic animals (e.g. mice) can be produced that are capable, upon immunization, of producing a full repertoire of human antibodies in the absence of endogenous immunoglobulin production. For example, homozygous deletion of the antibody heavy-chain joining region ($J_H$) gene in chimeric and germ-line mutant mice can result in complete inhibition of endogenous antibody production. Human germ-line immunoglobulin genes can be transferred to such germ-line mutant mice to result in the production of human antibodies upon antigen challenge. A human antibody or antigen-binding fragment can also be generated in vitro using the phage display technique.

Targets

An antibody or antigen- or ligand-binding fragment capable of binding any target antigen is suitable for use in the methods of the present invention. The antibody or antibody fragment may be capable of binding to an antigen or ligand associated with an autoimmune disorder (e.g. Type I diabetes, multiple sclerosis, rheumatoid arthritis, systemic lupus erythematosus, Crohn's disease and myasthenia gravis), an antigen or ligand associated with a cancer or an inflammatory state, an antigen associated with osteoporosis, an antigen associated with Alzheimer's disease, or a bacterial or viral antigen.

In particular, the target to which an antibody or antigen- or ligand-binding fragment may bind can be a CD antigen, growth factor, growth factor receptor, cell surface receptor such as an apoptosis receptor, a protein kinase or an oncoprotein. The antibody or antigen-binding fragment, for example a chimeric, humanized or human IgG1, IgG2 or IgG4 monoclonal antibody or antibody fragment, may thus be capable of binding to tumour necrosis factor α (TNF-α), interleukin-2 (IL-2), interleukin-6 (IL-6), glycoprotein IIb/IIIa, CD33, CD52, CD20, CD11a, CD3, RSV F protein, HER2/neu (erbB2) receptor, vascular endothelial growth factor (VEGF), epidermal growth factor receptor (EGFR), anti-TRAILR2 (anti-tumour necrosis factor-related apoptosis-inducing ligand receptor 2), complement system protein C5, α4 integrin or IgE.

More specifically, in the context of anti-cancer monoclonal antibodies, the antibody or antigen-binding fragment may be an antibody or antibody fragment capable of binding to epithelial cell adhesion molecule (EpCAM), mucin-1 (MUC1/Can-Ag), EGFR, CD20, carcinoembryonic antigen (CEA), HER2, CD22, CD33, Lewis Y and prostate-specific membrane antigen (PMSA). Again, the antibody is typically a chimeric, humanized or human IgG1, IgG2 or IgG4 monoclonal antibody.

Suitable monoclonal antibodies include, but are not limited to: infliximab (chimeric antibody, anti-TNFα), adalimumab (human antibody, anti-TNFα), basiliximab (chimeric antibody, anti-IL-2), abciximab (chimeric antibody, anti-GpIIb/IIIa), daclizumab (humanized antibody, anti-IL-2), gemtuzumab (humanized antibody, anti-CD33), alemtuzumab (humanized antibody, anti-CD52), edrecolomab (murine Ig2a, anti-EpCAM), rituximab (chimeric antibody, anti-CD20), palivizumab (humanized antibody, RSV target), trastuzumab (humanized antibody, anti-HER2/neu(erbB2) receptor), bevacizumab (humanized antibody, anti-VEGF), cetuximab (chimeric antibody, anti-EGFR), eculizumab (humanized antibody, anti-complement system protein C5), efalizumab (humanized antibody, anti-CD11a), ibritumomab (murine antibody, anti-CD20), muromonab-CD3 (murine antibody, anti-T cell CD3 receptor), natalizumab (humanized antibody, anti-α 4 integrin), nimotuzumab (humanized IgG1, anti-EGF receptor), omalizumab (humanized antibody, anti-IgE), panitumumab (human antibody, anti-EGFR), ranibizumab (humanized antibody, anti-VEGF), ranibizumab (humanized antibody, anti-VEGF) and I-131 tositumomab (humanized antibody, anti-CD20).

Preparation of Antibodies

Suitable monoclonal antibodies may be obtained for example, by the hybridoma method (e.g. as first described by Kohler et al Nature 256:495 (1975)), by recombinant DNA methods and/or following isolation from phage or other antibody libraries.

The hybridoma technique involves immunisation of a host animal (e.g. mouse, rat or monkey) with a desired immunogen to elicit lymphocytes that produce or are capable of producing antibodies that specifically bind to the immunogen. Alternatively, lymphocytes may be immunized in vitro. Lymphocytes are then fused with myeloma cells using a suitable fusing agent, such as polyethylene glycol, to form a hybridoma cell.

An antibody or antibody fragment can also be isolated from antibody phage libraries as an alternative to traditional monoclonal antibody hybridoma techniques for isolation of monoclonal antibodies. In particular, phage display may be used to identify antigen- or ligand-binding fragments for use in the methods of the invention. By using phage display for the high-throughput screening of antigen-antibody or ligand-antibody binding interactions, antibody fragments displayed on phage coat proteins can be isolated from a phage display library. By immobilising a target antigen or ligand on a solid support, a phage that displays an antibody capable of binding that antigen or ligand will remain on the support while others can be removed by washing. Those phages that remain bound can then be eluted and isolated, for example after repeated cycles of selection or panning. Phage eluted in the final selection can be used to infect a suitable bacterial host from which phagemids can be collected and the relevant DNA sequence excised and sequenced to identify the relevant antigen- or ligand-binding fragment.

Polyclonal antiserum containing the desired antibodies is isolated from animals using techniques well known in the art. Animals such as sheep, rabbits or goats may be used for example, for the generation of antibodies against an antigen of interest by the injection of this antigen (immunogen) into the animal, sometimes after multiple injections. After collection of antiserum, antibodies may be purified using immunosorbent purification or other techniques known in the art.

The antibody or antigen- or ligand-binding fragment used in the method of the invention may be produced recombinantly from naturally occurring nucleotide sequences or synthetic sequences. Such sequences may for example be isolated by PCR from a suitable naturally occurring template (e.g. DNA or RNA isolated from a cell), nucleotide sequences isolated from a library (e.g. an expression library), nucleotide sequences prepared by introducing mutations into a naturally occurring nucleotide sequence (using any suitable technique known, e.g. mismatch PCR), nucleotide sequence prepared by PCR using overlapping primers, or nucleotide sequences that have been prepared using techniques for DNA synthesis. Techniques such as affinity maturation (for example, starting from synthetic, random or naturally occurring immunoglobulin sequences), CDR grafting, veneering, combining fragments derived from different immunoglobulin sequences, and other techniques for engineering immunoglobulin sequences may also be used.

Such nucleotide sequences of interest may be used in vitro or in vivo in the production of an antibody or antigen-binding fragment for use in the invention, in accordance with techniques well known to those skilled in the art.

For recombinant production of a monoclonal antibody or antibody fragment, the nucleic acid encoding it is isolated and inserted into a replicable vector for further cloning or for expression. The vector components generally including, but is not limited to one or more of the following: a signal sequence, an origin of replication, one or more marker genes, an enhancer element, a promoter, and a transcription termination sequence. Suitable host cells for cloning or expressing the DNA in the vectors are prokaryote, yeast, or higher eukaryote cells such as $E.\ coli$ and mammalian cells such as CHO cells. Suitable host cells for the expression of glycosylated antibody are derived from multi-cellular organisms. Host cells are transformed with the expression or cloning vectors for antibody production and cultured in conventional nutrient media modified as appropriate for inducing promoters, selecting transformants, or amplifying the genes encoding the desired sequences.

When using recombinant techniques, the antibody can be produced intracellularly or directly secreted into the medium. If the antibody is produced intracellularly, as a first step, the particulate debris of either host cells or lysed cells, is removed, for example by centrifugation or ultra filtration. Where the antibody is secreted into the medium, supernatants from expression systems are generally first concentrated using a commercially available protein concentration filter. The antibody composition prepared from the cells can be purified using, for example, hydyoxylapatite chromatography, gel electrophoresis, dialysis and affinity chromatography.

The purified antibodies may then be isolated and optionally made into antigen- or ligand-binding fragments and/or derivatised.

Enzymes

Any protein enzyme is suitable for use in the invention. Such an enzyme comprises an active site and is capable of binding a substrate. The enzyme may be a monomer consisting of one polypeptide chain. Alternatively, the enzyme may be a dimer, tetramer or oligomer consisting of multiple polypeptide chains. The dimer, tetramer or oligomer may be a homo- or hetero-dimer, tetramer or oligomer respectively. For example, the enzyme may need to form an aggregate (e.g. a dimer, tetramer or oligomer) before full biological activity or enzyme function is conferred. The enzyme may be an allosteric enzyme, an apoenzyme or a holoenzyme.

The enzyme may be conjugated to another moiety (e.g. a ligand, antibody, carbohydrate, effector molecule, or protein fusion partner) and/or bound to one or more cofactors (e.g. coenzyme or prosthetic group).

The moiety to which the enzyme is conjugated may include lectin, avidin, a metabolite, a hormone, a nucleotide sequence, a steroid, a glycoprotein, a glycolipid, or any derivative of these components.

Cofactors include inorganic compounds (e.g. metal irons such as iron, manganese, cobalt, copper, zinc, selenium, molybdenum) or organic compounds (e.g. flavin or heme). Suitable coenzymes include riboflavin, thiamine, folic acid which may carry hydride iron ($H^-$) carried by NAD or $NADP^+$, the acetyl group carried by coenzyme A, formyl, methenyl or methyl groups carried by folic acid and the methyl group carried by S-adenosyl methionine.

In another embodiment, the enzyme may be PEGylated especially if the enzyme is a therapeutic enzyme that is administered to a patient. Thus, one or more polyethylene glycol molecules may be covalently attached to the enzyme molecule. From one to three polyethylene glycol molecules may be covalently attached to each enzyme molecule. Such PEGylation is predominantly used to reduce the immunogenicity of an enzyme and/or increase the circulating half-life of the enzyme.

A suitable enzyme includes any enzyme classified under the International Union of Biochemistry and Molecular Biology Enzyme classification system of EC numbers including an oxidoreductase (EC 1), a transferase (EC 2), a hydrolase (EC 3), a lyase (EC 4), an isomerase (EC 5) or a ligase (EC 6). A typical enzyme is any enzyme that is used industrially.

An enzyme that is specific for any type of substrate is suitable for use in the present invention. Examples of a suitable enzyme includes a α-galactosidase, β-galactosidase, luciferase, serine proteinase, endopeptidase (e.g. cysteine endopeptidase), caspase, chymase, chymotrypsin, endopeptidase, granzyme, papain, pancreatic elastase, oryzin, plasmin, renin, subtilisin, thrombin, trypsin, tryptase, urokinase, amylase (e.g. α-amylase), xylanase, lipase, transglutaminase, cell-wall-degrading enzyme, glucanase (e.g. β-glucanase), glucoamylase, coagulating enzyme, milk protein hydrolysate, cell-wall degrading enzyme, blood coagulating enzyme, hementin, lysozyme, fibre-degrading enzyme, phytase, cellulase, hemicellulase, polymerase, protease, mannanase or glucoamylase.

An enzyme preserved according to the invention may thus be a therapeutic enzyme that is used to treat a disease or other medical condition, an enzyme used in industry for the production of bulk products such as glucose or fructose, in food processing and food analysis, in laundry and automatic dishwashing detergents, in the textile, pulp, paper and animal feed industries, as a catalyst in synthesis or fine chemicals, in diagnostic applications such as in clinical diagnosis, in biosensors or in genetic engineering.

Therapeutic enzymes to which the present invention can be applied include:
  a DNAase, for example a recombinant DNAase I such as Pulmozyme or Dornase that cleaves the DNA in the pulmonary mucus of children having cystic fibrosis;
  a gastric lipase such as Meripase which is a recombinant mammalian gastric lipase for the treatment of lipid malabsorption related to exocrine pancreatic lipase insufficiency;
  a mannose-terminated glucocerebrosidase such as Cerezyme which is a recombinant mannose-terminated glucocerebrosidase for the treatment of Gaucher disease, an inherited disorder that is caused by a deficiency in the enzyme glucocerebrosidase;
  α-galactosidase which is used in the treatment of the related glycogen storage disease Fabry disease;
  an adenosine deaminase (ADA) such as Pegademase that is used to treat ADA deficiency, a severe combined immunodeficiency;
  a phenylalanine ammonia lyase such as the PEGylated recombinant phenylalanine ammonia lyase Kuvan that is used for the treatment of phenylketonuria;
  tissue plasminogen activator, urokinase and streptokinase which are used in blood fibrinolysis to treat blood clots;
  a urate oxidase such as Elitek (rasburicase) which is a recombinant urate-oxidase that is produced by a genetically modified yeast and that is used in the treatment or prophylaxis of hyperuricemia in patients with leukaemia or lymphoma;
  L-asparaginase which is used in the treatment of childhood acute lymphoblastic leukaemia;
  Factor VIIa, used by patients with hemophilia;
  Factor IX which is used in the treatment of hemophilia B; and
  a superoxide dismutase such as the bovine superoxide dismutase Orgotein that is used for the treatment of familial amyotrophic lateral sclerosis.

Enzymes for use in food applications such as baking include amylases, xylanases, oxidoreductases, lipases, proteases and transglutaminase. Enzymes for use in fruit juice production and fruit processing include cell-wall-degrading enzymes. Enzymes for use in brewing include bacterial α-amylase, β-glucanase and glucoamylase in mashing, fungal α-amylase in fermentation and cysteine endopeptidase in post fermentation. Enzymes for use in dairy applications include coagulating enzymes, lipase, lysozyme, milk protein hydrolysates, transglutaninase, and β-galactosidase. Enzymes for use in detergent compositions include proteases, amylases, lipases, cellulases and mannanase. Enzymes for use in animal feed include fibre-degrading enzymes, phytases, proteases and amylases. Enzymes for use in pulp and paper processing include cellulases and hemicellulases.

The enzyme may alternatively be an enzyme used in research and development applications. For example, luciferases may be used for real-time imaging of gene expression in cell cultures, individual cells and whole organisms. Further, luciferases may be used as reporter proteins in molecular studies, for example to test the activity of transcription from specific promoters in cells transfected with luciferase. Enzymes may also be used in drug design for example in the testing of enzyme inhibitors in the laboratory. Further, enzymes may be used in biosensors (for example, a blood glucose biosensor using glucose oxidase).

The luciferase enzyme may be a firefly, beetle or railroad worm luciferase, or a derivative thereof. In particular, the luciferase may be derived from a North American firefly (*Phorinus pyralis*), *Luciola cruciata* (japanese firefly), *Luciola lateralis* (japanese firefly), *Luciola mingelica* (russian firefly), *Beneckea hanegi* (marine bacterial luciferase), *Pyrophorus plagiophthalamus* (click beetle), *Pyrocelia miyako* (firefly) *Ragophthalamus ohbai* (railroad worm), *Pyrearinus termitilluminans* (click beetle), *Phrixothrix hirtus* (railroad worm), *Phrixothrix vivianii*, *Hotaria parvula* and *Photuris pensilvanica*, and mutated variants thereof.

Typically the α-galactosidase or β-galactosidase is derived from bacteria (such as *Escherichia coli*.), a mammal (such as human, mouse, rat) or other eukaryote.

The enzyme maybe a naturally-occurring enzyme or a synthetic enzyme. Such enzymes may be derived from a host animal, plant or a microorganism.

Microbial strains used in the production of enzymes may be native strains or mutant strains that are derived from native strains by serial culture and selection, or mutagenesis and selection using recombinant DNA techniques. For example the microorganism may be a fungus e.g. *Thermomyces acermonium, Aspergillus, Penicillium, Mucor, Neurospora* and *Trichoderma*. Yeasts such as *Saccharomyces cereviseae* or *Pishia pastoris* may also be used in the production of enzymes for use in the methods of the present invention.

A synthetic enzyme may be derived using protein-engineering techniques well known in the art such as rational design, directed evolution and DNA shuffling.

Host organisms may be transformed with a nucleotide sequence encoding a desired enzyme and cultured under conditions conducive to the production of the enzyme and which facilitate recovery of the enzyme from the cells and/or culture medium.

Vaccine Immunogens

A vaccine immunogen suitable for use in the invention includes any immunogenic component of a vaccine. The vaccine immunogen comprises an antigen that can elicit an immune response in an individual when used as a vaccine against a particular disease or medical condition. The vaccine immunogen may be provided by itself prior to formulation of a vaccine preparation or it may be provided as part of a vaccine preparation. The vaccine immunogen may be a subunit vaccine, a conjugate useful as a vaccine or a toxoid. The vaccine immunogen may be a protein, bacterial-specific protein, mucoprotein, glycoprotein, peptide, lipoprotein, polysaccharide, peptidoglycan, nucleoprotein or fusion protein.

The vaccine immunogen may be derived from a microorganism (such as a bacterium, virus, fungi), a protozoan, a tumour, a malignant cell, a plant, an animal, a human, or an allergen. The vaccine immunogen is preferably not a viral particle. Thus, the vaccine immunogen is preferably not a whole virus or virion, virus-like particle (VLP) or virus nucleocapsid. The preservation of such viral particles is described in WO 2008/114021.

The vaccine immunogen may be synthetic, for example as derived using recombinant DNA techniques. The immunogen may be a disease-related antigen such as a pathogen-related antigen, tumour-related antigen, allergy-related antigen, neural defect-related antigen, cardiovascular disease antigen, rheumatoid arthritis-related antigen.

In particular, the pathogen from which the vaccine immunogen is derived may include human papilloma viruses (HPV), HIV, HSV2/HSV1, influenza virus (types A, B and C), para influenza virus, polio virus, RSV virus, rhinoviruses, rotaviruses, hepatitis A virus, norwalk virus, enteroviruses, astroviruses, measles virus, mumps virus, varicella-zoster virus, cytomegalovirus, epstein-barr virus, adenoviruses, rubella virus, human T-cell lymphoma type I virus (HTLV-I), hepatitis B virus (HBV), hepatitis C virus (HCV), hepatitis D virus, poxvirus, vaccinia virus, *Salmonella, Neisseria, Borrelia, Clamydia, Bordetella* such as *Bordetella pertussis, Plasmodium, Coxoplasma, Pneumococcus, Meningococcus, Cryptococcus, Streptococcus, Vibriocholerae, Yersinia* and in particular *Yersinia pestis, Staphylococcus, Haemophilus, Diptheria, Tetanus, Pertussis, Escherichia, Candida, Aspergillus, Entamoeba, Giardia* and *Trypanasoma*. The vaccine may further be used to provide a suitable immune response against numerous veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and, bovine viral diarrhea virus.

Tumor-associated antigens include for example, melanoma-associated antigens, mammary cancer-associated antigens, colorectal cancer-associated antigens or prostate cancer-associated antigens An allergen-related antigen includes any allergen antigen suitable for use in a vaccine to suppress an allergic reaction in an individual to which the vaccine is administered (e.g. antigens derived from pollen, dust mites, insects, food allergens, dust, poisons, parasites).

Subunit Vaccine Immunogens

A suitable subunit vaccine immunogen includes any immunogenic subunit of a protein, lipoprotein or glycoprotein derived from a microorganism (for example a virus or bacteria). Alternatively, the subunit vaccine immunogen may be derived from a disease-related antigen such as a tumour related protein. The subunit vaccine immunogen may be a naturally occurring molecule or a synthetic protein subunit. The vaccine immunogen may be a full-length viral or bacterial protein, glycoprotein or lipoprotein or a fragment of the full-length viral or bacterial protein, glycoprotein or lipoprotein.

A viral protein suitable as a subunit vaccine immunogen may be derived from a structural or non-structural viral protein. A suitable viral subunit immunogen is capable of stimulating a subject's immune system even in the absence of other parts of the virus. A suitable viral subunit vaccine immunogen includes a capsid protein, surface glycoprotein, envelope protein, hexon protein, fiber protein, coat protein or immunogenic fragment or derivative of such proteins or glycoproteins.

For example, the viral subunit vaccine immunogen may consist of a surface protein of the Influenza A, B or C virus. In particular, the vaccine immunogen may be a hemagglutinin (HA), neuraminidase (NA), nucleoprotein, M1, M2, NS1, NS2(NEP), PA, PB1, PB1-F2 and or PB2 protein, or an immunogenic derivative or fragment of any of these proteins. The immunogen may be HA1, HA2, HA3, HA4, HA5, HA6, HA7, HA8, HA9, HA10, HA11, HA12, HA13, HA14, HA15 and/or HA16, any immunogenic fragment or derivative thereof and any combination of the HA proteins, fragments or derivatives. The neuraminidase may be neuraminidase 1 (N1) or neuraminidase 2 (N2).

The viral subunit vaccine immunogen may be a hepatitis B virus viral envelope protein or a fragment or derivative thereof. For example, the subunit vaccine immunogen may be the hepatitis B surface antigen (HbsAg) or an immunogenic fragment or derivative thereof.

Typically, the bacterial subunit vaccine immunogen is a bacterial cell wall protein (e.g. flagellin, outer membrane protein, outer surface protein), a polysaccharide antigen (e.g. from *Neisseria meningitis, Streptococcus pneumonia*), toxin or an immunogenic fragment or derivative of such proteins, polysaccharides or toxins.

Derivatives of naturally occurring proteins include proteins with the addition, substitution and/or deletion of one or more amino acids. Such amino acid modifications can be generated using techniques known in the art, such as site-directed mutagenesis.

The subunit vaccine immunogen may be a fusion protein comprising a fusion protein partner linked with for example, a bacterial or viral protein or an immunogenic fragment or derivative thereof. A suitable fusion protein partner may prevent the assembly of viral fusion proteins into multimeric forms after expression of the fusion protein. For example, the fusion protein partner may prevent the formation of virus-like structures that might spontaneously form if the viral protein was recombinantly expressed in the absence of the fusion protein partner. A suitable fusion partner may also facilitate purification of the fusion protein, or enhance the recombinant expression of the fusion protein product. The fusion protein may be maltose binding protein, poly-histidine segment capable of binding metal ions, antigens to which antibodies bind, S-Tag, glutathione-S-transferase, thioredoxin, beta-galactosidase, epitope tags, green fluorescent protein, streptavidin or dihydrofolate reductase.

A subunit vaccine immunogen may be prepared using techniques known in the art for the preparation of for example, isolated peptides, proteins, lipoproteins, or glycoproteins. For example, a gene encoding a recombinant protein of interest can be identified and isolated from a pathogen and expressed in *E. coli* or some other suitable host for mass production of proteins. The protein of interest is then isolated and purified from the host cell (for example by purification using affinity chromatography).

In the case of viral subunit immunogens, the subunit may be purified from the viral particle after isolating the viral particle, or by recombinant DNA cloning and expression of the viral subunit protein in a suitable host cell. A suitable host cell for preparing viral particles must be capable of being infected with the virus and of producing the desired viral antigens. Such host cells may include microorganisms, cultured animal cells, transgenic plants or insect larvae. Some proteins of interest may be secreted as a soluble protein from the host cell. In the case of viral envelope or surface proteins, such proteins may need to be solubilized with a detergent to extract them from the viral envelope, followed by phase separation in order to remove the detergent.

A subunit vaccine immunogen may be combined in the same preparation and preserved together with one, two three or more other subunit vaccine immunogens.

Toxoids

The invention can be applied to toxoids. A toxoid is a toxin, for example derived from a pathogen, animal or plant, that is immunogenic but has been inactivated (for example by genetic mutation, chemical treatment or by conjugation to another moiety) to eliminate toxicity to the target subject. The toxin may be for example, a protein, lipoprotein, polysaccharide, lipopolysaccharide or glycoprotein. The toxoid may thus be an endotoxin or an exotoxin that has been toxoided.

The toxoid may be a toxoid derived from a bacterial toxin such as tetanus toxin, diphtheria toxin, pertussis toxin, botulinum toxin, *C. difficile* toxin, Cholera toxin, shiga toxin, anthrax toxin, bacterial cytolysins or pneumolysin and fragments or derivatives thereof. The toxoid may therefore be tetanus toxoid, diphtheria toxoid or pertussis toxoid. Other toxins from which a toxoid can be derived include poisons isolated from animals or plants, for example from *Crotalis atrox*. Typically, the toxoid is derived from botulinum toxin or anthrax toxin. For example, the botulinum toxin may be derived from *Clostridium botulinum* of serotype A, B, C, D, E, F or G. The vaccine immunogen derived from a botulinum toxin may be combined in the same preparation and preserved together with one or more other vaccine immunogens derived from a botulinum toxin (eg a combination of immunogens derived from botulinum serotypes A, B, C, D, E, F or G, such as for example A, B and E).

The anthrax toxin may be derived from a strain of *Bacillus anthracis*. The toxoid may consist of one of more components of the anthrax toxin, or derivatives of such components, such as protective antigen (PA), the edema factor (EF) and the lethal factor (LF). Typically the toxoid derived from the anthrax toxin consists of protective antigen (PA).

The toxoid may be conjugated to another moiety, for example as a fusion protein, for use as a toxoid vaccine. A suitable moiety in a conjugate toxoid includes a substance that aids purification of the toxoid (e.g histidine tag) or reduces toxicity to a target subject. Alternatively, the toxoid may act as an adjuvant by increasing the immunogenicity of an antigen to which it is attached. For example, the B polysaccharide of *Haemophilus influenzae* may be combined with diptheria toxoid.

A vaccine immunogen may be combined in the same preparation and preserved together with one, two three or more vaccine immunogens. For example, a diphtheria toxoid may be preserved with tetanus toxoid and pertussis vaccine (DPT). Diptheria toxoid may be preserved with just tetanus toxoid (DT), or diphtheria toxoid may be preserved with diphtheria toxoid, tetanus toxoid and acellular Pertussis (DTaP).

Techniques for the preparation of toxoids are well known to those skilled in the art. Toxin genes may be cloned and expressed in a suitable host cell. The toxin product is then purified and may be converted to toxoid chemically, for example using formalin or glutaraldehyde. Alternatively, a toxin gene may be engineered so that it encodes a toxin having reduced or no toxicity e.g. by addition, deletion and/or substitution of one or more amino acids. The modified toxin can then be expressed in a suitable host cell and isolated. The toxicity of toxin genes may also be inactivated by conjugation of toxin genes or fragments thereof to a further moiety (e.g. polysaccharide or polypeptide).

Conjugate Vaccine Immunogens

A conjugate vaccine immunogen may be a conjugate of an antigen (for example a polysaccharide or other hapten) to a carrier moiety (for example a peptide, polypeptide, lipoprotein, glycoprotein, mucoprotein or any immunostimulatory derivative or fragment thereof) that stimulates the immunogenicity of the antigen to which it is attached. For example, the conjugate vaccine immunogen may be a recombinant protein, recombinant lipoprotein or recombinant glycoprotein conjugated to an immunogen of interest (for example a polysaccharide).

The conjugate vaccine immunogen may be used in a vaccine against *Streptococcus pneumonia, Haemophilus influenza*, meningococcus (strains A, B, C, X, Y and W135) or pneumococcal strains. For example, the vaccine may be for example, the heptavalent Pneumococcal CRM197 Conjugate Vaccine (PCV7), an MCV-4 or *Haemophilus influenzae* type b (Hib) vaccine.

A conjugate vaccine immunogen may be combined in the same preparation and preserved together with one, two three or more other conjugate vaccine immunogens.

Methods for the preparation of conjugate polysaccharide-protein conjugates are well known in the art. For example, conjugation may occur via a linker (e.g. B-propionamido, nitrophenyl-ethylamine, haloalkyl halides, glycosidic linkages).

Polyethyleneimine

PEI is an aliphatic polyamine characterised by the repeating chemical units denoted as $—(CH_2—CH_2—NH)—$. Reference to PEI herein includes a polyethyleneimine homopolymer or copolymer. The polyethyleneimine copolymer may be a random or block copolymer. For example, PEI may consist of a copolymer of polyethyleneimine and another polymer such as polyethylene glycol (PEG). The polyethyleneimine may be linear or branched.

Reference to PEI also includes derivatised forms of a polyethyleneimine. A polyethyleneimine contains nitrogen atoms at various positions. Nitrogen atoms are present in terminal amino groups, e.g. $R—NH_2$, and in internal groups such as groups interrupting an alkyl or alkylene group within the polymer structure, e.g. $R—N(H)—R'$, and at the intersection of a polymer branch, e.g. $R—N(—R')—R''$ wherein R, R' and R'' may be alkylene groups for example. Alkyl or aryl groups may be linked to the nitrogen centres in addition to or instead of hydrogen atoms. Such alkyl and aryl groups may be substituted or unsubstituted. An alkyl group would be typically a $C_1$-$C_4$ alkyl group, e.g. methyl, ethyl, propyl, isopropyl, butyl, sec.butyl or tert.butyl. The aryl group is typically phenyl.

The PEI may be a polyethyleneimine that has been covalently linked to a variety of other polymers such as polyethylene glycol. Other modified versions of PEI have been generated and some are available commercially: branched PEI 25 kDa, jetPEI®, LMW-PEI 5.4 kDa, Pseudo-dendrimeric PEI, PEI-SS-PEI, PEI-SS-PEG, PEI-g-PEG, PEG-co-PEI, PEG-g-PEI, PEI-co-L lactamide-co-succinamide, PEI-co-N-(2-hydroxyethyl-ethylene imine), PEI-co-N-(2-hydroxypropyl) methacrylamide, PEI-g-PCL-block-PEG, PEI-SS-PHMPA, PEI-g-dextran 10 000 and PEI-g-transferrin-PEG, Pluronic85®/Pluronic123®-g-PEI. The PEI may be permethylated polyethyleneimine or polyethyleneimine-ethanesulfonic acid.

PEI is available in a broad range of number-average molar masses ($M_n$) for example between 300 Da and 800 kDa. Preferably, the number-average molar mass is between 300 and 2000 Da, between 500 and 1500 Da, between 1000 and 1500 Da, between 10 and 100 kDa, between 20 and 100 kDa, between 30 and 100 kDa, between 40 and 100 kDa, between 50 and 100 kDa, between 60 and 100 kDa, between 50 and 70 kDa or between 55 and 65 kDa. A relatively high $M_n$ PEI of approximately 60 kDa or a relatively low $M_n$ of 1200 Da is suitable.

Preferably, the weight-average molar mass ($M_w$) of PEI is between 500 Da and 1000 kDa. Most preferably, the $M_w$ of PEI is between 500 Da and 2000 Da, between 1000 Da and 1500 Da, or between 1 and 1000 kDa, between 100 and 1000 kDa, between 250 and 1000 kDa, between 500 and 1000 kDa, between 600 and 1000 kDa, between 750 and 1000 kDa, between 600 and 800 kDa, between 700 and 800 kDa. A relatively high $M_w$ of approximately 750 kDa or a relatively low $M_w$ of approximately 1300 Da is suitable.

The weight-average molar mass ($M_w$) and number-average molar mass ($M_n$) of PEI can be determined by methods well known to those skilled in the art. For example, $M_w$ may be determined by light scattering, small angle neutron scattering (SANS), X-ray scattering or sedimentation velocity. $M_n$ may be determined for example by gel permeation chromatography, viscometry (Mark-Houwink equation) and colligative methods such as vapour pressure osometry or end-group titration.

Various forms of PEI are available commercially (e.g. Sigma, Aldrich). For example, a branched, relatively high molecular weight form of PEI used herein with an $M_n$ of approximately 60 kDa and a $M_w$ of approximately 750 kDa is available commercially (Sigma P3143). This PEI can be represented by the following formula:

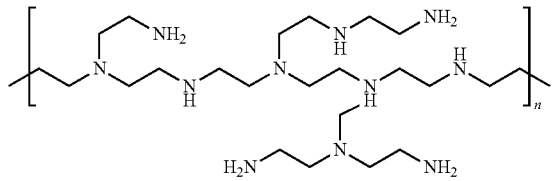

A relatively low molecular weight form of PEI used herein is also available commercially (e.g. Aldrich 482595) which has a $M_w$ of 1300 Da and $M_n$ of 1200 Da.

Compounds of Formula (I) or Physiologically Acceptable Salts or Esters Thereof and Compounds of Formula (II) or Physiologically Acceptable Salts or Esters Thereof The compounds of formula (I) and (II) may be present as a physiologically acceptable salt or ester thereof.

The salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

As used herein, a $C_{1-6}$ alkyl group is preferably a $C_{1-4}$ alkyl group. Preferred alkyl groups are selected from methyl, ethyl, propyl, isopropyl, butyl, isobutyl and tert-butyl. Methyl and ethyl are particularly preferred.

For the avoidance of doubt, the definitions of compounds of formula (I) and formula (II) also include compounds in which the carboxylate anion is protonated to give —COOH and the ammonium or sulfonium cation is associated with a pharmaceutically acceptable anion. Further, for the avoidance of doubt, the compounds defined above may be used in any tautomeric or enantiomeric form.

Compounds of Formula (I)

Typically, $R_1$ represents hydrogen or $C_{1-6}$ alkyl and $R_4$ represents hydrogen. Typically, $R_2$ represents hydrogen or $C_{1-6}$ alkyl. Preferably, $R_1$ represents hydrogen or $C_{1-6}$ alkyl, $R_4$ represents hydrogen and $R_2$ represents hydrogen or $C_{1-6}$ alkyl. More preferably $R_1$ represents hydrogen or $C_{1-6}$ alkyl, $R_4$ represents hydrogen and $R_2$ represents $C_{1-6}$ alkyl.

Preferably, the compound of formula (I) is an N—$C_{1-6}$ alkyl-, N,N-di($C_{1-6}$ alkyl)- or N,N,N-tri($C_{1-6}$ alkyl)-glycine or physiologically acceptable salt or ester thereof, more preferably an N,N-di($C_{1-6}$ alkyl)- or N,N,N-tri($C_{1-6}$ alkyl)-glycine or physiologically acceptable salt or ester thereof. The alkyl group is typically a $C_{1-4}$ alkyl group. Preferred alkyl groups are selected from methyl, ethyl, propyl, isopropyl, butyl, isobutyl and tert-butyl. Methyl and ethyl are particularly preferred.

Preferred compounds of formula (I) are N-methylglycine, N,N-dimethylglycine or N,N,N-trimethylglycine or physiologically acceptable salts or esters thereof. N-Methylglycine is also called sarcosine. N,N-Dimethylglycine is also termed dimethylglycine (DMG) or 2-(dimethylamino)-acetic acid. N,N,N-trimethylglycine is termed trimethylglycine (TMG).

Alternatively, the compound of formula (I) is typically a glycine derivative of formula (IA) or a physiologically acceptable salt or ester thereof:

wherein $R_5$ and $R_6$ independently represent $C_{1-6}$ alkyl, for example $C_{1-4}$ alkyl such as methyl or ethyl; and $R_7$ represents $C_{1-6}$ alkyl, for example $C_{1-4}$ alkyl such as methyl or ethyl, or —$(CH_2)_{2-5}NHC(O)(CH_2)_{5-15}CH_3$. Preferred compounds of formula (IA) are trimethylglycine (TMG) and cocamidopropyl betaine (CAPB) or physiologically acceptable salts or esters thereof. Trimethyglycine is preferred.

Alternatively, the compound of formula (I) is typically a proline derivative of formula (IB) or a physiologically acceptable salt or ester thereof:

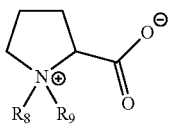

wherein $R_8$ and $R_9$ independently represent $C_{1-6}$ alkyl, for example $C_{1-4}$ alkyl such as methyl or ethyl. Preferably the compound of formula (IB) is an S-proline derivative. Preferably $R_8$ and $R_9$ both represent methyl; this compound is known as proline betaine. S-proline betaine or physiologically acceptable salt or ester thereof is particularly preferred:

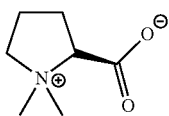

Compounds of formula (IA) or physiologically acceptable salts or esters thereof are preferred.

Preferably, the compound of formula (I) is N, N-dimethylglycine or N, N, N-trimethylglycine or physiologically acceptable salt or ester thereof. Most preferably, the compound of formula (I) is N, N-dimethylglycine or physiologically acceptable salt or ester thereof.

Compounds of Formula (II)

Typically, the carboxylate and amine substituents of $R_c$ are attached to the same carbon atom of the $R_c$ alkyl moiety. Typically $R_c$ is a $C_{2-4}$ or $C_{2-3}$ alkyl moiety.

The compound of formula (II) is typically a sulfone compound of formula (IIA) or a physiologically acceptable salt or ester thereof:

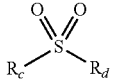

wherein $R_c$ and $R_d$ independently represent $C_{1-6}$ alkyl, for example $C_{1-4}$ alkyl. Preferred alkyl groups are selected from methyl, ethyl, propyl, isopropyl, butyl, isobutyl and tert-butyl. Methyl and ethyl are particularly preferred. A preferred sulfone compound is methylsulfonylmethane (MSM), which is also known as dimethylsulfone ($DMSO_2$).

The compound of formula (II) is typically a compound of formula (IIB) or a physiologically acceptable salt or ester thereof:

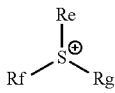

wherein $R_e$ and $R_f$ independently represent $C_{1-6}$ alkyl, for example $C_{1-4}$ alkyl such as methyl or ethyl, and $R_g$ represents $C_{1-6}$ alkyl, for example $C_{1-4}$ alkyl such as methyl or ethyl, substituted with a carboxylate anion and with an amine ($—NH_2$) moiety. Preferably the carboxylate and amine substituents are attached to the same carbon atom. A preferred compound of formula (IIB) is S-methyl-L-methionine (SMM) or a physiologically acceptable salt or ester thereof.

Glycine Derivatives

The excipient may be an N-alkyl-, N,N-dialkyl- or N,N,N-trialkyl-glycine or a physiologically acceptable salt or ester thereof. The alkyl group is typically a $C_{1-6}$ alkyl group such as a $C_{1-4}$ alkyl group. Preferred alkyl groups are selected from methyl, ethyl, propyl, isopropyl, butyl, isobutyl and tert-butyl. Methyl and ethyl are particularly preferred.

Preferred glycine derivatives for use in the invention are N-methylglycine, N,N-dimethylglycine, N,N,N-trimethylglycine and physiologically acceptable salts and esters ester thereof. N-Methyl-glycine is also called sarcosine. N, N-Dimethylglycine is also termed dimethylglycine (DMG) or 2-(dimethylamino)-acetic acid. N,N,N-trimethylglycine is termed trimethylglycine (TMG) for short and has been mentioned above as a betaine compound.

The salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

Solutions Containing N-Alkylated Glycine Derivatives and Sulfone Compounds

1. N-Alkylated Glycine Derivatives

The N-alkylated glycine derivative is an N—$C_{1-6}$ alkyl-, N,N-di($C_{1-6}$ alkyl)- or N,N,N-tri($C_{1-6}$ alkyl)-glycine. The alkyl group is typically a $C_{1-4}$ alkyl group. Preferred alkyl groups are selected from methyl, ethyl, propyl, isopropyl, butyl, isobutyl and tert-butyl. Methyl and ethyl are particularly preferred.

Preferred glycine derivatives for use in the invention are N-methylglycine, N,N-dimethylglycine, N,N,N-trimethylglycine. N-Methyl-glycine is also called sarcosine. N,N-Dimethylglycine is also termed dimethylglycine (DMG) or 2-(dimethylamino)-acetic acid. N,N,N-trimethylglycine is termed trimethylglycine (TMG).

A physiologically acceptable salt or ester of a N-alkylated glycine derivative may be employed. Thus:

The salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

2. Sulfone Compounds

The sulfone compound is a compound of formula (IIC):

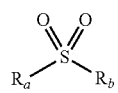

wherein $R_a$ and $R_b$ independently represent $C_{1-6}$ alkyl, for example $C_{1-4}$ alkyl. Preferred alkyl groups are selected from methyl, ethyl, propyl, isopropyl, butyl, isobutyl and tert-butyl. Methyl and ethyl are particularly preferred. A preferred sulfone compound is methylsulfonylmethane (MSM), which is also known as dimethylsulfone ($DMSO_2$).

Sugars

Sugars suitable for use in the present invention include reducing sugars such as glucose, fructose, glyceraldehydes, lactose, arabinose and maltose; and preferably non-reducing sugars such as sucrose and raffinose. The sugar may be a monosaccharide, disaccharide, trisaccharide, or other oligosaccharides. The term "sugar" includes sugar alcohols.

Monosaccharides such as galactose and mannose; disaccharides such as sucrose, lactose and maltose; trisaccharides such as raffinose; and tetrasaccharides such as stachyose are envisaged. Trehalose, umbelliferose, verbascose, isomaltose, cellobiose, maltulose, turanose, melezitose and melibiose are also suitable for use in the present invention. A suitable sugar alcohol is mannitol.

Preservation of viral activity is particularly effective when two or more sugars are used. Two, three or four sugars may be used. Preferably, the two sugars sucrose and raffinose are used. Sucrose is a disaccharide of glucose and fructose. Raffinose is a trisaccharide composed of galactose, fructose and glucose.

Aqueous Solvent

The aqueous solvent is generally water. Pure water such as water for injections is generally used. Alternatively, physiological saline may be used.

Other Components

The aqueous solution may be buffered. Any suitable physiologically acceptable buffer may be used such as a phosphate buffer. Typically, the pH will be adjusted to from 4 to 9, preferably between 5 and 8 and especially from about pH 6.5 to 7.5. The exact pH will depend, for example, on the stability in aqueous solution of the viral particles.

For stability purposes, the solutions of the present invention should be protected from microbial contamination and growth. A preservative may therefore be present, for example in an amount of from 0.001 to 1% by weight. Examples of pharmaceutically acceptable anti-microbial agents that can be used in the formulation include:

quaternary ammonium compounds (e.g. benzalkonium chloride, benzethonium chloride, cetrimide and cetylpyridinium chloride);

mercurial agents (e.g. phenylmercuric nitrate, phenylmercuric acetate and thimerosal);

alcoholic agents (e.g. chlorobutanol, phenylethyl alcohol and benzyl alcohol);

antibacterial esters (e.g. esters of para-hydroxybenzoic acid);

chelating agents such as disodium edetate (EDTA); and other anti-microbial agents such as chlorhexidine, chlorocresol, sorbic acid and its salts and polymyxin.

The presence of a tonicity adjustment agent is sometimes desirable to achieve isotonicity with body fluids resulting in reduced levels of irritancy on administration to a patient. Examples of suitable tonicity adjustment agents are sodium chloride, dextrose and calcium chloride. The isotonicity adjustment agent will desirably be added in a sufficient quantity to achieve this function. Preferably the tonicity adjustment agent is present in an amount of between 0.1 and 10% by weight.

Other additives may be present too such as co-solubilising agents and adjuvants. An adjuvant is generally present when a solution of the invention is used as a vaccine. The adjuvant is used in order to increase potency of the vaccine and/or modulate humoral and cellular immune responses.

Suitable adjuvants include, but are not limited to, mineral salts (e.g., aluminum hydroxide ("alum"), aluminium phosphate, calcium phosphate), particulate adjuvants (e.g., virosomes, ISCOMS (structured complex of saponins and lipids)), microbial derivatives (e.g., MPL (monophosphoryl lipid A), CpG motifs, modified toxins including TLR adjuvants such as flagellin), plant derivatives (e.g., saponins (QS-21)) and endogenous immunostimulatory adjuvants (e.g., cytokines and any other substances that act as immunostimulating agents to enhance the effectiveness of the vaccine).

Production of Solutions of the Invention

Solutions of the invention can be prepared by admixing the viral particles or polypeptide and other ingredients in any convenient order in the selected aqueous solvent. The viral particles or polypeptide are provided in the required amount, for example in a unit dosage amount. A pharmaceutically effective amount of the viral particles or polypeptide can thus be provided in the solution.

Generally, a preparation of the viral particles or polypeptide is admixed with an aqueous solution of the excipient(s) and optionally one or more sugars. The components of the solution may be admixed under sterile conditions. Alternatively, the components of the solution may be first admixed and the resulting solution sterilised. For example, the excipient(s) and/or optional sugars may be added during manufacture of viral particles or polypeptides, so that viral particles or polypeptides are stabilised during manufacture as well as in the final product. In some cases, however, it may be desirable to remove the excipient(s) and/or optional sugars in a purification step prior to formulation of the final product.

The solution with which the viral particles or polypeptide are admixed may be buffered or the solution may be buffered after admixture with the viral particles. It may be a HEPES, phosphate-buffered, Tris-buffered or pure water solution. The pH may be adjusted as desired. Typically, a solution will have a pH of from 4 to 9, preferably from 5 to 8 and especially about pH 6.5 to 7.5.

The excipient and, optionally, one or more sugars are present at concentrations which provide solutions of the required storage stability. The excipient may be an excipient of the invention as herein defined. Suitable concentrations can be determined and optimised by routine experimentation. The concentrations used in a particular instance will depend on a number of factors including:

the particular viral particles or polypeptide;

the excipient that is being used;

whether one or more sugars is present and, if so, the identity of the or each sugar.

The excipient and sugar(s) can be present in amounts that result in synergy interactions between the excipient and the sugar(s). For example, synergistic interactions may arise between (a) sulfones such as MSM and raffinose, and (b) N,N-dialkylglcycines such as DMG and sucrose. Suitable concentrations can be determined and optimised by routine experimentation.

In general terms, however, the concentration of PEI is in the range of 20 µM or less or preferably 15 µM or less based on $M_n$. The PEI concentration may be 10 µM or less based on $M_w$. Such concentrations of PEI are particularly effective at preserving biological activity.

In a preferred embodiment of the invention, the PEI is provided at a concentration based on $M_n$ of less than 5 µM, less than 500 nM, less than 400 nM, less than 300 nM, less than 200 nM, less than 100 nM, less than 40 nM, less than 25 nM, less than 10 nM, less than 5 nM, less than 1 nM, less than 0.5 nM, less than 0.25 nM, less than 0.1 nM, less than 0.075 nM, less than 0.05 nM, less than 0.025 Nm or less than 0.0025 nM. Typically the PEI concentration based on $M_n$ is 0.0025 nM or more, 0.025 nM or more, or 0.1 nM or more. A suitable PEI concentration range based on $M_n$ is between 0.0025 nM and 5 µM, or between 0.025 and 200 nM. Further preferred concentration ranges are between 0.1 nM and 5 µM and between 0.1 nM and 200 nM.

Preferably, the PEI concentration based on $M_w$ is less than 5 µM, less than 1 µM, less than 500 nM, less than 400 nM, less than 300 nM, less than 200 nM, less than 0.1 µM, less than 0.01 µM, less than 5 nM, less than 4 nM, less than 2 nM, less than 1 nM, less than 0.5 nM, less than 0.25 nM, less than 0.1 nM, less than 0.05 nM, less than 0.02 nM, less than 0.002 nM or less than 0.1 nM. Typically the PEI concentration based on $M_w$ is 0.00001 nM or more, 0.001 nM or more or 0.01 nM or more. A suitable PEI concentration range based on $M_w$ is between 0.00001 and 20 nM, between 0.0001 and 20 nM or between 0.0001 and 5 nM.

In some cases it is found that relatively high molecular weight PEI is effective at lower concentrations than relatively low molecular weight PEI. Thus:

Where a relatively high $M_w$ PEI is used, for example in the range of 20 to 1000 kDa, a concentration of PEI of between 0.001 and 500 nM, or 0.001 and 400 nM, or 0.001 and 300 nM, or 0.001 and 200 nM, or 0.001 and 100 nM, or 0.001 and 50 nM, or 0.001 and 5 nM based on $M_w$ is preferred. Where a relatively low $M_w$ PEI is used, for example in the range of 300 Da to 10 kDa, a concentration of PEI of between 0.0001 and 10 µM is preferred.

Where a relatively high $M_n$ PEI is used, for example in the range of 20 to 1000 kDa, the concentration of PEI based on $M_n$ is preferably between 0.001 and 500 nM, or 0.001 and 400 nM, or 0.001 and 300 nM, or 0.001 and 200 nM, or 0.001 and 100 nM, or 0.001 and 50 nM. Where a relatively low $M_n$, is used, for example in the range of 1 Da to 10 kDa, a concentration of PEI of between 0.0001 and 10 µM is used.

The concentration of a compound of formula (I) or physiologically acceptable salt or ester thereof or compound of formula (II) or physiologically acceptable salt or ester thereof in the aqueous solution is generally in the range of from 0.001M to 2.5M and more especially from 0.01M to 2.5M. For example, the concentration range may be from 0.1M to 2.5M. The particular concentration of compound of formula (I) or physiologically acceptable salt or ester thereof or compound of formula (II) or physiologically acceptable salt or ester thereof that is employed will depend on several factors including the viral particles or polypeptide; the particular compound of formula (I) or physiologically acceptable salt or ester thereof or compound of formula (II) or physiologically acceptable salt or ester thereof being used; whether one, two or more sugars are present and the identity of the sugar(s). Thus:

The concentration of a compound of formula (II) in which X represents —S(O)$_2$— or a compound of formula (IIA), such as MSM, or a physiologically acceptable salt or ester thereof is preferably from 0.2 mM to 1M such as from 0.35 mM to 1M, from 3.5 mM to 0.5M, from 0.035M to 0.5M or from 0.035M to 0.25M.

The concentration of a compound of formula (I) or a compound of formula (IA) or formula (IB), such as TMG, or a physiologically acceptable salt or ester thereof is preferably from 0.01M to 2M such as from 0.07M to 2M, from 0.2M to 1.5M, from 0.23M to 1.5M or from 0.07M to 0.7M.

The concentration of a compound of formula (II) in which X represents —S$^+$(R$_c$)— or a compound of formula (IIB), such as S-methyl-L-methionine, or a physiologically acceptable salt or ester thereof is preferably from 0.005M to 2M such as from 0.007M to 2M, from 0.02M to 2M, from 0.023M to 1.5M or from 0.07M to 1M.

The concentration of an N-alkyl-, N,N-dialkyl- or N,N,N-trialkyl-glycine or a physiologically acceptable salt or ester thereof in the aqueous solution is generally in the range of 0.1 mM to 3M or from 1 mM to 2M. The concentration may be from 1 mM to 1.5M or from 5 mM to 1M. Preferred concentrations are from 7 mM to 1.5M or from 0.07M to 0.7M. The particular concentration of an N-alkyl-, N,N-dialkyl- or N,N,N-trialkyl-glycine or a physiologically acceptable salt or ester thereof that is employed will depend on a number of factors including the viral particles or polypeptide; whether one or more sugars is used and, if so, the particular type of sugar(s) used. Thus:

Preferred concentrations of the N-alkyl-, N,N-dialkyl- or N,N,N-trialkyl-glycine or a physiologically acceptable salt or ester thereof when no sugar is present are from 5 mM to 1.5M or from 7 mM to 1M or to 0.7M. More preferred concentrations are from 0.023M to 0.7M, or from 0.07M to 0.7M, such as about 0.07M.

Preferred concentrations of an N-alkyl-, N,N-dialkyl- or N,N,N-trialkyl-glycine or a physiologically acceptable salt or ester thereof when one or more sugars are present are generally lower and in the range of from 1 mM to 1M or from 5 mM to 1M. More preferred concentrations are from 0.007M to 0.7M such as about 0.007M.

When the solution contains an N-alkylated glycine derivative or salt or ester thereof, a sulfone compound of formula (IIC) and, optionally, one or more sugars, the components are present at concentrations which provide solutions of the required storage stability. Suitable concentrations can be determined and optimised by routine experimentation. The N-alkylated glycine derivative or salt or ester thereof and the sulfone compound of formula (IIC) can thus be present in amounts that result in synergy. The concentrations used in a particular instance will depend on a number of factors including:

the particular viral particles to be stabilised;
the excipient that is being used;
whether one or more sugars is present and, if so, the identity of the or each sugar.

In particular:
the concentration of the N-alkylated glycine derivative or salt or ester thereof in the aqueous solution for drying is generally in the range of 0.1 mM to 3M or from 1 mM to 2M. The concentration may be from 1 mM to 1.5M or from 5 mM to 1M. Preferred concentrations are from 7 mM to 1.5M, from 0.07M to 0.7M, 0.1M to 1.5M or from 0.5M to 1.25M, and/or the concentration of the sulfone compound of formula (IIC) in the aqueous solution for drying is generally in the range of 0.1 mM to 3M, from 1 mM to 2M or from 0.2 mM to 1M such as from 0.35 mM to 1M, from 3.5 mM to 0.5M, from 0.035M to 0.5M or from 0.035M to 0.25M. The concentration may be from 0.1M to 1.5M or from 0.5M to 1.25M.

When present in the solutions of the invention, the concentration of sugar or the total concentration of sugars is at least 0.01M, typically up to saturation. Generally the sugar concentration is at least 0.1M, at least 0.2M or at least 0.5M up to saturation e.g. saturation at room temperature or up to 3M, 2.5M or 2M. The sugar concentration may therefore range from, for example, 0.1M to 3M or 0.2M to 2M. Alternatively, the sugar concentration or the total sugar concentration if more than one sugar is present may therefore range from 0.08M to 3M, from 0.15M to 2M or from 0.2M to 1M. A suitable range is from 0.05 to 1M.

When more than one sugar is present in the solutions of the invention, preferably one of those sugars is sucrose. The sucrose may be present at a concentration of from 0.05M, 0.1M, 0.25M or 0.5M up to saturation e.g. saturation at room temperature or up to 3M, 2.5M or 2M.

The ratio of the molar concentration of sucrose relative to the molar concentration of the other sugar(s) is typically from 1:1 to 20:1 such as from 5:1 to 15:1. In the case when two sugars are present and in particular when sucrose and raffinose are present, therefore, the ratio of molar concentrations of sucrose is typically from 1:1 to 20:1 such as from 5:1 to 15:1 and preferably about 10:1.

Particularly preferred solutions contain the following components:
  Sucrose at a concentration of 0.8M to 1.2M, for example about 1M; TMG at a concentration of 0.8 to 1.2M, for example about 1M; and/or raffinose at a concentration of 200 to 400 mM, for example about 300 mM. Typically such a solution comprises MVA.
  Sucrose at a concentration of 0.25 to 1.5M and/or PEI at a concentration of 0.1 to 1000 nM. Typically such a solution comprises adenovirus.
  Sucrose at a concentration of 0.25 to 1.5M, for example about 0.85M; PEI at a concentration of 0.1 to 1000 nM, for example about 0.55 nM; and/or raffinose at a concentration of up to 500 mM, for example about 250 mM. Typically such a solution comprises adenovirus.
  Sucrose at a concentration of 0.8M to 1.2M, for example about 1M; and/or MSM at a concentration of 0.75 to 1.15M, for example about 0.95M. At these concentrations a synergistic interaction between MSM and sucrose may arise. Typically such a solution comprises adenovirus.
  Sucrose at a concentration of 0.3M to 0.7M, for example about 0.5M; DMG at a concentration of 0.2 to 0.6M, for example about 0.4M; and/or raffinose at a concentration of 200 to 400 mM, for example about 275 mM. At these concentrations a synergistic interaction between DMG and raffinose may arise. Typically such a solution comprises adenovirus.

The pH of a solution of the invention may be adjusted as desired. Typically, a solution will have a pH of from 4 to 9, preferably from 5 to 8 and especially about pH 6.5 to 7.5.

A solution of the invention is pyrogen-free. The solution is thus sterilised. A solution can be sterilised by passing it through a sterilising filter. The sterilised solution can then be introduced into containers, such as vials, which are then hermetically sealed. Alternatively, sterilisation can take place e.g. by autoclaving after the solution has been sealed in a container.

The solution can thus be provided in a sealed vial, ampoule, syringe, cartridge, flexible bag or glass bottle. As a small volume parenteral (SVP), it may be provided in a disposable cartridge, disposable syringe, vial, ampoule or flexible bag. As a large volume parenteral (LVP), it may be provided in a vial, flexible bag, glass bottle or, in some cases, as a disposable syringe.

Preferably the containers are vials with non-reactive stoppers. The stopper may be Teflon™-coated or -faced. Silicone rubber stoppers or other non-reactive stoppers are contemplated.

Cartridges, syringes, vials and ampoules are usually composed of Type I or II glass, or polypropylene. Flexible bags are typically constructed with multilayered plastic. Stoppers and septa in cartridges, syringes, and vials are typically composed of elastomeric materials. The input (medication) and output (administration) ports for flexible bags may be plastic and/or elastomeric materials. An overwrap may be used with flexible bags to retard solvent loss and to protect the flexible packaging system from rough handling.

The solutions of the invention can be used as desired, depending upon the viral particles or polypeptide in solution. The solution can be withdrawn from a sealed container e.g. by a syringe and injected into a patient by a suitable route. The solution may thus be administered by subcutaneous, intramuscular, intravenous or intraperitoneal injection. A solution may alternatively be administered by infusion. The solution may be diluted prior to administration.

Preservation of Viral Particles or Polypeptides During Manufacture

In some circumstances, it may be desirable to use the excipient of the invention during manufacturing of a solution of viral particles or polypeptides, in order that the viral particles or polypeptides are preserved or stabilised during the manufacturing process. This can increase the yield of the process.

Typically, the excipient of the invention will be retained in the solution of viral particles or polypeptides and thereby in the final product. This can be advantageous since the excipient of the invention will continue to stabilise the viral particles or polypeptides in the final product.

Alternatively, there may be some situations in which it is preferable to remove the excipient of the invention in a purification step. Such removal can be carried out by any suitable purification technique known to those skilled in the art, such as chromatography. The exact purification method will depend on the excipient being used and suitable techniques can be readily selected by those skilled in the art.

Once the excipient has been removed, the solution of viral particles or polypeptides is typically sealed in a container, such as vial, ampoule, syringe, cartridge, flexible bag or glass bottle.

Preferably the solution is sterilised, for example by passing the solution through a sterilising filter, prior to introducing the solution into the container. Alternatively, it may be preferable to perform the manufacturing process and purification under sterile conditions, such that the end product is sterile.

The concentration of the excipient of the invention is preferably as set out above under "Production of Solutions of the Invention" above. The concentration of the sugar(s), where present, is also preferably as set out under "Production of Solutions of the Invention" above.

Preservation of Samples Taken from a Human or Animal

Samples taken from a human or animal can be preserved by an excipient of the invention and optionally one or more sugars. When a sample is taken from a human or animal, it often necessary to transport that sample to another location where it can be assayed or tested. Degradation of the sample generally occurs during transport, even when the sample is frozen or refrigerated. This can lead to negative or poor results in assays and tests on the sample.

The presence of an excipient of the invention and optionally one or more sugars in a solution of a sample taken from a human or animal generally preserves the sample.

The invention is typically carried out in vitro on a sample obtained from the human or animal. The sample typically comprises a body fluid of the human or animal. The sample is preferably a blood, plasma, serum, urine, cerebrospinal fluid or joint fluid sample. The sample is most preferably a blood sample. Samples taken from humans, such as human blood samples are preferred. The sample may be carried on a swab.

The samples taken from a human or animal may be infectious or non-infectious. It is particularly preferable to preserve infectious samples comprising viral particles, since the viral particles are preserved by the excipient and optionally one or more sugars.

The sample taken from a human or animal, the excipient of the invention and optionally one or more sugars may be added to an aqueous solution in any convenient order. For example:
the sample may be added to a solution of the excipient and optionally one or more sugars; or
the sample, excipient and optionally one or more sugars may be added simultaneously to an aqueous solution; or
the excipient and optionally one or more sugars may be added to an aqueous solution of the sample.

The concentration of the excipient of the invention is preferably as set out above under "Production of Solutions of the Invention" above. The concentration of the sugar(s), where present, is also preferably as set out under "Production of Solutions of the Invention" above.

The aqueous solution comprising the sample taken from a human or animal, an excipient of the invention and optionally one or more sugars is typically stored in a refrigerator or in a freezer. The temperature of a refrigerator is typically 2 to 8° C., preferably 4 to 6° C., or for example about 4° C. The temperature of a freezer is typically −10 to −80° C., preferably −10 to −30° C., for example about −20° C.

The aqueous solution comprising the sample taken from a human or animal, an excipient of the invention and optionally one or more sugars is typically stored in a sealed container, such as vial, ampoule, syringe, cartridge, flexible bag or glass bottle.

Once the preserved sample reaches the location where it is to be tested or assayed, the sample can generally be tested or assayed without prior removal of the excipient or, where present, sugars.

Measuring Viral Particle Preservation

Preservation in relation to viral particles refers to resistance of the viral particle to physical or chemical degradation and/or loss of biological activity.

Methods of assaying for viral activity such as infectivity and/or immunogenicity are well known to those skilled in the art and include but are not limited to growth of a virus in a cell culture, detection of virus-specific antibody in blood, ability to elicit T and/or B cell responses, detection of viral antigens, detection of virus encoded DNA or RNA, or observation of virus particles using a microscope.

Further, the presence of a virus gives rise to morphological changes in the host cell, which can be measured to give an indication of viral activity. Detectable changes such as these in the host cell due to viral infection are known as cytopathic effect. Cytopathic effects may consist of cell rounding, disorientation, swelling or shrinking, death and detachment from the surface. Many viruses induce apoptosis (programmed cell death) in infected cells, measurable by techniques such as the TUNEL (Terminal uridine deoxynucleotidyl transferase dUTP nick end labelling) assay and other techniques well known to those skilled in the art.

Viruses may also affect the regulation of expression of the host cell genes and these genes can be analysed to give an indication of whether viral activity is present or not. Such techniques may involve the addition of reagents to the cell culture to complete an enzymatic or chemical reaction with a viral expression product. Furthermore, the viral genome may be modified in order to enhance detection of viral infectivity. For example, the viral genome may be genetically modified to express a marker that can be readily detected by phase contrast microscopy, fluorescence microscopy or by radioimaging. The marker may be an expressed fluorescent protein such as GFP (Green Fluorescent Protein) or an expressed enzyme that may be involved in a colourimetric or radiolabelling reaction. The marker could also be a gene product that interrupts or inhibits a particular function of the cells being tested.

An assay for plaque-forming units can be used to measure viral infectivity and to indicate viral titre. In this assay, suitable host cells are grown on a flat surface until they form a monolayer of cells covering a plastic bottle or dish. The selection of a particular host cell will depend on the type of virus. Examples of suitable host cells include but are not limited to CHO, BHK, MDCK, 10T1/2, WEHI cells, COS, BSC 1, BSC 40, BMT 10, VERO, WI38, MRC5, A549, HT1080, 293, B-50, 3T3, NIH3T3, HepG2, Saos-2, Huh7, HEK293 and HeLa cells. The monolayer of host cells is then infected with the viral particles. The liquid medium is replaced with a semi-solid one so that any virus particles produced, as the result of an infection cannot move far from the site of their production. A plaque is produced when a virus particle infects a cell, replicates, and then kills that cell. A plaque refers to an area of cells in the monolayer which display a cytopathic effect, e.g. appearing round and darker than other cells under the microscope, or as white spots when visualized by eye; the plaque center may lack cells due to virus-induced lysis. The newly replicated virus infects surrounding cells and they too are killed. This process may be repeated several times. The cells are then stained with a dye such as methylene blue, which stains only living cells. The dead cells in the plaque do not stain and appear as unstained areas on a coloured background.

Each plaque is the result of infection of one cell by one virus followed by replication and spreading of that virus. However, viruses that do not kill cells may not produce plaques. A plaque refers to an area of cells in a monolayer which display a cytopathic effect, e.g. appearing round and darker than other cells under the microscope, or as white spots when visualized by eye; the plaque center may lack cells due to virus-induced lysis. An indication of viral titre is given by measuring "plaque-forming units" (PFU). Levels of viral infectivity can be measured in a sample of biological material preserved according to the present invention and compared to control samples such as freshly harvested virus or samples subjected to desiccation and/or thermal variation without addition of the preservation mixture of the present invention.

Some types of viral particles of the invention, such as viral proteins, VLPs, or some inactivated viruses do not have the ability to form plaques in the plaque assay. In this case, preservation can be measured by other methods such as methods for determining immunogenicity which are well known to those skilled in the art. For example, in vivo and in vitro assays for measuring antibody or cell-mediated host immune responses are known in the art and suitable for use in the present invention. For example, an antibody based immune response may be measured by comparing the amount, avidity and isotype distribution of serum antibodies in an animal model, before and after immunization using the preserved viral particle of the invention.

Uses of the Preserved Viral Particles of the Invention

The solutions of the invention can be used as desired. The solution can be withdrawn from a sealed container e.g. by a syringe and injected into a patient by a suitable route. The solution may thus be administered by subcutaneous, intramuscular, intravenous or intraperitoneal injection. A solution may alternatively be administered by infusion. The solution may be diluted prior to administration.

Vaccines

The solutions of the present invention may find use as vaccines. For example, solutions containing whole killed virus, live attenuated virus, chemically inactivated virus, VLPs or live viral vectors are suitable for use as vaccines. As a vaccine the viral particles may be used as antigens or to encode antigens such as viral proteins for the treatment or prevention of a number of conditions including but not limited to viral infection, sequelae of viral infection including but not limited to viral-induced toxicity, cancer and allergies. Such antigens contain one or more epitopes that will stimulate a host's immune system to generate a humoral and/or cellular antigen-specific response.

A vaccine of the invention may be used to prevent or treat infection by viruses such as human papilloma viruses (HPV), HIV, HSV2/HSV1, influenza virus (types A, B and C), para influenza virus, polio virus, RSV virus, rhinoviruses, rotaviruses, hepatitis A virus, norwalk virus, enteroviruses, astroviruses, measles virus, mumps virus, varicella-zoster virus, cytomegalovirus, epstein-barr virus, adenoviruses, rubella virus, human T-cell lymphoma type I virus (HTLV-I), hepatitis B virus (HBV), hepatitis C virus (HCV), hepatitis D virus, poxvirus and vaccinia virus. The vaccine may further be used to provide a suitable immune response against numerous veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and bovine viral diarrhea virus. In one embodiment, the vaccine is a subunit, conjugate or multivalent vaccine. For example, the vaccine of the invention may be used to treat infection by two or more different types of virus such as measles, mumps and rubella (e.g. MMR vaccine).

To measure the preservation of stability of a vaccine prepared in accordance with the present invention, the potency of the vaccine can be measured using techniques well known to those skilled in the art. For example, the generation of a cellular or humoral immune response can be tested in an appropriate animal model by monitoring the generation of antibodies or immune cell responses to the vaccine. The ability of vaccine samples to trigger an immune response may be compared with vaccines not subjected to the same preservation technique.

Viral Vectors

A virus or viral vector can be used according to the present invention to transfer a heterologous gene or other nucleic acid sequence to target cells. Suitably, the heterologous sequence (i.e. transgene) encodes a protein or gene product which is capable of being expressed in the target cell. Suitable transgenes include desirable reporter genes, therapeutic genes and genes encoding immunogenic polypeptides (for use as vaccines). Gene therapy, an approach for treatment or prevention of diseases associated with defective gene expression, involves the insertion of a therapeutic gene into cells, followed by expression and production of the required proteins. This approach enables replacement of damaged genes or inhibition of expression of undesired genes. In particular, the virus or viral vector may be used in gene therapy to transfer a therapeutic transgene or gene encoding immunogenic polypeptides to a patient.

In a preferred embodiment, the viral particle is a live viral vector. By "live viral vector" is meant a live viral vector that is non-pathogenic or of low pathogenicity for the target species and in which has been inserted one or more genes encoding antigens that stimulate an immune response protective against other viruses or microorganisms, a reporter gene or a therapeutic protein. In particular, nucleic acid is introduced into the viral vector in such a way that it is still able to replicate thereby expressing a polypeptide encoded by the inserted nucleic acid sequence and in the case of a vaccine, eliciting an immune response in the infected host animal. In one embodiment, the live viral vector is an attenuated live viral vector i.e. is modified to be less virulent (disease-causing) than wildtype virus.

The basis of using recombinant viruses as potential vaccines involves the incorporation of specific genes from a pathogenic organism into the genome of a nonpathogenic or attenuated virus. The recombinant virus can then infect specific eukaryotic cells either in vivo or in vitro, and cause them to express the recombinant protein.

Live viral vector vaccines derived by the insertion of genes encoding sequences from disease organisms may be preferred over live attenuated vaccines, inactivated vaccines, subunit or DNA approaches. One of the most important safety features of live viral vectors is that the recipients may be immunized against specific antigens from pathogenic organisms without exposure to the disease agent itself. Safety is further regulated by the selection of a viral vector that is either attenuated for the host or unable to replicate in the host although still able to express the heterologous antigen of interest. A vaccine strain that has a history of safety in the target species offers an additional safety feature. Several systems have been developed in which the vector is deleted of essential genes and preparation of the vaccine is carried out in cell systems that provide the missing function.

A variety of vectors such as retroviral, lentiviral, herpes virus, poxvirus, adenoviral and adeno-associated viral vectors can be used for the delivery of heterologous genes to target cells. The heterologous gene of interest may be inserted into the viral vector. The viral vectors of the invention may comprise for example a virus vector provided with an origin of replication, optionally a promoter for the expression of the heterologous gene and optionally a regulator of the promoter. For example, adenoviruses useful in the practice of the present invention can have deletions in the E1 and/or E3 and/or E4 region, or can otherwise be maximized for receiving heterologous DNA.

The viral vector may comprise a constitutive promoter such as a cytomegalovirus (CMV) promoter, SV40 large T antigen promoter, mouse mammary tumour virus LTR promoter, adenovirus major late promoter (MLP), the mouse mammary tumour virus LTR promoter, the SV40 early promoter, adenovirus promoters such as the adenovirus major late promoter (Ad MLP), HSV promoters (such as the HSV IE promoters), HPV promoters such as the HPV upstream regulatory region (URR) or rous sarcoma virus promoter together with other viral nucleic acid sequences operably linked to the heterologous gene of interest. Tissue-specific or inducible promoters can also be used to control expression of the heterologous gene of interest. Promoters may also be selected to be compatible with the host cell for which expression is designed.

The viral vector may also comprise other transcriptional modulator elements such as enhancers. Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters) and may operate when positioned in either orientation relative to the sequence of interest. Enhancers have been identified from a number of viral sources, including polyoma virus, BK virus, cytomegalovirus (CMV), adenovirus, simian virus 40 (SV40), Moloney sarcoma virus, bovine papilloma virus and Rous sarcoma virus. Examples of suitable enhancers include the SV40 early gene enhancer, the enhancer/promoter derived from the long terminal repeat (LTR) of the Rous Sarcoma Virus, and elements derived from human or murine CMV, for example, elements included in the CMV intron A sequence.

The viral vector containing a heterologous gene of interest may then be preserved according to the method of the invention before storage, subjecting to further preservation techniques such as lyophilisation, or administration to a patient or host cell.

Nucleic acids encoding for polypeptides known to display antiviral activity, immunomodulatory molecules such as cytokines (e.g. TNF-alpha, interleukins such as IL-6, and IL-2, interferons, colony stimulating factors such as GM-CSF), adjuvants and co-stimulatory and accessory molecules may be included in the viral vector of the invention. Alternatively, such polypeptides may be provided separately, for example in the preservation mixture of the invention or may be administered simultaneously, sequentially or separately with viral vectors of the invention.

Preferably, the preserved viral vector of the invention may be introduced into suitable host cells using a variety of viral techniques that are known in the art, such as for example infection with recombinant viral vectors such as retroviruses, herpes simplex virus and adenoviruses. Preferably, administration of the preserved viral vector of the invention containing a gene of interest is mediated by viral infection of a target cell.

A number of viral based systems have been developed for transfecting mammalian cells.

For example, a selected recombinant nucleic acid molecule can be inserted into a vector and packaged as retroviral particles using techniques known in the art. The recombinant virus can then be isolated and delivered to cells of the subject either in vivo or ex vivo. Retroviral vectors may be based upon the Moloney murine leukaemia virus (Mo-MLV). In a retroviral vector, one or more of the viral genes (gag, pol & env) are generally replaced with the gene of interest.

A number of adenovirus vectors are known. Adenovirus subgroup C serotypes 2 and 5 are commonly used as vectors. The adenovirus may be a human or non-human adenovirus. The wild type adenovirus genome is approximately 35 kb of which up to 30 kb can be replaced with foreign DNA.

There are four early transcriptional units (E1, E2, E3 & E4), which have regulatory functions, and a late transcript, which codes for structural proteins. Adenovirus vectors may have the E1 and/or E3 gene inactivated. The missing gene(s) may then be supplied in trans either by a helper virus, plasmid or integrated into a helper cell genome. Adenovirus vectors may use an E2a temperature sensitive mutant or an E4 deletion. Minimal adenovirus vectors may contain only the inverted terminal repeats (ITRs) & a packaging sequence around the transgene, all the necessary viral genes being provided in trans by a helper virus. Suitable adenoviral vectors thus include Ad4, Ad5, Ad7, Ad11, Ad14, Ad26, Ad35 and Ad36 vectors and simian adenovirus vectors, preferably Ad4, Ad5, Ad7, Ad35 and Ad36 vectors. Ad5 is most commonly used.

Viral vectors may also be derived from the pox family of viruses, including vaccinia viruses and avian poxvirus such as fowlpox vaccines. For example, modified vaccinia virus Ankara (MVA) is a strain of vaccinia virus which does not replicate in most cell types, including normal human tissues. A recombinant MVA vector may therefore be used to deliver the polypeptide of the invention.

Addition types of virus such as adeno-associated virus (AAV) and herpes simplex virus (HSV) may also be used to develop suitable vector systems Administration Solutions according to the present invention may be administered to a subject in vivo using a variety of known routes and techniques. The solutions are suitable for parenteral administration. For example, the vaccines can be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. Vaccines may be administered topically to skin or mucosal tissue, such as nasally, intratrachealy, intestinal, sublingually, rectally or vaginally, or provided as a finely divided spray suitable for respiratory or pulmonary administration.

The following Examples illustrate the invention.

Statistics

In some of the Examples, the following statistical values were calculated:

$R^2$=coefficient of determination. A measure of goodness of fit. $R^2<0.5$=low model significance.

$Q^2$=estimate of prediction precision. A measure of goodness of prediction.

$Q^2$ should be $>0.1$ for a significant model. $Q^2$ should be $>0.5$ for a good model. $R^2$-$Q^2<0.2$ to $0.3$ Model validity (MV)="a test of diverse model problems". Model validity<0.25=indicator of statistically significant model problems e.g. outliers, incorrect model/transformation.

Reproducibility (Rep)=measure of variation between replicates compared to overall variability. Reproducibility>0.5 implies significance.

The following materials, equipment and techniques were employed unless stated otherwise in Examples 1 to 4:

Materials

HEK-293 cells (ECACC 85120602)
DMSO (Sigma D1435, Lot 118K1455)
Sucrose (Sigma 16104, Lot 70040)
Raffinose (Sigma R0250, Lot 039K0016)
PBS (Sigma D8662, Lot 118K2339)
Water (Sigma W3500, Lot 8M0411)
5 ml glass vials (Adelphi Tubes VCD005)
2 ml glass vials (Adelphi Tubes VCDIN2R)
14 mm freeze drying stoppers (Adelphi Tubes FDIA14WG/B)
14 mm caps (Adelphi Tubes CWPP14)
Adenovirus GFP (Vector Biolabs cat. 1060)
Glycine (Sigma, G7126, 118K00181)
N,N-DMG (Sigma D1156, Lot 077K1856)
SMM (Sigma, 64382, 1339210)

TMG (Sigma, B2629, 1089K1201)
Equipment
Modulyo D Freeze Dryer (Thermofisher)
HERA safe class II cabinet (Thermofisher)
Binder $CO_2$ Incubator (Binder)
Binder APT line TM MK thermocycling test chamber (Binder)
Thermo Scientific MaxQ 4450 Incubator (Thermofisher)
KERN EW220-3NM balance (VWR)
Elcold −45° C. freezer (VWR)
Forma 900 series −80° C. freezer (Thermofisher)
Synergy HT microplate reader (Biotek)

Example 1

Sample Preparation

The loading times of vials prior to freeze drying may impact viral recovery and vaccines efficacy as long fill times can increase variation of the batch. Excipients were tested with sugars only or a combination of and sugars and PEI to see if they were able to protect virus during a standing period prior to freeze drying. Samples were prepared in 2 ml glass vials in triplicate. Final sugar concentrations were 1M Suc 100 mM Raf. The final PEI concentration was 1 nM. In half the samples adenovirus expressing Green Fluorescent Protein (GFP) was added and left for 4 hours at room temperature. Following incubation adenovirus was added to the remaining vials. Freeze drying was carried out using a Modulyo D Freeze Dryer for 3 days where the condenser was set to −80° C. and the vacuum was 200 mTorr. Following completion of the freeze drying vials were stoppered.
Determination of Adenovirus Titre
Virus titre was calculated by infecting cells with the adenovirus expressing GFP. 96 flat bottomed cell culture dishes (Jencons, UK) were seeded with HEK 293 cells (ECACC 85120602) at $10^5$ cells per ml (100 μl per well) and maintained at 37° C. with 5% $CO_2$. After achieving 90% confluence, vials containing the adenovirus plus excipient were reconstituted in 1 ml of Dulbecco's Minimum Essential Medium (DMEM) plus 5% Foetal Bovine Serum (FBS). A 1:10 dilution step was then made by taking 100 μl from the reconstituted vial and adding to 900 μl of DMEM. 100 μl of the resulting diluted virus was then added to the first row on the plate and a 1:2 dilution carried out down the plate. The process was repeated with the next excipient. After a further 48 hours, the number of GFP expressing cells per well was counted using fluorescent microscopy. Plaque-forming unit (PFU) per ml was calculated from the number of GFP expressing cells multiplied by the dilution. Significance between viral preparations was determined using Prism graphpad with a one way ANOVA followed by a turkey post test. **=P<0.01.
Results and Discussion
The experiment in this Example investigated whether PEI and sugars enhance virus stability in a liquid prior to freeze drying. A mixture of adenovirus, sugars and PEI or adenovirus and sugars were incubated for 4 hours prior to freeze drying and compared to samples prepared and immediately freeze dried. The results demonstrated that in virus only controls, there was a complete loss of adenovirus in both samples that were incubated for 4 hours prior to freeze drying and samples that were immediately freeze dried (FIG. 1). In sugar only samples, although virus titre was higher than in the virus only controls, there was a significant loss of virus titre following the 4 hour incubation compared to sugar excipients that were immediately freeze dried. In the sugar PEI samples, there was no significant loss in virus following 4 hours incubation at room temperature compared to sugar PEI concentrations that were immediately freeze dried. The results demonstrate a benefit of having a combination of sugars and PEI in stabilising a virus prior to freeze drying.

Example 2

250 μl of each excipient and 50 μl of adenovirus was added to each vial to give a range of final concentrations of PEI (see Table 1 below). After vortexing, glass vials were placed in a 37° C. incubator for 1 week. Following incubation, virus titre was determined using the adenovirus GFP assay as set out above.

TABLE 1

| | Vial ID | | | | |
|---|---|---|---|---|---|
| | 1, 2 | 3, 4 | 5, 6 | 7, 8 | 9, 10 |
| Excipient concentration | PBS | 1M Suc 100 mM Raf 13 μM PEI | 1M Suc 100 mM Raf 2.6 μM PEI | 1M Suc 100 mM Raf 0.26 μM PEI | 1M Suc 100 mM Raf 0.026 μM PEI |

Figure 2:
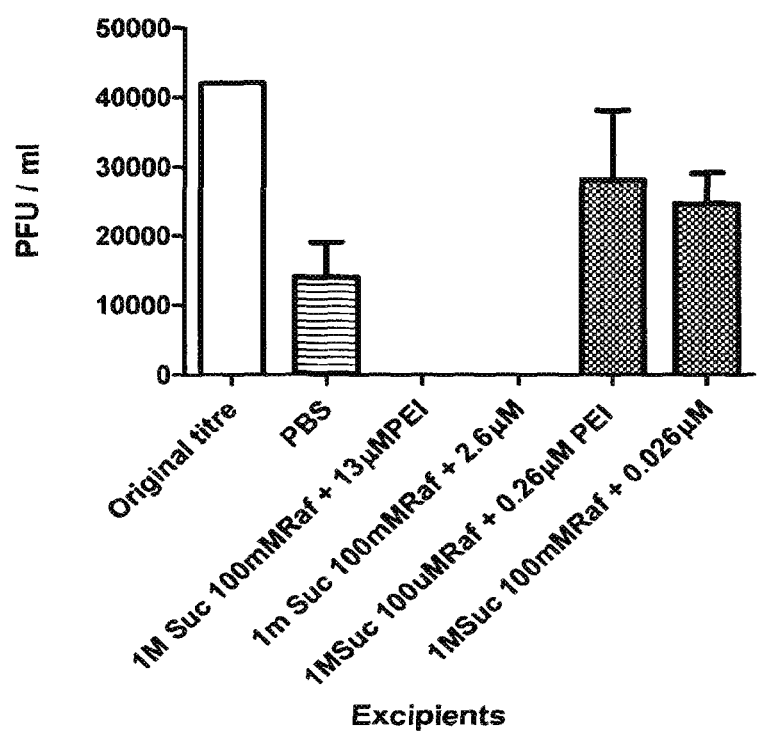
FIG. 2 shows the results of an experiment investigating liquid stability of adenovirus following heat challenge at 37° C. for one week.

Results and Discussion
The experiment in this Example examined stability of adenovirus in an aqueous solution following heat challenge at 37° C. for 1 week. PBS controls showed a significant loss in titre whereas sugars plus PEI at 0.26 μM showed good preservation of the adenovirus following heat challenge (see FIG. 2). The upper limit of PEI concentrations appeared to be 2.6 μM as above this concentration no virus infectivity was seen.

Example 3

Sample Preparation

1×57 μg reference vial of inactivated influenza H1N1 Solomon Islands (NIBSC) was reconstituted with 475 μl sterile distilled water to give an hemagglutinin (HA) concentration of 120 μg/ml. This solution was then further diluted 1/6 into water, PBS and an excipient solution comprising sucrose/raffinose/polyethyleneimine yielding final concentrations of 1M sucrose/100 mM raffinose/1.6 μM PEI and 20 μg/ml HA in PBS. Replicate samples of PBS and excipient solutions were placed at −20° C., +4° C. and +45° C. whilst the $H_2O$ sample was maintained at the recommended storage temperature of +4° C. All samples were maintained at these temperatures for 5 days.

After incubation aliquots of all samples, along with a freshly water-reconstituted standard reference vial, were assayed by ELISA (solid bars in FIG. 3). Remaining samples were refrigerated at +4° C. and re-assayed 1 month later along with another freshly reconstituted standard reference sample (hatched bars in FIG. 3).

ELISA Protocol

Samples were diluted 1/20 to give HA concentration of 1 μg/ml in PBS. 50 μl volumes of each solution were used to coat 6 replicate wells of an ELISA plate (Nunc maxisorb) which was then incubated at 37° C. for 1 hour prior to washing ×3 in PBS.

A monospecific polyclonal sheep anti H1 Solomon Islands (NIBSC) was diluted 1/200 in a blocking buffer comprising PBS/0.1% Tween20/5% non-fat dried milk powder (PBS™). 50 μl volumes were added to each assay well and the plate was incubated at 37° C. for 1 hour. The plate was washed ×3 PBS and 50 μl of a 1/1000 dilution in PBS™ of a horse radish peroxidase conjugated polyclonal rabbit anti sheep immunoglobulins (Abcam) was added per well. The plate was incubated for a further 1 hour at 37° C. prior to washing ×4 with PBS.

The assay was developed by the addition of 50 μl/well of a substrate/chromogen solution comprising 0.4 μl/ml of a 30% $H_2O_2$ solution (Sigma) and 0.4 mg/ml O-phenylenediamine (OPD) (Sigma) in 0.05M citrate/phosphate buffer pH 5.0. The plate was incubated at room temperature for 10 minutes. The reaction was stopped by the addition of 50 μl/well of 1M $H_2SO_4$. The plate was read on a Synergy HT microplate reader (Biotek) with a 490 nm interference filter.

Results and Discussion

Figure 3:
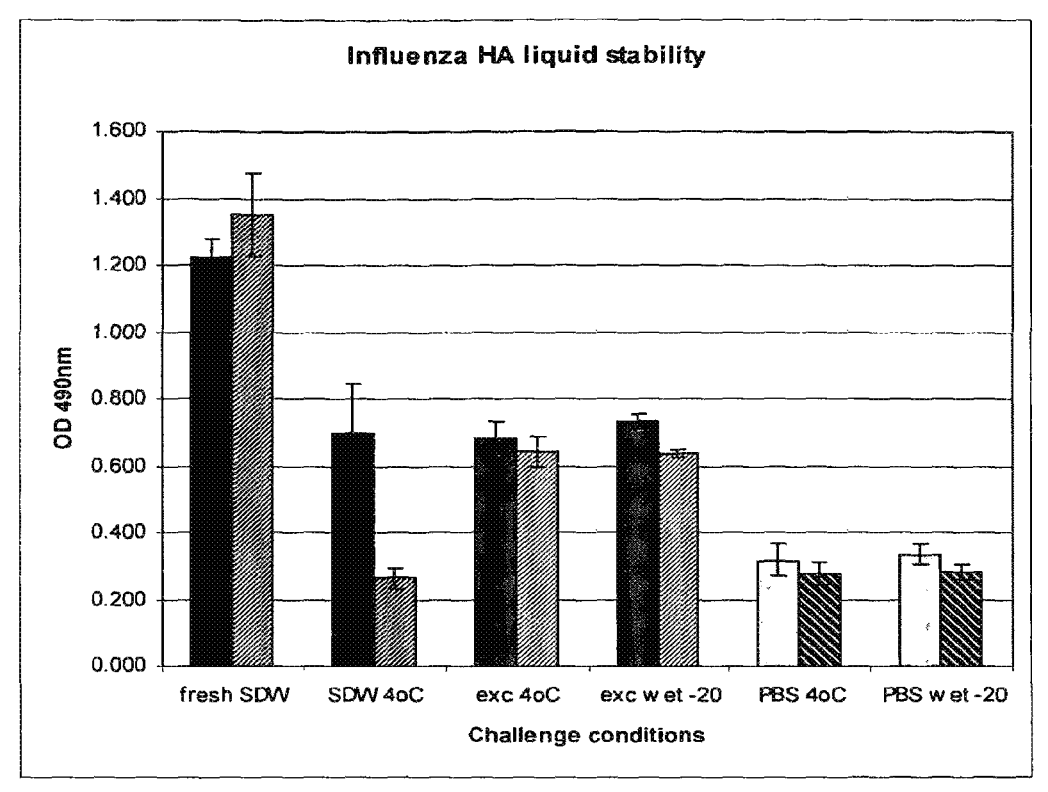

There is a substantial loss of recognition following a five day incubation period at both +4° C. and −20° C. for HA solubilised in water, PBS or the excipient mixture analysed, with HA in PBS showing the greatest deterioration (see FIG. 3).

The excipient composition shows similar results to the water composition (which is the recommended storage medium) after 5 days incubation, however, following a further months incubation at +4° C., recognition of the excipient composition is substantially better than that of the water composition with very little, if any, further deterioration. Further, there is little difference between the +4° C. maintained and −20° C. freeze-thawed excipient compositions. The freeze-thawing of influenza virus HA is not recommended (and hence was not included for the water composition in this experiment) as aggregation is known to occur.

Example 4

Virus Formulation

Recombinant adenovirus (Vector Biolabs) expressing enhanced GFP (Green Fluorescent Protein) under a CMV promoter was used for ease of detection during assay.

In this study four glycinergic compounds and one therein were each tested for efficacy as a preservative (of adenovirus) at a final concentration of 0.07-0.70M, both in co-formulations with sugars (1M Sucrose, 100 mM Raffinose) and in their absence. The glycinergic compounds tested were Glycine, Sarcosine (mono-methyl glycine), DMG (Di-methyl glycine), TMG (Tri-Methyl glycine). The Thetin tested was SMM (S-methyl-methionine). Virus was formulated with excipient mixtures in order to test their efficacy in preserving viral activity through a period of thermal challenge. Each mixture of excipients plus virus (see Table 2 below) was made up as a stock in PBS and 300 μl added to appropriately labelled 5 ml glass vials.

TABLE 2

Summary of treatments, each setup in triplicate. Y = Yes, N = No. Where sugars present concentration = 1M Sucrose, 100 mM Raffinose.

| Excipient | Conc. (M) | Sugars? | Thermal Challenge (° C.) | Excipient | Conc. (M) | Sugars? | Thermal Challenge (° C.) |
|---|---|---|---|---|---|---|---|
| DMG | 0.70 | Y | 4 | DMG | 0.7 | Y | 37 |
| DMG | 0.23 | Y | 4 | DMG | 0.23 | Y | 37 |
| DMG | 0.07 | Y | 4 | DMG | 0.07 | Y | 37 |
| DMG | 0.70 | N | 4 | DMG | 0.70 | N | 37 |
| DMG | 0.23 | N | 4 | DMG | 0.23 | N | 37 |
| DMG | 0.07 | N | 4 | DMG | 0.07 | N | 37 |
| Glycine | 0.70 | Y | 4 | Glycine | 0.70 | Y | 37 |
| Glycine | 0.23 | Y | 4 | Glycine | 0.23 | Y | 37 |
| Glycine | 0.07 | Y | 4 | Glycine | 0.07 | Y | 37 |
| Glycine | 0.70 | N | 4 | Glycine | 0.70 | N | 37 |
| Glycine | 0.23 | N | 4 | Glycine | 0.23 | N | 37 |
| Glycine | 0.07 | N | 4 | Glycine | 0.07 | N | 37 |
| Sarcosine | 0.70 | Y | 4 | Sarcosine | 0.70 | Y | 37 |
| Sarcosine | 0.23 | Y | 4 | Sarcosine | 0.23 | Y | 37 |
| Sarcosine | 0.07 | Y | 4 | Sarcosine | 0.07 | Y | 37 |
| Sarcosine | 0.70 | N | 4 | Sarcosine | 0.70 | N | 37 |
| Sarcosine | 0.23 | N | 4 | Sarcosine | 0.23 | N | 37 |
| Sarcosine | 0.07 | N | 4 | Sarcosine | 0.07 | N | 37 |
| TMG | 0.70 | Y | 4 | TMG | 0.70 | N | 37 |
| TMG | 0.23 | Y | 4 | TMG | 0.23 | Y | 37 |
| TMG | 0.07 | Y | 4 | TMG | 0.07 | Y | 37 |
| TMG | 0.70 | N | 4 | TMG | 0.70 | N | 37 |
| TMG | 0.23 | N | 4 | TMG | 0.23 | N | 37 |
| TMG | 0.07 | N | 4 | TMG | 0.07 | N | 37 |
| SMM | 0.70 | Y | 4 | SMM | 0.70 | Y | 37 |
| SMM | 0.23 | Y | 4 | SMM | 0.23 | Y | 37 |
| SMM | 0.07 | Y | 4 | SMM | 0.07 | Y | 37 |
| SMM | 0.70 | N | 4 | SMM | 0.70 | N | 37 |
| SMM | 0.23 | N | 4 | SMM | 0.23 | N | 37 |
| SMM | 0.07 | N | 4 | SMM | 0.07 | N | 37 |
| None | 0.00 | Y | 4 | None | 0.00 | Y | 37 |
| None | 0.00 | N | 4 | None | 0.00 | N | 37 |

Thermal Challenge Three replicates of each treatment were placed at 4° C., and a further 3 at 37° C., for a period of 7 days. At this time all samples were placed at 4° C. until it was practical to assay them.

Adenovirus Assay

Cells permissive to the Adenovirus (HEK 293, ECACC 85120602) were seeded into 96-well-flat-bottomed cell culture dishes (VWR, UK) at $10^5$ cells per ml (100 µl per well) and maintained at 37° C. with 5% $CO_2$. After achieving 90% confluence, vials containing the adenovirus plus excipient were removed from the fridge and 1 in 10, and 1 in 100 dilutions produced by serial dilution in DMEM. 100 µl of each of the resultant dilutions (1 in 10 and 1 in 100) was then added wells of the plate containing HEK 293 cells. Additionally, a further sample of adenovirus, from the same source and with the same titre (on storage at −80° C.) used in the excipient treatments, was thawed and used to produce a 1 in 10 dilution series (in DMEM). Dilutions ranging from 1 in 10 to 1 in $10^6$ were also added to individual wells containing HEK 293s. At 48 hours, post inoculation the number of GFP (Green Fluorescent Protein) cells per well were counted using fluorescent microscopy, and this was subsequently converted to pfu/ml of the treated samples taking into account the volume applied and dilution of the inoculum.

Results and Discussion

Figure 4A:
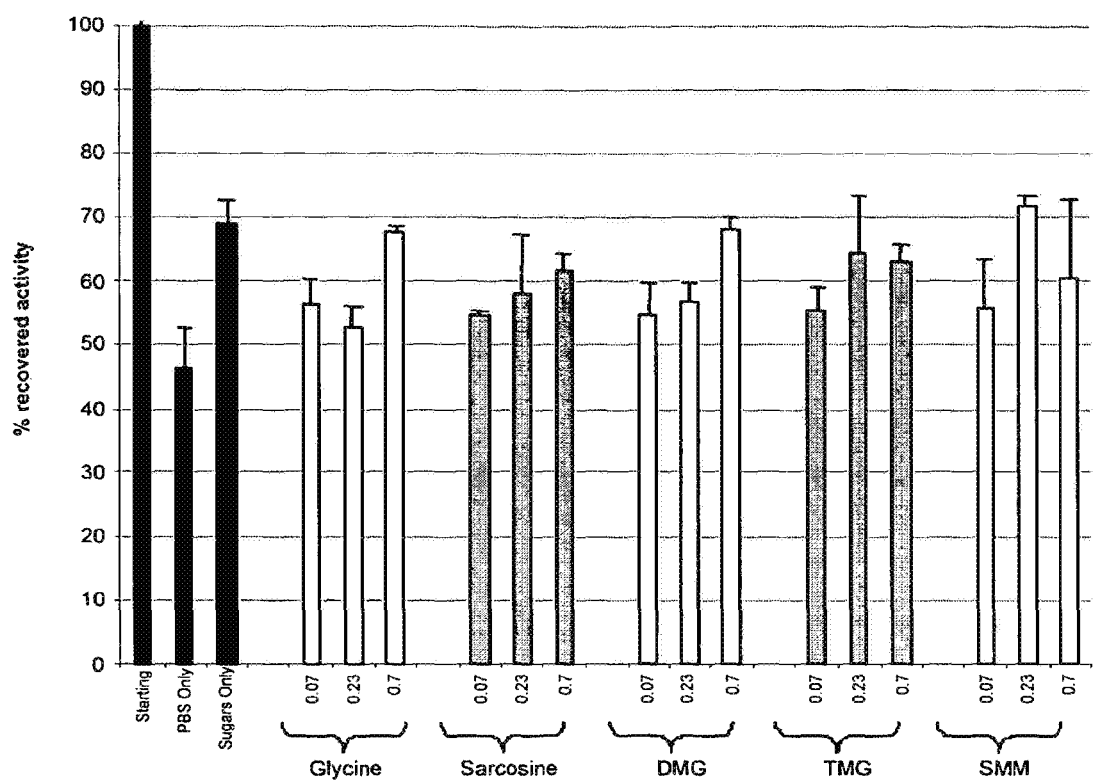
FIG. 4A shows the effect of test formulations on the recovered activity of formulations of adenovirus held at 4° C. for one week. Grey and white bars represent test formulations. Figures on the x-axis refer to concentration in M. Black bars represent control samples. "Starting"=titre of input virus for storage, "PBS"=formulation containing no further excipient, "sugars"=formulation comprising 1M sucrose, 100 mM raffinose. Error bars=standard of the mean, n=3.

Recovered Viral Activity after 1 Week at 4° C. (FIGS. 4a & b) (Glycinergics and SMM WITHOUT Added Sugar or WITH Added Sugar Respectively)

Figure 4B:
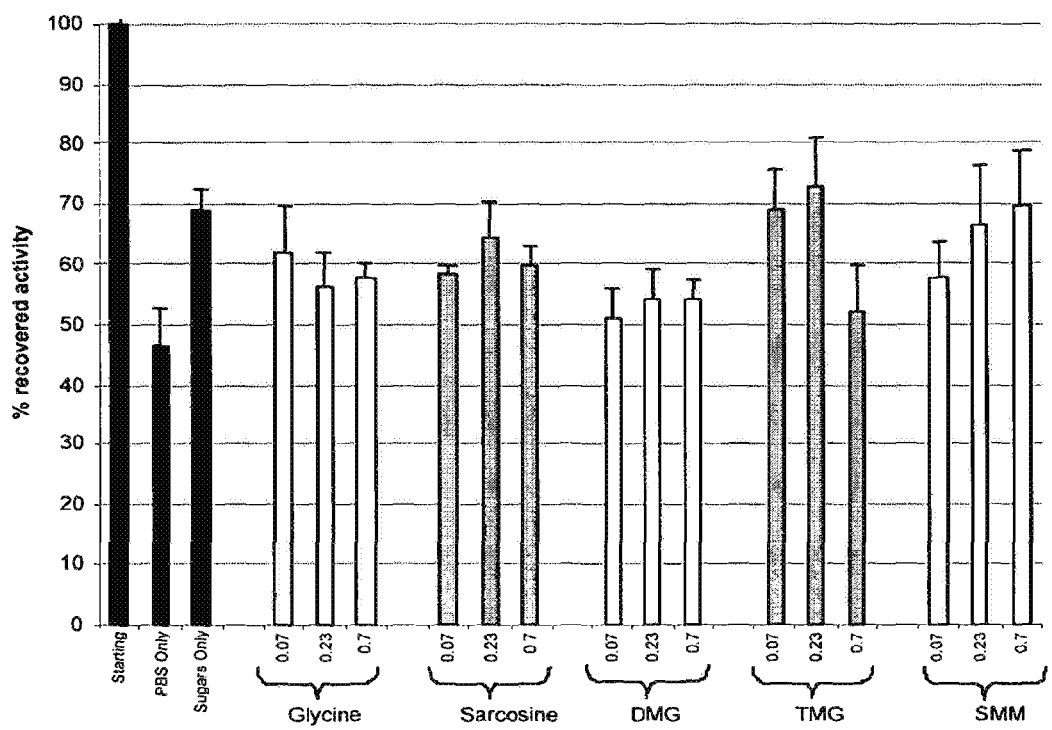
FIG. 4B shows the effect of test formulations on the recovered activity of formulations of adenovirus containing sugars (1M sucrose, 100 mM raffinose) held at 4° C. for one week. Grey and white bars represent test formulations. The Figures on the x-axis refer to concentrations in M. Black bars represent control samples, "Starting"=titre of input virus before storage, "PBS"—formulation containing no further excipients, "Sugars"=formulation comprising 1M sucrose, 100 mM raffinose. Error bars=standard error of the mean, n=3.

After one week at 4° C. adenoviral samples formulated in PBS alone, recovered viral activity was at 46% of the original titre. However, formulation together with sugars (1M Sucrose, 100 mM Raffinose) resulted in an enhancement of recovery to 69%. All formulations of adenovirus together with glycinergics or SMM and in the absence of sugars resulted in a recovery of 52-71%. Although, this represented a significant improvement over PBS, even the best glycinergic or SMM formulations yield recovery that is only equivalent to that of sugars (see FIG. 4a). When the glycinergics or SMM were formulated together with sugars, recovered viral activity was not further enhanced (50-72%). In both cases (i.e. glycinergics or SMM in the presence or absence of sugars) there was no clear dose dependency, that is to say no clear correlation between recovered viral activity and concentration of glycinergic or SMM (see FIG. 4b).

Figure 4C:
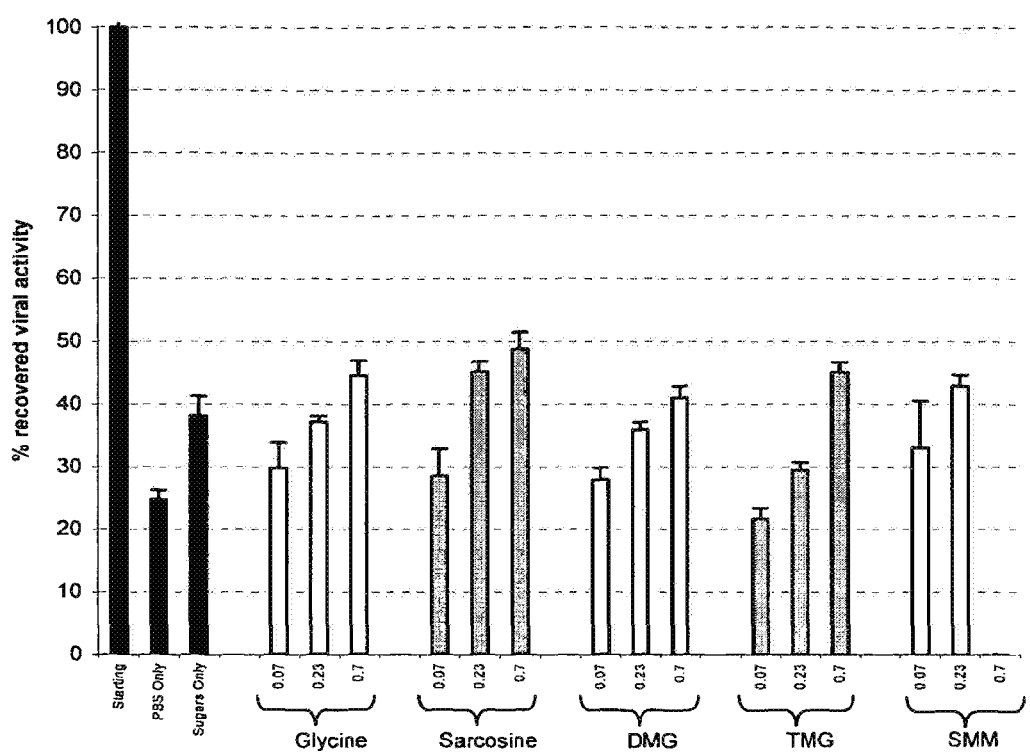
FIG. 4C shows the effect of test formulations on the recovered activity of formulations of adenovirus containing no sugars held at 37° C. for one week. Grey and white bars represent test formulations. Figures on x-axis refer to concentration in M. Black bars represent control samples, "Starting"=titre of input virus before storage, "PBS"=formulation containing no further excipients, "Sugars"=formulation comprising 1M sucrose, 100 mM raffinose, Error bars=standard error of the mean, n=3.

Recovered Viral Activity after 1 Week at 37° C. (FIGS. 4c & d) (Glycinergics and SMM WITHOUT Added Sugar or WITH Added Sugar Respectively)

After one week at 37° C. adenoviral samples formulated in PBS alone, recovered viral activity was 25% of the original titre. Formulation together with sugars (1M Sucrose, 100 mM Raffinose) enhanced recovery to 38%.

Use of glycinergics at the higher end of the tested concentration range and as the sole excipient resulted in improved efficacy over PBS alone, and in each case a strong positive correlation was observed between glycinergic concentration and recovered viral activity. Over the concentration range tested (0.07 to 0.70 M) activity was enhanced from 29% to 45% in the case of glycine, from 29% to 49% with sarcosine, from 27% to 41% with DMG, and from 21 to 45% with TMG. With each glycinergic in the concentration range tested the best results were achieved with the highest concentration tested and it was possible to recover viral activity as high or greater than when using sugars as the sole formulant (see FIG. 4c).

Figure 4D:
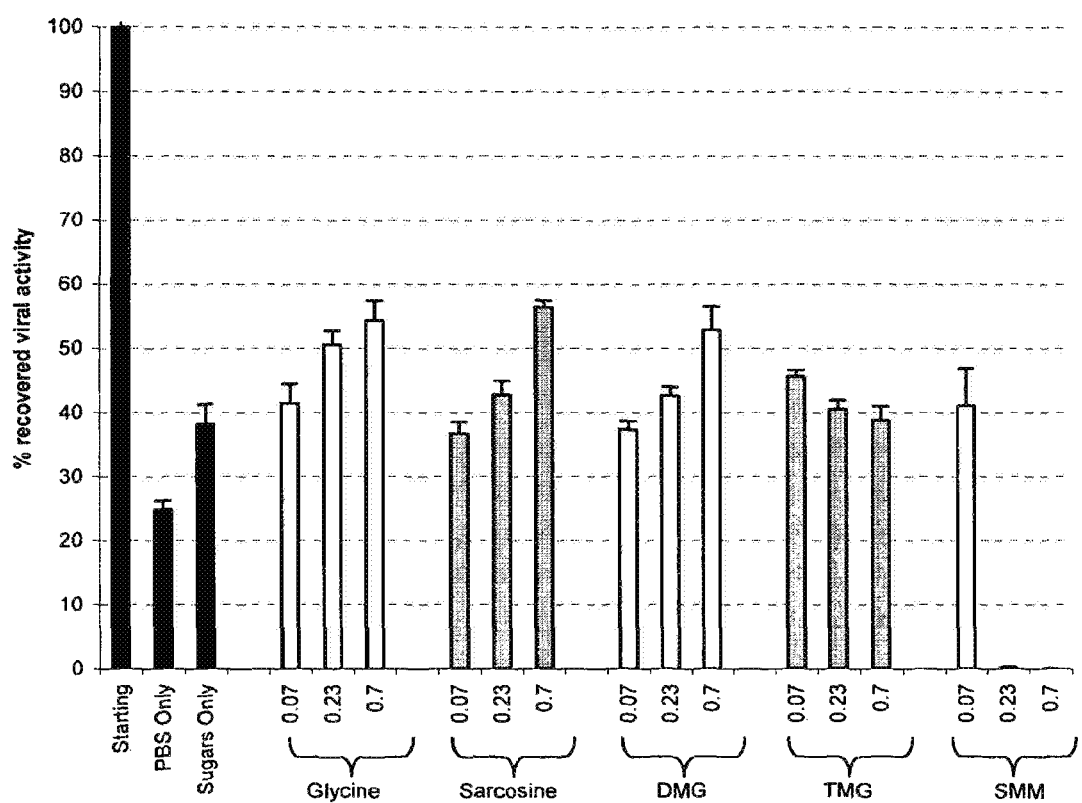
FIG. 4D shows the effect of test formulations on the recovered activity of formulations of adenovirus containing sugars (1M sucrose, 100 mM raffinose), held at 37° C. for one week. Grey and white bars represent test formulations. Figures on x-axis refer to concentration in M. Black bars represent control samples, "Starting"=titre of input virus before storage, "PBS"=formulation containing no further excipients, "Sugars"=formulation comprising 1M sucrose, 100 mM raffinose, Error bars=standard error of the mean, n=3.

Use of the following glycinergics, Glycine, Sarcosine, and DMG, across the full tested concentration range together with sugars resulted in improved efficacy over PBS alone. With the exception of the lowest sarcosine and DMG concentrations recovery was also superior to sugars alone. In each case a strong positive correlation was observed between glycinergic concentration and recovered viral activity. Over the concentration range tested (0.07 to 0.70 M) activity was enhanced from 41% to 54% in the case of glycine, from 37% to 56% with sarcosine, and from 37% to 52% with DMG (see FIG. 4d).

An exception was that when TMG was co-formulated with sugars some kind of antagonistic effect was observed. This resulted in a negative correlation between TMG concentration and recovered activity. Activity varied with TMG concentration from 45% at 0.07M to 38.7% at 0.70M. This data suggests that sugars alter the optimum concentration of TMG, since a positive interaction between TMG and sugars is observed at 0.07M and a negative one at 0.70M, but the recovered activity never exceeds what has been observed as possible with TMG alone (see FIG. 4d).

Finally, SMM preserves adenoviral activity when used as the sole formulant in the range 0.07M to 0.23M (recovered activity is 33% and 43% respectively).

Example 5

The following materials, equipment and techniques were employed unless stated otherwise in Example 5:

Materials

DMSO (Sigma D1435, Lot 118K1455)
Sucrose (Sigma 16104, Lot 70040)
Raffinose (Sigma R0250, Lot 039K0016)
PBS (Sigma D8662, Lot 118K2339)
Water (Sigma W3500, Lot 8M0411)
5 ml glass vials (Adelphi Tubes VCD005)
14 mm freeze drying stoppers (Adelphi Tubes FDIA14WG/B)
14 mm caps (Adelphi Tubes CWPP14)
L929 cells (ECCAC 85011426)
Anti-human TNF-α purified antibody (Invitrogen RHT-NFAOO, Lots 555790A and 477758B)
Human TNF-α (Sigma T6674)
3-(4,5-Dimethylthiazol-2-yl)-2,5-diphenyltetrazolium bromide (MTT) (Sigma M5655 lot MKBB4411)
Actinomyocin D (Sigma A1410)

Equipment

HERA safe class II cabinet (Thermo Fisher)
Binder $CO_2$ Incubator (Binder)
Binder APT line TM MK thermocycling test chamber (Binder)
Thermo Scientific MaxQ 4450 Incubator (Thermofisher)
KERN EW220-3NM balance (VWR)
Elcold −45° C. freezer (VWR)
Forma 900 series −80° C. freezer (Thermofisher)
Synergy HT microplate reader (Biotek)

Sample Preparation

Samples were prepared in 2 ml glass vials in triplicate. Final sugar concentrations were 1M Suc 100 mM Raf. 200 µg of rat anti TNF-α antibody in 1 ml of PBS was used as the neutralising antibody (lots 555790A and 47758B). Stocks were stored at 2-8° C. until use.

Solutions were diluted to give a range of sugar concentrations (see Table 3 below). Glass vials were left at room temperature for 10 days prior to carrying out an L929 TNF-α neutralisation assay (see below). Included in the assay was a fresh liquid stock used to indicate original antibody activity and a freeze thaw control.

TABLE 3

| Vial ID | Excipient concentration |
|---|---|
| 1, 2 | 1.25M Suc |
| 3, 4 | 1.125M Suc, 50 mM Raf |
| 5, 6 | 1M Suc, 10 mM Raf |
| 7, 8 | 0.875M Suc, 150 mM Raf |
| 9, 10 | 0.75M Suc, 50 mM Raf |
| 11, 12 | 0.625M Suc, 200 mM Raf |
| 13, 14 | 0.5M Suc, 250 mM Raf |
| 15, 16 | 0.375M Suc, 300 mM Raf |
| 17, 18 | 0.25M Suc, 350 mM Raf |
| 19, 20 | 0.125M Suc, 400 mM Raf |
| 21, 22 | 450 mM Raf |
| 23, 24 | PBS |

L929 Assay for Assessment of TNF-α Neutralisation

L929 cells were purchased from HPA cultures (cat no. 85011425). A cell suspension at a density of $3.5 \times 10^5$ cells per ml was prepared in 2% FBS (fetal bovine serum) in RPMI medium. 100 µl of the cell suspension was added to each well in a 96 well plate and incubated overnight at 37° C., 5% $CO_2$.

In a separate 96 well plate, neutralisation of the recombinant TNF-α was set up. Human anti TNF-α from each samples was serially diluted 1:2. The recombinant human TNF-α was added and the resulting antibody/cytokine mixture was incubated for 2 hours at 37° C. Following incubation, 50 µl/well of the antibody cytokine solution was transferred to the corresponding well of the plate containing the L929 cells. 50 µl of 0.25 µg/ml actinomycin D was added to each well.

Figure 5:
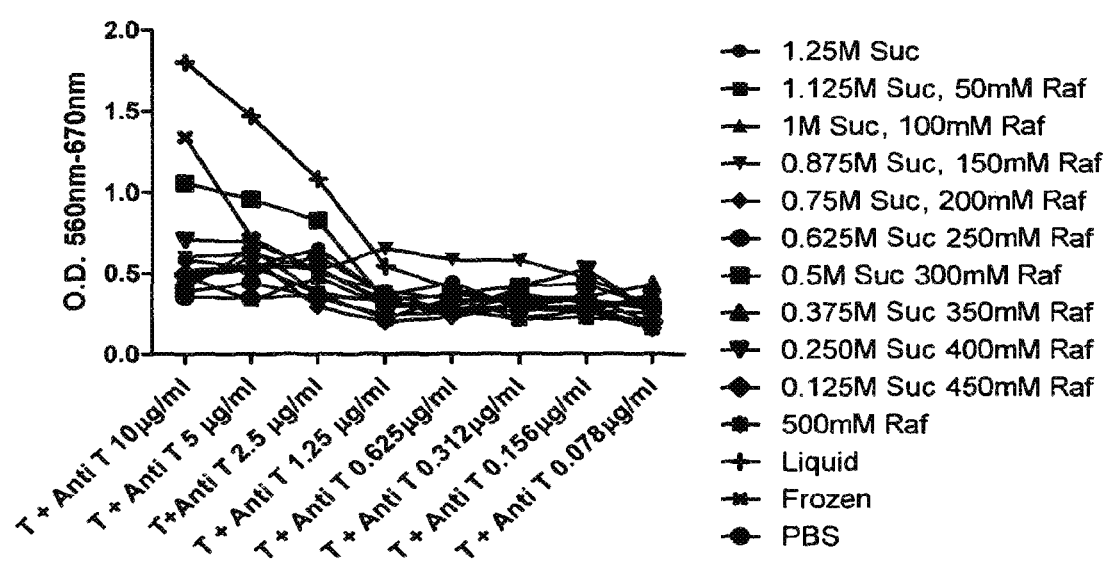
FIG. 5 shows TNF-α neutralisation by anti T (anti-TNF-α antibody). Samples were assayed following 10 days' incubation at room temperature.

Plates were incubated for 24 hours at 37° C., 5% $CO_2$ in a humidified incubator. 10 µl of 5 mg/ml MTT (3-(4,5-Dimethylthiazol-2-yl)-2,5-diphenyltetrazolium bromide, a tetrazole) solution was added to each well and the plate was incubated for 4 hours. The medium was then discarded and 100 µl DMSO was added to each well. The plates were placed on a shaking table for 5 minutes to thoroughly mix the formazan into the solvent. Finally the optical density was measured on a synergy HT plate reader at 560 nm minus the background at 670 nm Results and Discussion To optimise the concentration of sucrose and raffinose, a liquid stability study was set up using an anti-TNF-α antibody (FIG. 5). The highest level of TNF-α neutralisation was seen in the fresh liquid stock of anti-TNF-α antibody. The frozen control also showed a good level of neutralisation. The antibody stored in PBS showed no neutralisation of TNF-α. The optimal concentration of sucrose and raffinose appeared to be 0.5M sucrose and 300 mM raffinose.

Example 6

The following experimental materials and equipment were used for Example 6.

Materials
14 mm (Adelphi Tubes, CWPP14)
14 mm freeze drying stoppers (Adelphi tubes, FDIA14WG/B)
5 ml glass vials (Adelphi Tubes, VCD005)
12×33 mm total recovery vials (Waters, 186000384C)
N,N-DMG (Sigma, D1156, Lot 077K1856)
PBS (Sigma, D8662, Lot 118K2339)
Raffinose (Sigma, R0250, Lot 039K0016)
Sodium phosphate dibasic anhydrous (Sigma, 71640, Lot 0001433297)
Sodium sulphate anhydrous (Sigma, 71960, Lot 90500)
Sucrose (Sigma, 16104, Lot 80650)
TSK gel G3000 SWXL 7.8 mm I.D. 30.0 cm L (Waters, 8541, serial no. 3 SWX04PNMP6228)
TSK gel SWXL 6.0 mm I.D. 4.0 cm L (Waters, 8543, serial no. SWXP1448)
Water (Sigma, W3500, Lot 8M0411)
Adult Sheep Serum (Sigma 52263)
Equipment
Alliance series 2998 photodiode array detector (Waters)
Alliance series e2695 separations module (Waters)
Alliance series column heater (Waters)
Binder CO2 Incubator (Binder)
Ceti inverted fluorescent microscope (VWR)
Empower 2 software (Waters)
Forma 900 series −80° C. freezer (Thermofisher)
HERA safe class II cabinet (Thermo Fisher)
KERN EW220-3NM balance (VWR)
Thermo Scientific MaxQ 4450 Incubator (Thermofisher)
IgG Formulation Sheep IgG purified from adult sheep serum (Sigma) by sodium sulphate precipitation was used to investigate the efficacy of sugars, and DMG, as excipients in the liquid storage of immunoglobulins. The sheep IgG was stored at 4° C. prior to use at a concentration of 46 µg/µl (as determined by Bradford assay). Aliquots of IgG were diluted in PBS and a selection of novel excipients to a concentration of 4.6 µg/µl in a volume of 300 µl. The novel excipient component varied as shown in Table 4 below. Each formulation treatment was replicated 12 times.

TABLE 4

| Treatment | DMG (M) | Sucrose (M) | Raffinose (mM) |
|---|---|---|---|
| PBS only | 0 | 0 | 0 |
| Sugars only | 0 | 1 | 100 |
| DMG only | 0.7 | 0 | 0 |
| DMG + Sugars | 0.7 | 1 | 100 |

Thermal Challenge

Three replicates of each excipient treatment were placed at each temperature challenge (−80° C., +4° C., +37° C., +56° C.) on day 0. On day 1, 5 and 31 of the experiment 60 µl subsamples were removed from thermal challenge for testing by HPLC.

HPLC Based Assay

The 60 µl subsamples were placed in maximum recovery vials in the separations unit and held at 4° C. A size exclusion chromatography (SEC) column (TSK gel G3000 SWXL) and compatible guard column (TSK gel SWXL) were attached in series (guard first) to the separations unit and conditioned at 25° C. to the mobile phase (0.1M Sodium phosphate, 0.1M Sodium sulphate, pH6.8) with a flow rate of 1.0 ml/min. Once the baseline had settled, 50 µl injections of each sample were made to the mobile phase. Run time for each sample was 20 minutes, and detection of separated molecules was by a PDA (photodiode array detector detecting at 280 nm with a resolution of 2.4 mm.

Blocking

One replicate of each excipient treatment was processed per block of samples and each block was bracketed by gel filtration standards to confirm the robustness of the data.

Analysis of Results

The area under all significant peaks with a retention time of between 5 and 20 minutes was measured using EmPower2 software. Total area under the curves included the area under the void peak so molecules that flowed straight through the column and could not be sized were also included in the calculation.

Purity of the IgG was measured by calculating the area under the monomer peak as a percentage of total area under the identified peaks (monomer, aggregate and void).

IgG % purity of each treatment was then converted relative to the purity of the PBS sample from the same day and temperature set.

The percentage point change in IgG % purity between day 1 and day 5 was calculated by subtracting the mean of the former from the mean of the later for each excipient treatment.

Results and Discussion

Figure 6:
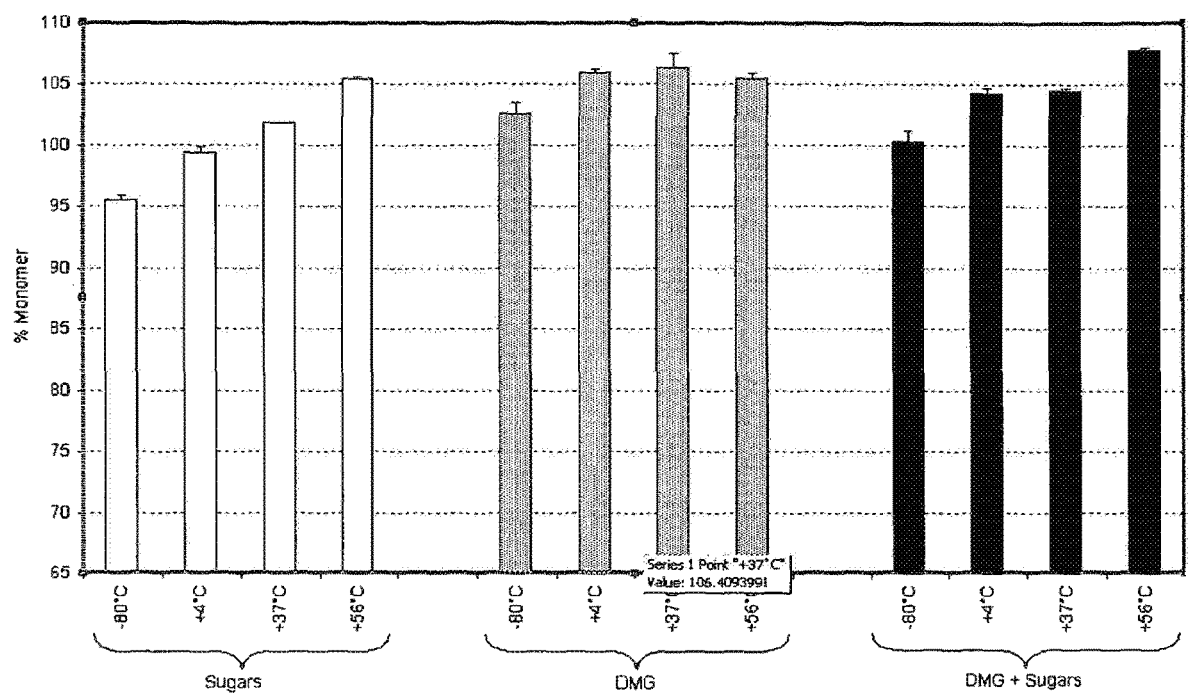
FIG. 6 shows the results of an investigation into the effect of excipients on the stabilisation of IgG in liquid formulation. Bars represent percentage purity of IgG in novel excipient formulations relative to PBS only formulations of each comparable thermal treatment (thus PBS only purity adjusted to 100%) from Example 6. Represented treatments comprise sugars only (white), DMG only (grey) and DMG and sugars (black), all collected on day 1 of the experiment. Error bars represent standard error of the mean IgG purity of each treatment in percentage points (n=3).

Day 1—Sugar Only Formulations (See FIG. 6)

On day one of the experiment (24 hours thermal challenge) samples formulated with sugars alone had an average % purity of 95-105% of those formulated with PBS alone (and held at equivalent temperatures). Those sugar only formulations refrigerated at +4° C. were not significantly different from PBS alone suggesting that at this temperature there is no significant advantage to formulation with sugars alone after only one day. In fact, sugar formulations held at −80° C. (i.e. one freeze-thaw cycle) were significantly worse than PBS alone (95%). However, those sugar formulations held at +37° C. and +56° C. were significantly better than PBS only (102% and 105% respectively). Furthermore, this increase could not be accounted for by an initial disaggregation of IgG caused by elevated temperature as the figures are relative to PBS formulations held at equivalent temperatures. This improvement is a genuine advantage of formulating with sugars.

Day 1—DMG Formulations (See FIG. 6)

All samples formulated with DMG yielded a significantly improved purity relative to those formulated with PBS (102-106%). Poorest of these improvements was observed in samples stored at −80° C. (i.e. one freeze-thaw) (102%) but this as well as those held at +4° C. (106%) and 37° C. (106%) represent an improvement on sugar only formulations. DMG formulations held at 56° C. (105%) were only equivalent to those formulated with sugars alone.

Day 1—DMG and Sugar Formulations (See FIG. 6)

All samples co-formulated with sugars and DMG gave an improved yield of IgG purity compared to PBS only treatments (100-108%). Of these samples those held at −80° C. (100%), +4° C. (104%), and +37° C. (104%) were an improvement over sugars only. Those formulations held at +56° C. (108%) yielded an improvement over both DMG only formulations (105%) and sugar only formulations (105%).

Day 1—Summary (See FIG. 6)

The results discussed above can be seen in FIG. 6. The figure shows clear trends. The differences are slight; however, the timescale is short. The differences between day 5 and day 1 are probably of greater significance and interest.

Area of Monomer Peaks

Figure 7:
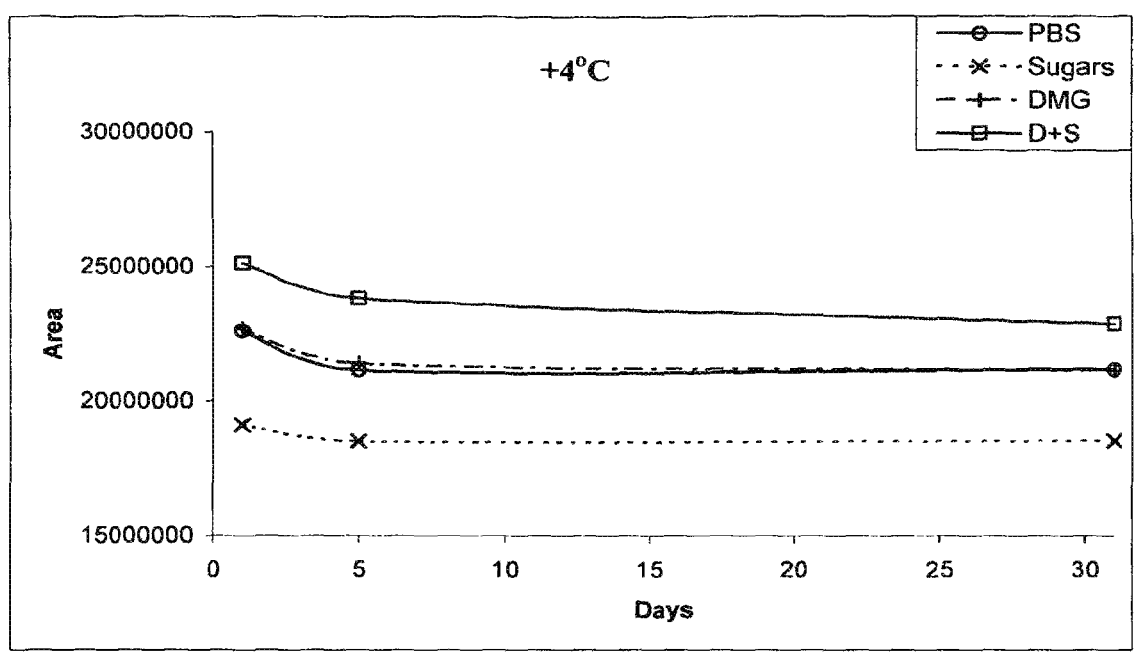
FIG. 7 shows the average monomer peak on day 1, 5 and 31 for the formulations prepared in Example 6 stored at 4° C.
Figure 8:
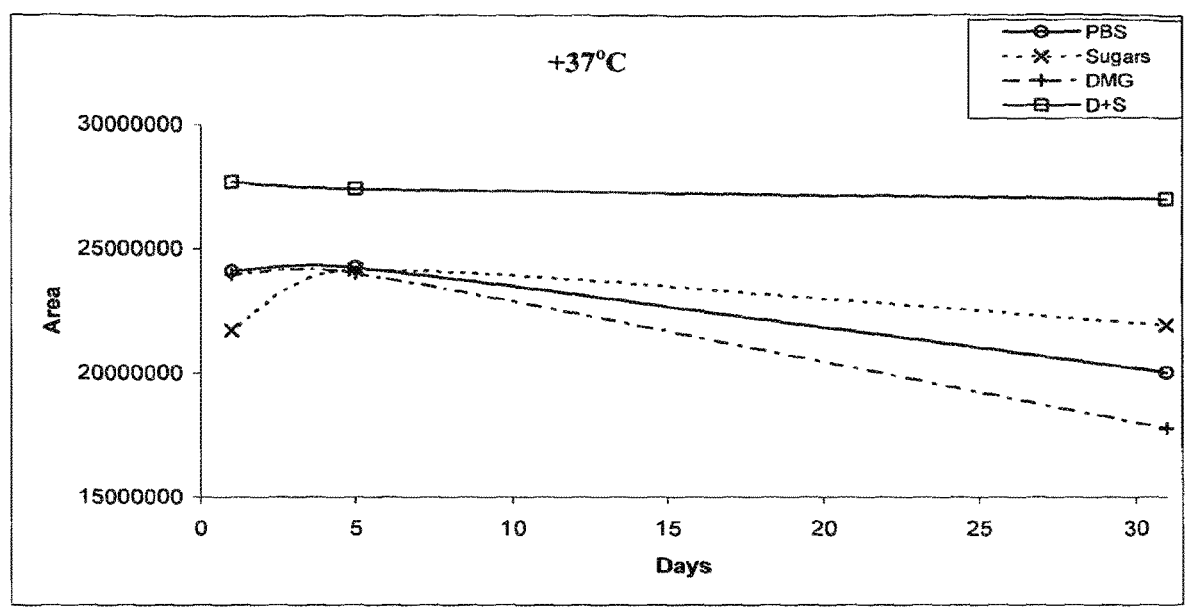
FIG. 8 shows the average monomer peak on day 1, 5 and 31 for the formulations prepared in Example 6 stored at 37° C.

FIGS. 7 and 8 show the area of the monomer peak for all formulations over time (day 1, 5, and 31) stored at 4° C. and 37° C. respectively. Area of the monomer peak is taken as an estimate of recovered monomeric IgG.

Day 1—at 4° C.

FIG. 3 shows that as early as day 1 formulations held at 4° C. exhibit differences in the area of their monomer peak. These differences could be mediated by excipient specific disaggregation. Treatments formulated with DMG and sugars have the largest monomer peak and hence most recovered monomeric IgG. Treatments formulated with sugars alone show the smallest monomer IgG and hence least recovered monomeric IgG. Samples formulated with PBS or DMG alone are not significantly different and are intermediate to these.

Day 1 to Day 5, and Day 5 to Day 31 at 4° C.

In all formulations stored at 4° C. there is a drop in recovered monomeric IgG of a comparable magnitude. Subsequently, between day 5 and 31, there is no further loss in monomeric IgG.

Day 1 at 37° C.

Comparison of FIGS. 7 and 8 shows that treatments held at 37° C. all have a higher amount or recovered monomeric IgG than equivalent formulations held at 4° C. This is evidence of temperature mediated disaggregation.

Day 1 to Day 5 at 37° C.

At 37° C. there is no loss in monomer between day 1 and 5 in any treatments except DMG alone. This lack of loss may be due to degradation being balanced by heat mediated disaggregation.

Day 5 to Day 31 at 37° C.

Samples formulated with PBS, or Sugars alone, or DMG alone, all show a significant decline in monomeric IgG between day 5 and day 31. Of these treatments DMG alone actually shows the steepest decline, followed by PBS. Formulation with sugars alone slightly enhances recovery of monomeric IgG over PBS but as stated still suffers significant loss. However, formulation with DMG and sugars shows no significant decline in monomeric IgG over this timescale. As such coformulations of DMG and sugars offer significant potential as excipients for the enhanced thermostability of IgG.

Example 7—Stablisation of Adenovirus

The following materials, equipment and techniques were employed unless stated otherwise in Example 7 and Example 8:

| Materials | |
|---|---|
| Chemical | |
| Dimethylglycine (DMG) | (Sigma D1156, Lot 077K1856) |
| Dimethylsulfone (MSM) | (Sigma M81705, Lot 0001452516) |
| Dulbecco's Modified Eagles Medium (DMEM) | (Sigma D5796, Lot RNBB1139) |
| Foetal Bovine Serum (FBS) | (Sigma F7524, Lot 109K3395) |
| Penicillin Streptomycin (PS) | (Sigma P4458, Lot 0409M00393) |
| Saline Sodium Citrate (SSC) | (Sigma S6639, Lot 020M8404) |
| Sucrose | (Sigma 16104, Lot SZB90120) |
| Water | (Sigma W3500, Lot RNBB1139) |
| Biological | |
| Adenovirus | (Vector Biolabs cat. 1060) |
| BHK-21 cell line | (ECCAC CB2857) |
| HEK 293 | (ECACC 85120602) |

-continued

| Materials | |
|---|---|
| Other | |
| 5 ml glass vials | (Adelphi Tubes VCD005) |
| 14 mm freeze-drying stoppers | (Adelphi Tubes FDIA14WG/B) |
| 14 mm caps | (Adelphi Tubes CWPP14) |
| Equipment | |
| HERA safe class II cabinet | (Thermo Fisher, EQP# 011 & 012) |
| DMIL LED Inverted Microscope | (Leica, EQP#062) |
| Binder $CO_2$ Incubator | (Binder, EQP#014) |
| Forma 900 series −80° C. freezer | (Thermofisher, EQP#015) |
| ATL-84-1 Atlion Balance | (Acculab, EQP#088) |
| IP250 37° C. Incubator | (LTE, EQP#016) |

Preparation of Liquid Virus Preparations

Recombinant human adenovirus Ad5 (Vector Biolabs) expressing enhanced GFP (Green Fluorescent Protein) under a CMV promoter, and with a titre (pre-freeze) of $6.7 \times 10^5$ pfu/ml in SSC, was removed from storage at −80° C. and allowed to thaw. 50 µl aliquots were added to 5 ml glass vials. To these 50 µl virus samples was added 250 µl of a formulation mixture composed of DMG, MSM and optionally sucrose. Each formulation mixture was made up in SSC. The concentration of DMG, MSM and sucrose in each formulation after addition to the virus sample is shown in Table 5:

TABLE 5

Tested formulations

| Formulation | Sucrose (M) | MSM (M) | DMG (M) |
|---|---|---|---|
| 1 | 0.00 | 0.10 | 0.10 |
| 2 | 0.15 | 0.10 | 0.10 |
| 3 | 0.00 | 1.00 | 0.10 |
| 4 | 0.15 | 1.00 | 0.10 |
| 5 | 0.08 | 0.55 | 0.55 |
| 6 | 0.08 | 0.55 | 0.55 |
| 7 | 0.08 | 0.55 | 0.55 |
| 8 | 0.00 | 0.10 | 1.00 |
| 9 | 0.15 | 0.10 | 1.00 |
| 10 | 0.00 | 1.00 | 1.00 |
| 11 | 0.15 | 1.00 | 1.00 |

The vials were stoppered and capped (screw cap) before being placed at 37° C. for thermal challenge. Thermal challenge was for 7 days, after which all the vials were returned to 4° C. until it was practical to assay them.

Assay for Infectious Adenovirus 96 flat bottomed cell culture dishes (VWR, UK) were seeded with HEK 293 (ECACC 85120602) cells at $10^5$ cells per ml (100 µl per well) and maintained at 37° C. with 5% $CO_2$. After achieving 90% confluence, cells were inoculated.

Vials containing adenovirus plus excipient were reconstituted in 300 µl SSC. A 1 in 10 dilution step was then taken by taking 20 µl from the reconstituted vial and adding to 180 µl of Dulbecco's Modified Eagle Medium (DMEM). A further 1 in 100 dilution (of the original sample) was performed by taking 20 µl of the 1 in 10 dilution and adding it to 180 µl of DMEM. 100 µl of each of the resultant dilution (1 in 10 and 1 in 100) was then added to wells of the plate containing HEK 293 cells.

Additionally, a further sample of adenovirus, from the same source and with the same titre (on storage at −80° C.) used in the excipient treatments, was thawed and used to produce a 1 in 10 dilution series (in DMEM+10% FBS). Dilutions ranging from 1 in 10 to 1 in $10^6$ were also added to individual wells containing HEK 293s. At 48 hours post inoculation, the number GFP (Green Fluorescent Protein) cells per well were counted using fluorescent microscopy, and this was subsequently converted to pfu/ml of the treated samples taking into account the volume applied and dilution of the inoculum.

Results

Figure 9:
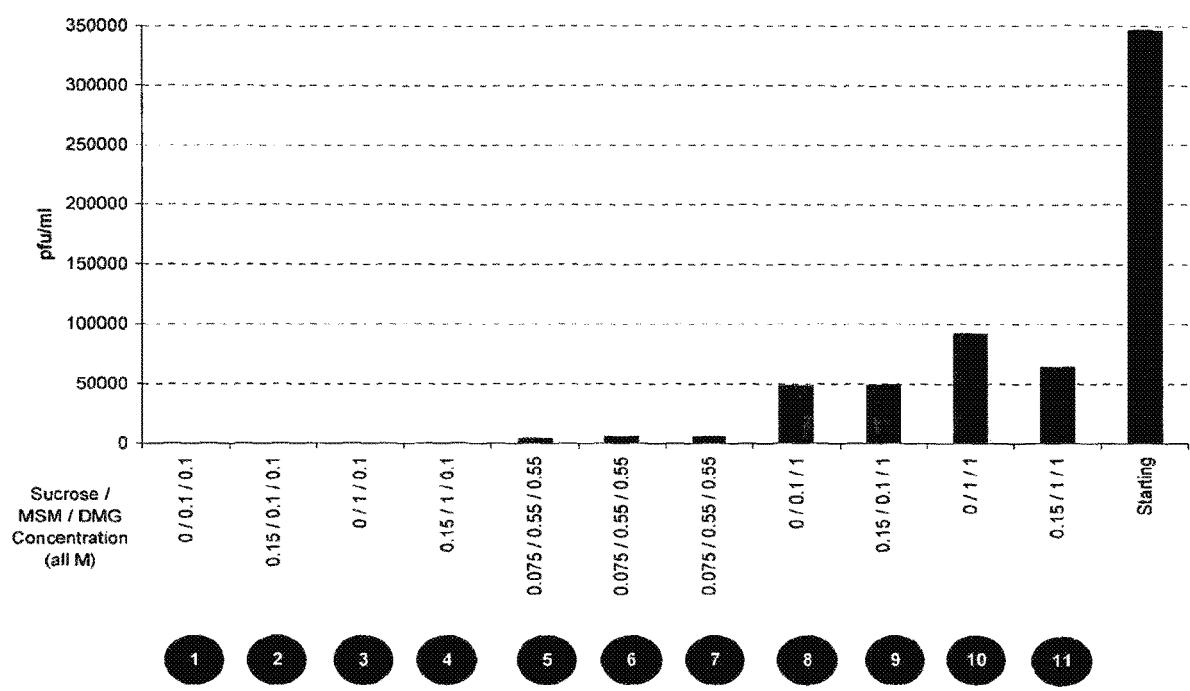
FIG. 9 shows the results obtained in Example 7 in which the ability of eleven formulations to stabilise adenovirus against thermal challenge was assessed following 7 days at 37° C.

The results are shown in FIG. 9. When the data was analysed by multiple linear regression (MLR) analysis using the MODDE 9.0 programme (Umetrics, Sweden), a synergistic effect was observed when MSM and DMG where used in combination Example 8: Stablisation of MVA Preparation of Liquid Virus Preparations MVA was recovered from storage at −80° C. and thawed. 50 µl aliquots were added to 5 ml glass vials. To these vials was added 250 µl of a formulation mixture listed in Table 1 above. The vials were stoppered and screw caps tightened to seal. The vials were immediately placed at 37° C. for thermal challenge. Thermal challenge was for 7 days, after which all the vials were returned to 4° C. until it was practical to assay them.

Assay for Infectious MVA

Assay plates (96 wells) were seeded with BHK-21 cells (100 µl per well, $10^5$ cells/ml). Cells were diluted in DMEM supplemented with 10% FBS, and 1% PS. The plates were placed at +37° C., +5% $CO_2$ for 1 to 2 hours.

Meanwhile, a dilution series of the formulated MVA samples was prepared (in the same growth media) ranging from $10^{-1}$ to $10^{-4}$. Each dilution series was prepared 4 times. 35 µl of each dilution was applied to individual wells containing BHK-21 cells and the wells were topped up with a further 65 µl of media.

On day 6 after inoculation, the wells were scored for presence or absence of cytopathic effect (CPE) and $TCID_{50}$ calculated. These were then used to estimate the concentration of infectious MVA per ml in the thermo-challenged vials.

Results

Figure 10:
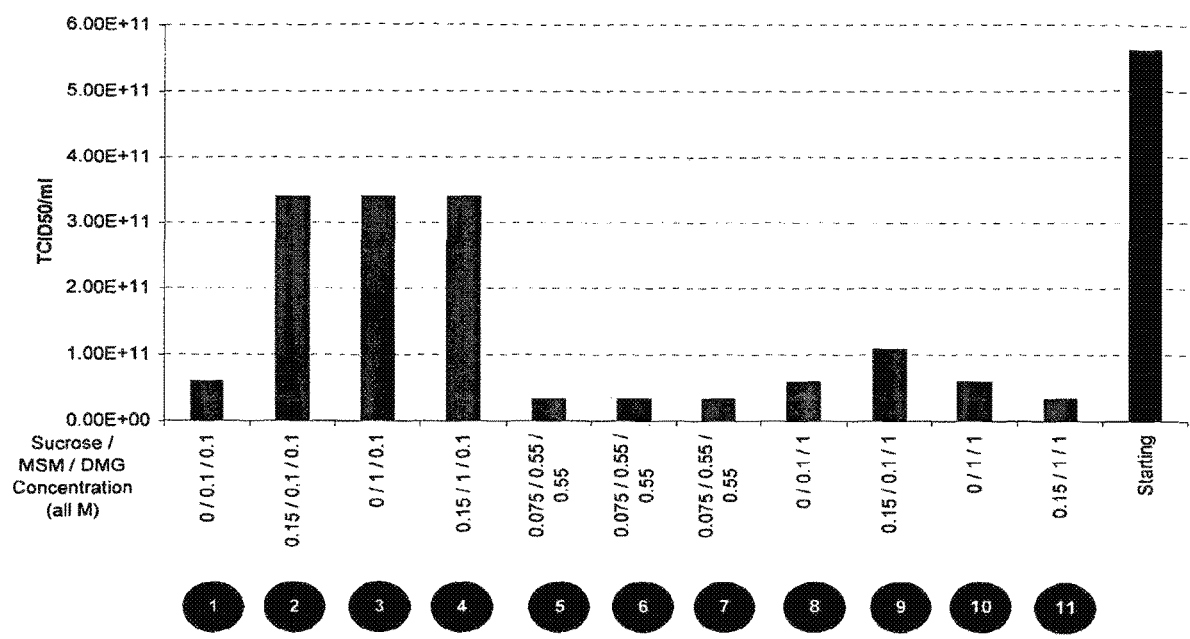
FIG. 10 shows the results obtained in Example 8 in which the ability of eleven formulations to stabilise MVA against thermal challenge at 37° C. for 7 days was assessed.

The results are shown in FIG. 10.

Example 9

| Materials | | | |
|---|---|---|---|
| | Supplier | Catalogue No. | Lot No. |
| Chemical | | | |
| 20x SSC | Sigma | S6639 | 020M8404 |
| Dulbeccos Modified Eagles Medium | Sigma | D5796 | RNBB1139 |
| Foetal Bovine Serum | Sigma | F7524 | 109K3395 |
| Branched PEI (P-Bra) | Sigma | P3143 | 127K0110 |
| Penicillin Streptomycin | Sigma | P4458 | 0409M0093 |
| Raffinose | Sigma | R0250 | 050M0053 |
| Sucrose | Sigma | 16104 | SZB90120 |
| Water | Sigma | W3500 | 8M0411 |

-continued

| Materials | | |
|---|---|---|
| | Supplier | Catalogue No. |
| Biological | | |
| Adenovirus | Vector Biolabs | Ad-CMV-GFP |
| HEK 293 | ECACC | 85120602 |
| Other | | |
| 5 ml glass vials | Adelphi Tubes | VCD005 |
| 14 mm freeze drying stoppers | Adelphi Tubes | FDIA14WG/B |
| 14 mm caps | Adelphi Tubes | CWPP14 |
| Equipment | Manufacturer | Equipment No. |
| HERA safe class II cabinet | Thermo Fisher | EQP# 011 & 012 |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods

Design of Experiment

Figure 11:
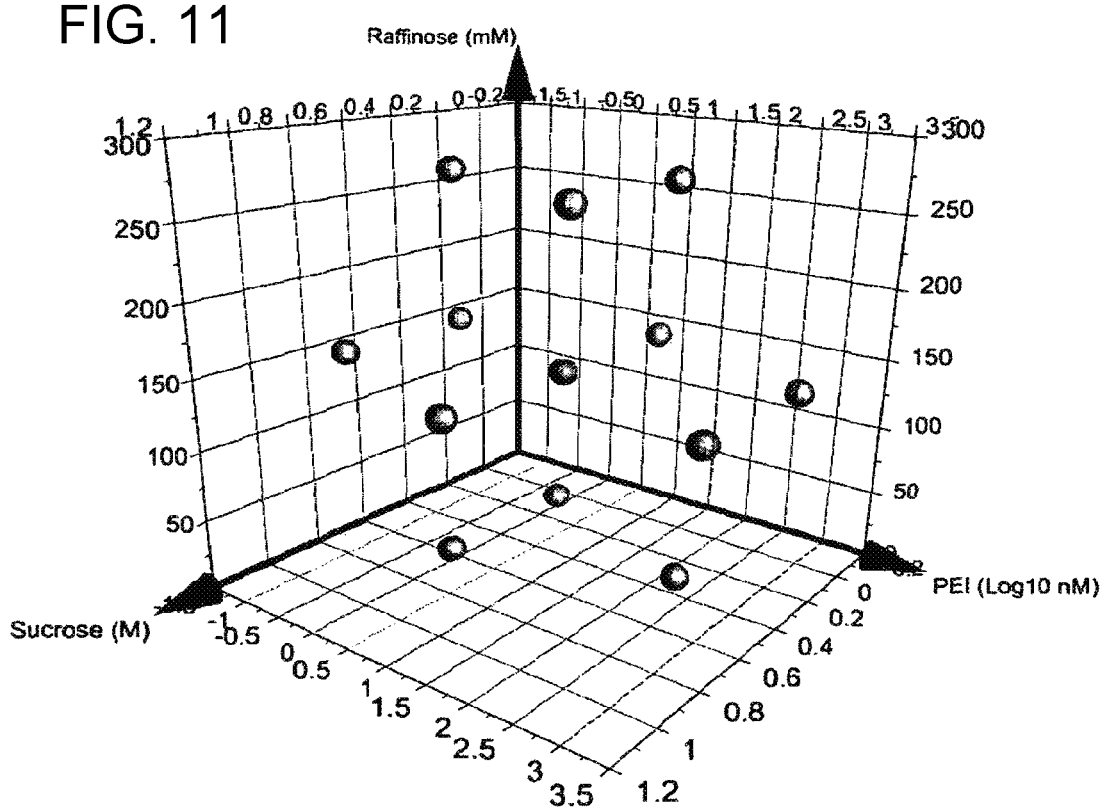
FIG. 11 shows a 3D representation of the design space in Example 9. Spheres represent formulations within the design space that were tested. This design is a Doehlert RSM design.

MODDE 9.0 (Umetrics) was used to generate a Doehlert experimental design (see FIG. 11). Doehlert designs are response surface modelling designs constructed from regular simplexes. They are easily extendable in different directions and new factors can be added to an existing design. Unlike regular formulation designs non-significant factors can be eliminated from the analysis and so do not become a confounding factor.

Furthermore, different factors within the design are tested at a different number of levels, so it is possible to allocate more test levels to factors that we suspect are of greater importance. Thus, PEI was tested at seven levels, whilst sucrose was tested at five and raffinose three. This model retains the ability to model for second order effects and interactions. The design included three factors and three replicate centre-points, resulting in 15 test samples.

Sucrose was tested between 0 and 1M. Raffinose was tested over a range of 0 to 300 mM although the nature of the Doehlert design meant that tested levels did not include 0 mM. Instead the following ranges were tested: 27.5, 150.0, and 272.5 mM.

PEI was tested over a logarithmic range of from 0.04-4000 nM.

Stability of Adenovirus in a Liquid Setting

Preparation of and Thermal Challenge of Formulated Adenovirus in a Liquid Setting Recombinant Adenovirus expressing enhanced GFP under a CMV promoter, with a titre (pre-freeze) of $6.7 \times 10^5$ pfu/ml in SSC, was removed from storage at −80° C. and allowed to thaw. Subsequently, 50 μl aliquots of virus were added to 15, 5 ml, glass vials. To each vial 250 μl of an excipient blend was admixed. The excipient blend formulations mixed with virus are described in Table 6 and were made up in SSC.

The vials were stoppered and capped (screw cap) before being placed at +37° C. for 1 week of thermochallenge and later transferred to +4° C. until it was practical to assay them.

TABLE 6

| Formulation Number | Sucrose (M) | Raffinose (mM) | PEI (nM) | Recovered Viral Activity (pfu/ml) |
|---|---|---|---|---|
| 1 | 0.25 | 150.0 | 0.09 | 3.6E+04 |
| 2 | 0.75 | 150.0 | 0.09 | 2.8E+05 |
| 3 | 0.5 | 272.5 | 0.46 | 2.3E+05 |
| 4 | 0.25 | 27.5 | 2.40 | 6.0E+02 |
| 5 | 0.75 | 27.5 | 2.40 | 1.1E+05 |
| 6 | 0 | 150.0 | 12.65 | 6.0E+02 |
| 7 | 0.5 | 150.0 | 12.65 | 2.3E+05 |
| 8 | 0.5 | 150.0 | 12.65 | 1.3E+05 |
| 9 | 0.5 | 150.0 | 12.65 | 3.3E+05 |
| 10 | 1 | 150.0 | 12.65 | 3.9E+05 |
| 11 | 0.25 | 272.5 | 66.64 | 8.4E+03 |
| 12 | 0.75 | 272.5 | 66.64 | 2.0E+05 |
| 13 | 0.5 | 27.5 | 351.10 | 6.0E+02 |
| 14 | 0.25 | 150.0 | 1849.79 | 6.0E+02 |
| 15 | 0.75 | 150.0 | 1849.79 | 6.0E+02 |

Assay of Adenovirus

HEK 293 cells were prepared in 96 well flat bottomed cell culture dishes for inoculation by seeding at $10^5$ cells per ml (100 μl per well) and maintained at 37° C. with 5% $CO_2$. After 2 hours cells were inoculated as follows.

Thermo-challenged virus samples were diluted 1 in 10, and 1 in 100 in DMEM+10% FBS+1% PS. 100 μl of each of the resulting diluted virus samples were then added to individual wells of the assay plate. Additionally, a second aliquot of the original adenovirus in SSC was thawed from −80° C. and a 10 fold dilution series (from 1 in 10 to 1 in 100,000) also prepared in DMEM+10% FBS+1% PS. The positive control dilution series was inoculated in duplicate to each 96 well plate used. After a further 48 hours, the number of GFP cells per well were counted using fluorescent microscopy.

Results

Figure 12:
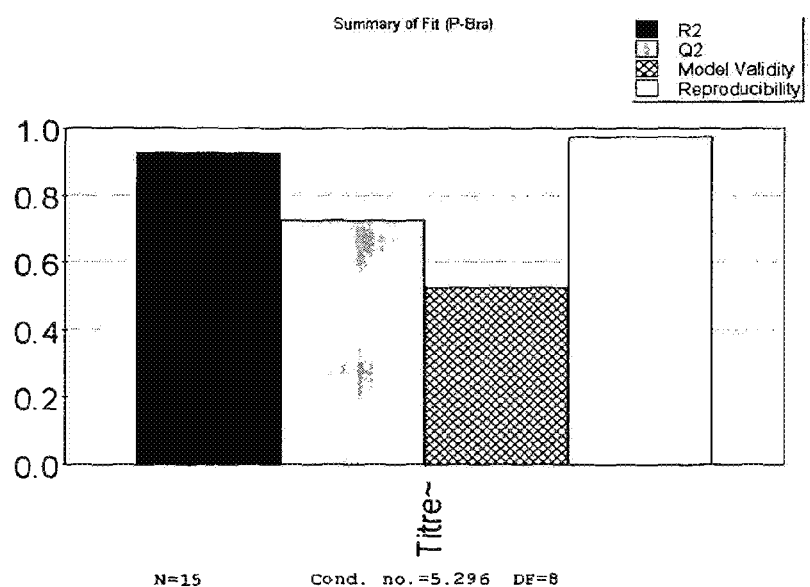
FIG. 12 summarises statistics for the model used to represent the branched PEI (P-Bra) data in Example 9

The results are set out in Table 6 above. FIG. 12 shows that the model based on the P-Bra+Suc+Raff data is a strong one. $R^2$ (0.93) demonstrates a good fit, $Q^2$ (0.72) suggests a relatively strong predictive model.

Figure 13:
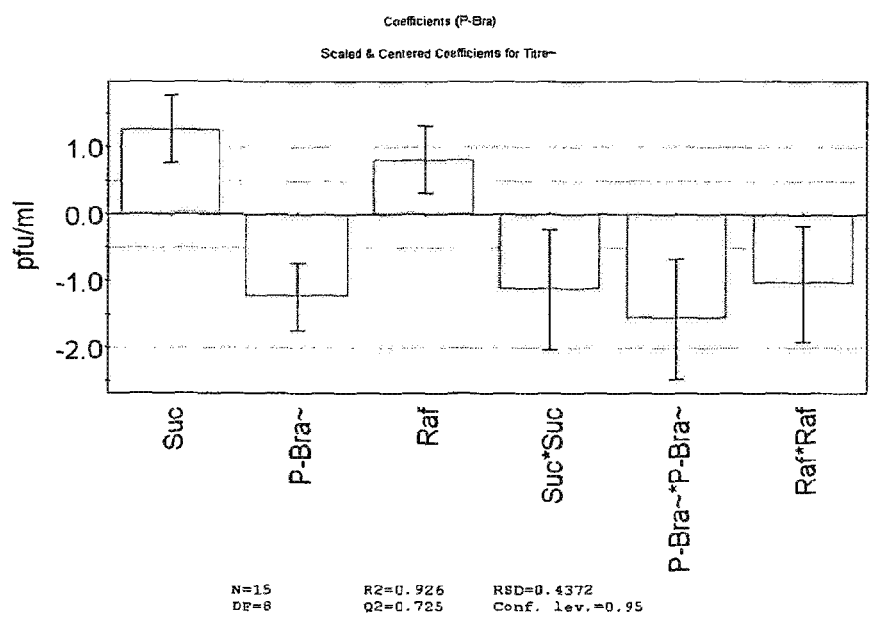
FIG. 13 shows the terms retained in the model in Example 9 after fine tuning.

Significant terms in the model (see FIG. 13) include first and second order effects of all three excipients but no interactions between them.

Figure 14:
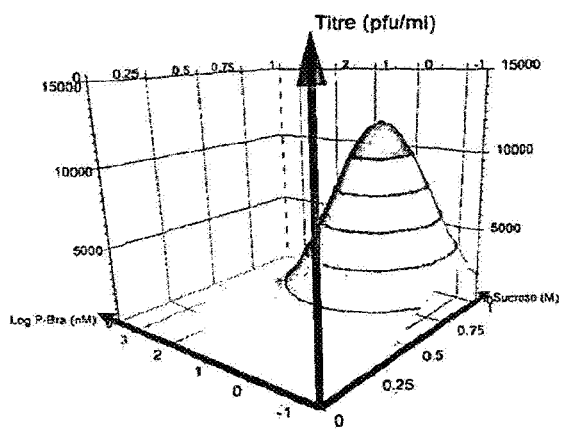
FIG. 14 plots the surface response of the predicted recovered viral titre in formulations of P-Bra and sucrose at three different levels of raffinose using the model in Example 9. The levels of raffinose uses are: "Low"=raffinose at 0 mM, "Mid"=raffinose at 150 mM, "raffinose"=Raff at 300 mM.
Figure 14:
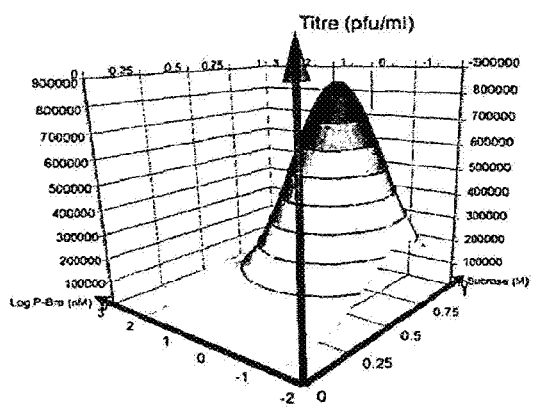
Figure 14:
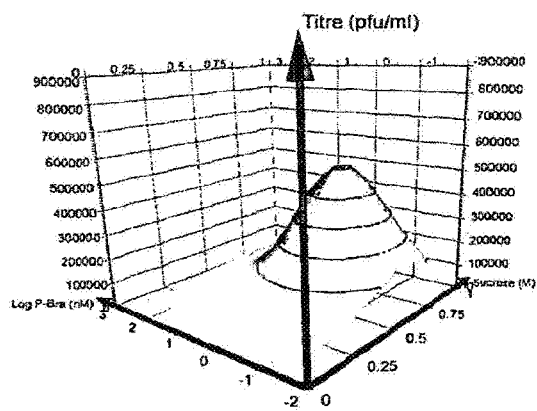

Surface response plots (FIG. 14) illustrate the effects of sucrose and branched PEI (P-Bra) most clearly. The peak on each graph represents the optimum formulation at each stated raffinose concentration (0, 150 and 300 mM). The three graphs show that raffinose does little to alter the optimum P-Bra or sucrose concentrations but does alter the maximum achievable recovered viral activity.

A positive control had also been assayed alongside the test samples. The virus used as a control was an additional aliquot of the same virus used in this assay that had been stored at −80° C. The assayed titre of this sample was $6.7 \times 10^5$ pfu/ml. Monte-Carlo simulations were used to predict an optimum formulation. The positive control was used as a target for optimisation since the model predicts some formulations would result in greater than 100% recovered viral activity (see below).

Figure 15:
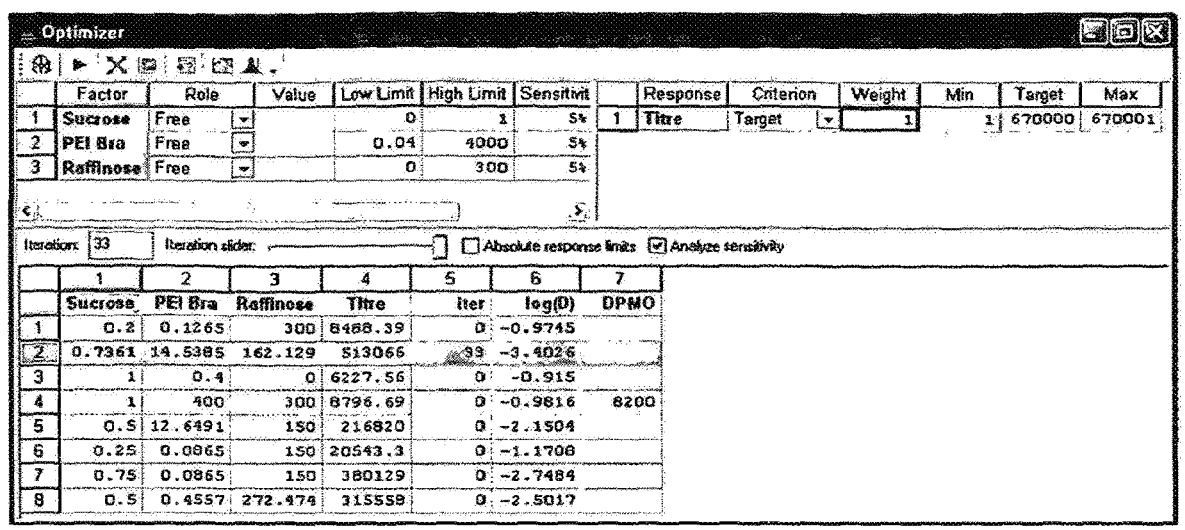
FIG. 15 shows a screen capture of settings and outputs from the optimum predictions based on the model of the data in Example 9 generated using Monte-Carlo simulations. The predicted optima highlighted were: sucrose=0.74M, branched PEI (P-Bra)=14 nM, raffinose=162.13 mM.

The predicted optimum formulation is: sucrose=0.74M, P-Bra=14 nM, raffinose=162 mM (see FIG. 15). The optimum formulation identified herein was predicted to result in a recovered viral titre of $5.1 \times 10^5$ pfu/ml, or a loss of only 24% of viral activity.

Example 10

Materials

Chemical

| | Supplier | Product Code | Lot No. |
|---|---|---|---|
| 20x SSC | Sigma | S6639 | 020M8404 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Trimethyl glycine | Sigma | B2629 | 069K1514 |
| Water | Sigma | W3500 | 8M0411 |

Biological

| | Supplier | Product Code |
|---|---|---|
| BHK-21 cell line | ECACC | CB2857 |
| MVA | ATCC | VR-1508 |

Other

| | Manufacturer | Product Code |
|---|---|---|
| 5 ml glass vials | Adelphi Tubes | VCD005 |
| 14 mm freeze drying stoppers | Adelphi Tubes | FDIA14WG/B |
| 14 mm caps | Adelphi Tubes | CWPP14 |

| Equipment | Manufacturer | Equipment No. |
|---|---|---|
| HERA safe class II cabinet | Thermo Fisher | EQP# 011 & 012 |
| DMIL LED Inverted Microscope | Leica | EQP#062 |
| Binder $CO_2$ Incubator | Binder | EQP#014 |
| Forma 900 series $-80°$ C. freezer | Thermofisher | EQP#015 |
| ATL-84-1 Atlion Balance | Acculab | EQP#088 |
| IP250 37° C. Incubator | LTE | EQP#016 |

Methods
Design of Experiment

Figure 16:
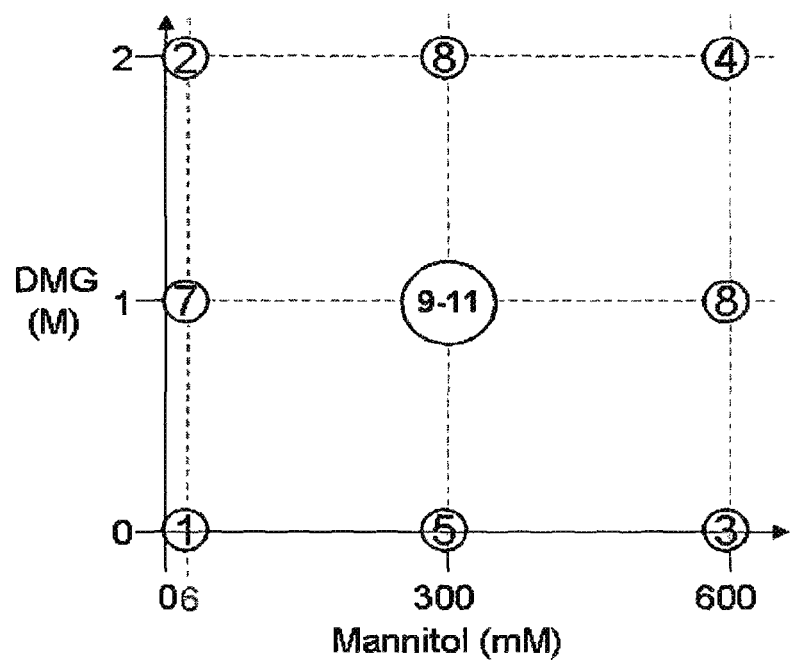
FIG. 16 shows a representation of the design space in Example 10. Numbered circles represent formulations within the design space that are tested. This design is a CCF RSM design. Numbers in circles refer to sample I.D.s in Table 7.

MODDE 9.0 was used to generate a Central Composite Face-Centred (CCF) design (see FIG. 16). CCF designs are a form of Response Surface Modelling (RSM) design that tests only three levels of each factor but still supports a quadratic model. Unlike regular formulation designs non-significant factors can be eliminated from the analysis and so do not become a confounding factor.

Preparation of and Thermal Challenge of Formulated MVA in a Liquid Setting

MVA was recovered from storage at $-80°$ C. and thawed. 50 µl aliquots of the MVA were added to 15, 5 ml, glass vials. Subsequently, 50 µl aliquots of virus were added to 15, 5 ml, glass vials. To each vial 250 µl of an excipient blend was admixed. The excipient blend formulations once mixed with virus are described in Table 7 and were made up in SSC.

TABLE 7

| Formulation No. | Sucrose (M) | Raffinose (mM) | TMG (M) | Titre (pfu/ml) |
|---|---|---|---|---|
| 1 | 0.25 | 150.0 | 0.13 | 7.6E+04 |
| 2 | 0.75 | 150.0 | 0.13 | 3.0E+05 |
| 3 | 0.5 | 272.5 | 0.42 | 3.0E+05 |
| 4 | 0.25 | 27.5 | 0.71 | 3.0E+05 |
| 5 | 0.75 | 27.5 | 0.71 | 4.8E+05 |
| 6 | 0 | 150.0 | 1.00 | 1.9E+05 |
| 7 | 0.5 | 150.0 | 1.00 | 4.8E+05 |
| 8 | 0.5 | 150.0 | 1.00 | 4.8E+05 |
| 9 | 0.5 | 150.0 | 1.00 | 3.0E+05 |
| 10 | 1 | 150.0 | 1.00 | 3.0E+05 |
| 11 | 0.25 | 272.5 | 1.29 | 4.8E+05 |
| 12 | 0.75 | 272.5 | 1.29 | 7.6E+05 |
| 13 | 0.5 | 27.5 | 1.58 | 3.0E+05 |
| 14 | 0.25 | 150.0 | 1.87 | 4.8E+05 |
| 15 | 0.75 | 150.0 | 1.87 | 4.8E+05 |

The vials were stoppered and capped (screw cap) before being placed at $+37°$ C. for 1 week of thermochallenge and later placed at $+4°$ C. until it was practical to assay them.

Assay of MVA

Assay plates (96 well) were seeded with BHK-21 cells (100 µl per well, $10^5$ cells/ml). Cells were diluted in DMEM supplemented with 10% FBS, and 1% PS. The plates were placed at $+37°$ C., $+5\%$ $CO_2$ for 1-2 hours.

A 10 fold dilution series of the formulated MVA samples was prepared (in the same growth media) ranging from 1 in 10 to 1 in 10,000. Each dilution series was prepared 5 times. 100 µl of each dilution was applied to individual wells containing BHK-21 cells (described above).

On 6 d p.i. the wells were scored for presence or absence of CPE and $TCID_{50}$ calculated. These were then used to estimate the concentration of infectious MVA per ml in the thermo-challenged vials.

Subsequently, a 2 fold dilution series of the formulated MVA samples was prepared ranging from 1 in 2,000 to 1 in 32,000. These dilutions were assayed separately but as before.

Results

Figure 17:
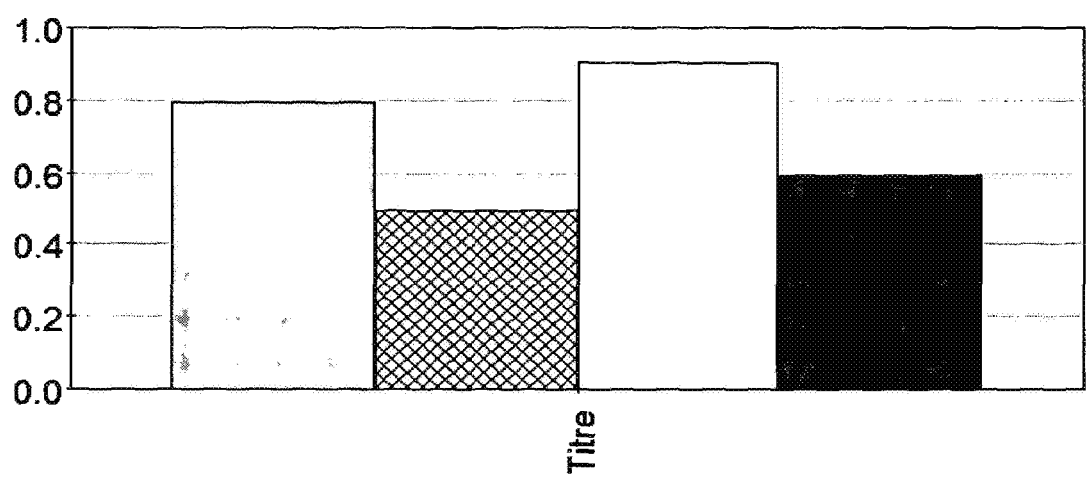
FIG. 17 summarises the statistics of the model used to represent the data in Example 10.

Raw data collected in this investigation are shown in Table 7 above. Responses ranged from $7.6 \times 10^4$ to $7.6 \times 10^5$ $TCID_{50}$/ml, or 7.4-74.0% of starting titre (see Table 7). The model generated from this data scored reasonably on all four model assessment parameters ($R^2 = 0.79$, $Q^2 = 0.49$, Model Validity=0.90, Reproducibility=0.59) (see FIG. 17).

Figure 18:
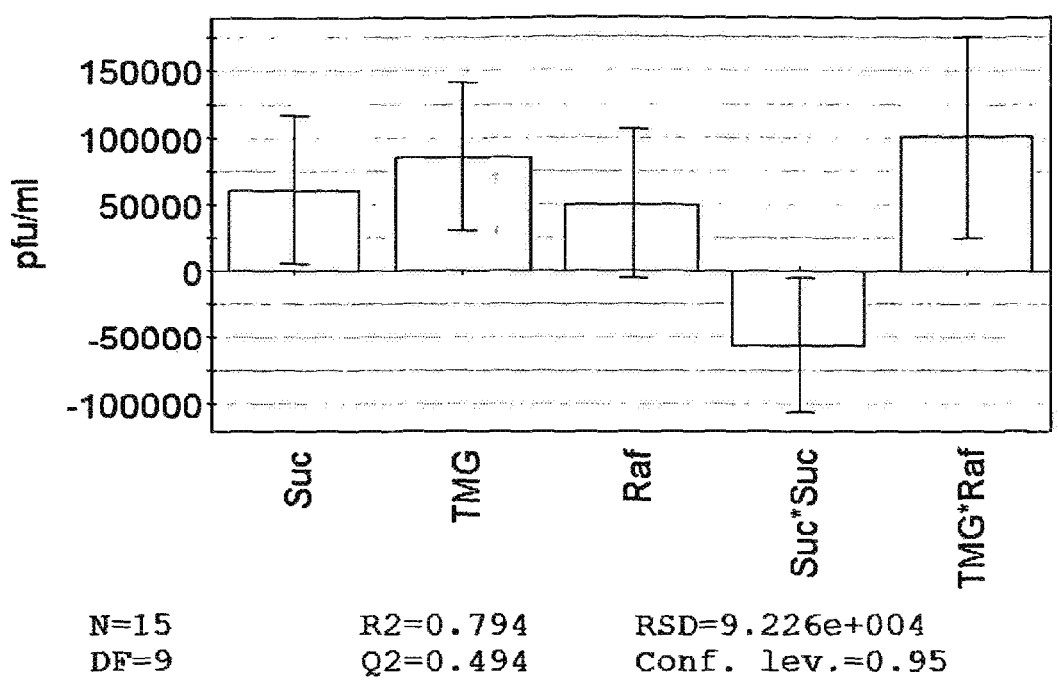
FIG. 18 shows terms retained in the model after fine-tuning in Example 10. Error bars not crossing the origin indicate a significant factor at the 95% C.I.

Sucrose, TMG and raffinose were all predicted to have $1^{st}$ order positive effects on viral recovery over the concentration range tested. Although, the raffinose effect was only significant at the 90% C.I. it was retained in the model as it improved the strength of the model and was required to preserve the model hierarchy. This was required because an interaction of TMG and raffinose was also predicted. Finally, a $2^{nd}$ order non-linear effect of sucrose was observed. See FIG. 18 for a summary of retained coefficients in the model.

Figure 19:
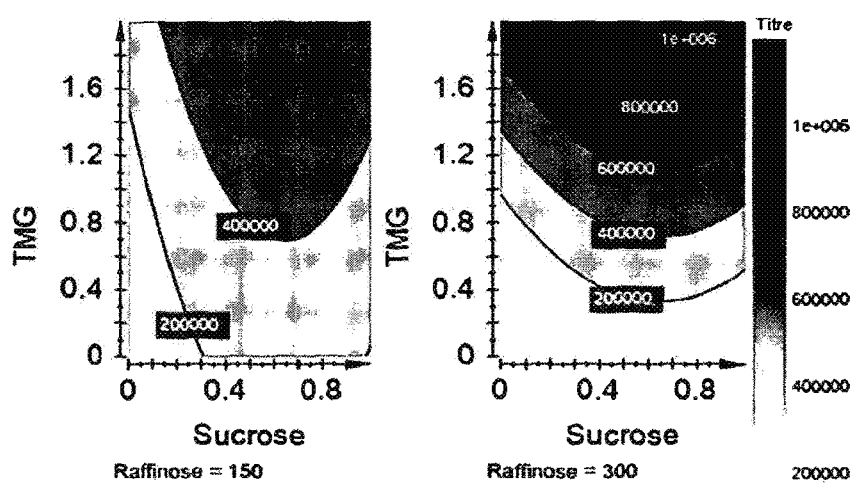
FIG. 19 is a surface response plot of the predicted recovered viral titre in formulations of TMG and mannitol in Example 10.

FIG. 19 is of a 4D contour plot that illustrates the interactions clearly. The optimum Sucrose concentration can be seen to be consistently between 0.6 and 0.8M, no other excipients significantly alter this. In general the higher the TMG concentration the greater the recovery of viral activity.

Figure 20:
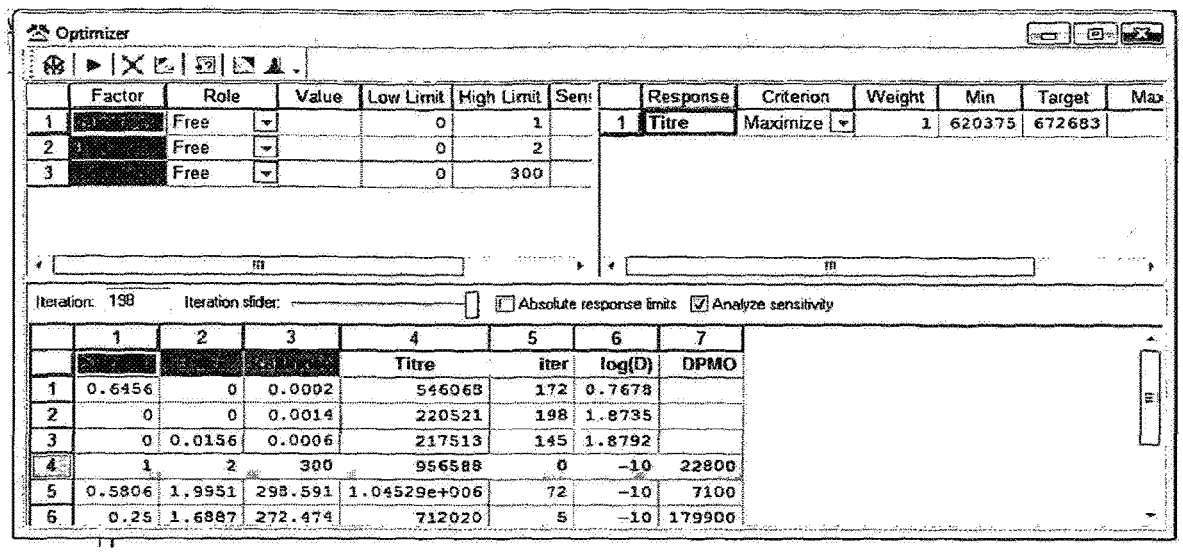
FIG. 20 is a screen capture of settings and outputs from the optimum predictions based on the model of the data in Example 10, generated using Monte-Carlo simulations. Highlighted formulation (line 4) is the optimum identified.

Monte-Carlo simulations (shown in FIG. 20) point to the extreme of the tested range for an optimum (1M Sucrose, 1M TMG, 300 mM Raffinose). This suggests that the optimum formulation is not covered by the tested range. However, the simulations predict that formulations close to this optimum should yield recovered viral activity of 94% starting titre.

Example 11

Materials

| Chemical | Supplier | Catalogue No. | Lot no. |
|---|---|---|---|
| 20x SSC | Sigma | S6639 | 020M8404 |
| Dimethyl sulfone | Sigma | M81705 | 0001452516 |
| Dimethyl sulfoxide | Sigma | D1435 | |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Raffinose | Sigma | R0250 | 050M0053 |
| Sucrose | Sigma | 16104 | SZB90120 |
| Water | Sigma | W3500 | 8M0411 |

| Biological | Supplier | Catalogue No. |
|---|---|---|
| Adenovirus | Vector Biolabs | Ad-CMV-GFP |
| HEK 293 | ECACC | 85120602 |

| Other | Supplier | Catalogue No. |
|---|---|---|
| 5 ml glass vials | Adelphi Tubes | VCD005 |
| 14 mm freeze drying stoppers | Adelphi Tubes | FDIA14WG/B |
| 14 mm caps | Adelphi Tubes | CWPP14 |

| Equipment | Manufacturer | Equipment No. |
|---|---|---|
| HERA safe class II cabinet | Thermo Fisher | EQP# 011 & 012 |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods

Design of Experiment

Figure 21:
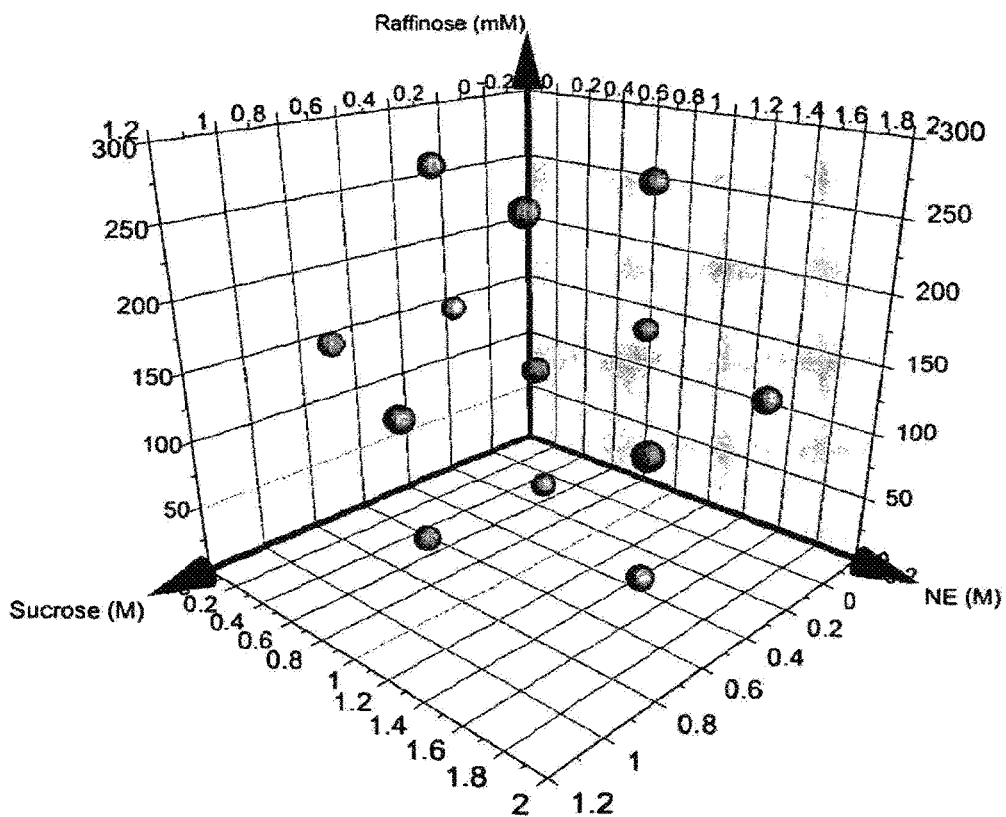
FIG. 21 shows a 3D representation of the design space in Example 11. Spheres represent formulations within the design space that are tested. This design is a Doehlert RSM design.

MODDE 9.0 (Umetrics) was used to generate a Doehlert experimental design (see FIG. 21), as described in Example 9. Thus, MSM was tested at seven levels, whilst sucrose was tested at five and raffinose at three. This model retains the ability to model for second order effects and interactions. The design included three factors and three replicate centre-points resulting in fifteen test samples.

Sucrose was tested between 0 and 1M. Raffinose was tested over a range of 0 to 300 mM although the nature of the Doehlert design meant that tested levels did not include 0 mM. Instead the following ranges were tested: 27.5, 150.0, and 272.5 mM. MSM was tested over a linear range of 0 to 2M.

Stability of Adenovirus in a Liquid Setting

Recombinant Adenovirus expressing enhanced GFP under a CMV promoter, with a titre (pre-freeze) of $6.7 \times 10^5$ pfu/ml in SSC, was removed from storage at −80° C. and allowed to thaw. Subsequently, 50 μl aliquots of virus were added to 15, 5 ml, glass vials. To each vial 250 μl of an excipient blend was admixed. The excipient blend formulations once mixed with virus are described in Table 8 and were made up in SSC.

TABLE 8

| Formulation No. | Sucrose (M) | Raffinose (mM) | MSM (M) | Recovered Titre (pfu/ml) |
|---|---|---|---|---|
| 1 | 0.25 | 150.0 | 0.13 | 204000 |
| 2 | 0.75 | 150.0 | 0.13 | 282000 |
| 3 | 0.5 | 272.5 | 0.42 | 306000 |
| 4 | 0.25 | 27.5 | 0.71 | 186000 |
| 5 | 0.75 | 27.5 | 0.71 | 360000 |
| 6 | 0 | 150.0 | 1.00 | 114000 |
| 7 | 0.5 | 150.0 | 1.00 | 240000 |
| 8 | 0.5 | 150.0 | 1.00 | 204000 |
| 9 | 0.5 | 150.0 | 1.00 | 186000 |
| 10 | 1 | 150.0 | 1.00 | 270000 |
| 11 | 0.25 | 272.5 | 1.29 | 168000 |
| 12 | 0.75 | 272.5 | 1.29 | 294000 |
| 13 | 0.5 | 27.5 | 1.58 | 90000 |
| 14 | 0.25 | 150.0 | 1.87 | 48000 |
| 15 | 0.75 | 150.0 | 1.87 | 198000 |

The vials were stoppered and capped (screw cap) before being placed at +37° C. for 1 week of thermochallenge and later placed at +4° C. until it was practical to assay them. The adenovirus assay was as described in Example 9.

Results

Figure 22:
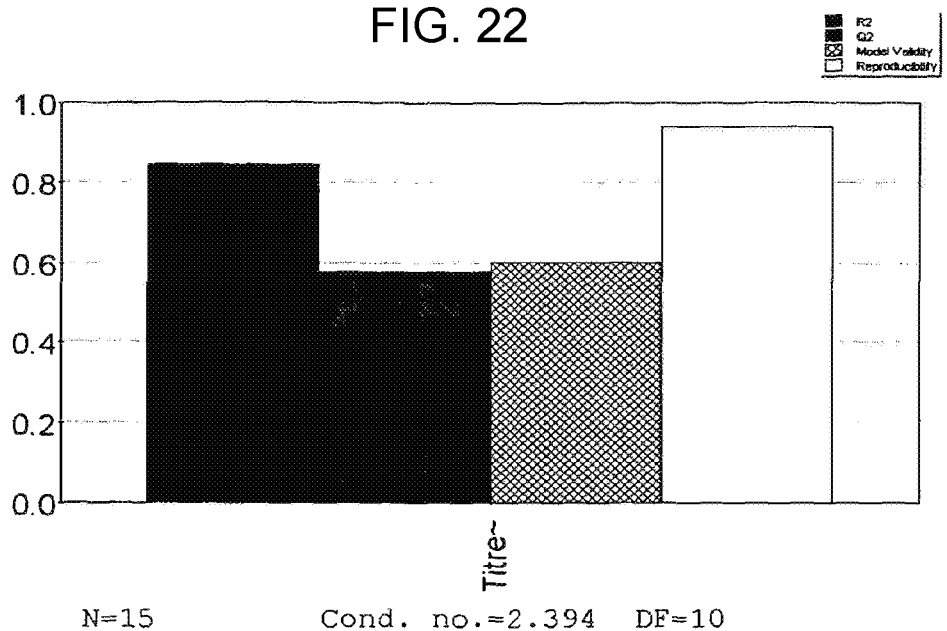
FIG. 22 summarises the statistics of the model used to represent the data in Example 11.

The raw data are set out in Table 8. An analysis of the data generated a relatively strong model (see FIG. 22). $R^2$ (0.84) indicated good significance, Reproducability (0.94) was high, and Model Validity (0.60) was significantly above the level (0.25) that indicates model problems.

Figure 23:
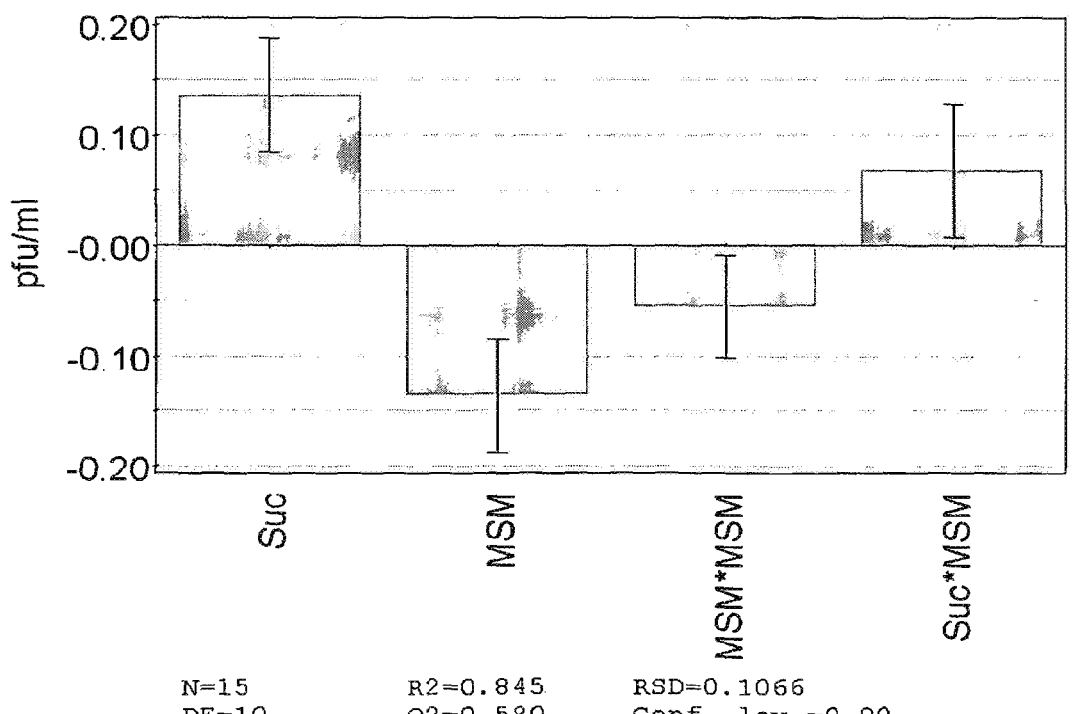
FIG. 23 shows terms retained in the model after fine tuning in Example 11. Error bars not crossing the origin indicate a significant factor at the 90% C.I.

FIG. 23 shows the retained model coefficients after model fine tuning. Both MSM and sucrose are significant factors as 1st order effects (wth C.I.=95%). No other significant factors were detected at the 95% confidence level. However, analysis during fine tuning suggested that there was some curvature. A stronger model was obtained by including two other factors that were only significant at the 90% confidence level. Firstly, a 2nd order effect of MSM and an interaction between MSM and sucrose. No effect of raffinose was observed in this analysis, and it was eliminated from the model.

Figure 24:
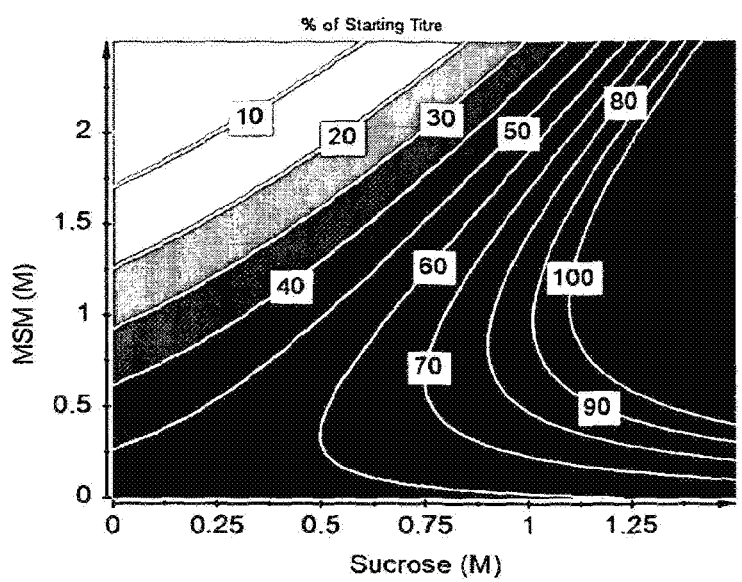
FIG. 24 shows a contour plot of the model describing the recovery of adenovirus formulated in MSM, sucrose, and raffinose and thermo-challenged at +37° C. for 1 week in Example 11. Raffinose is not shown as a variable as it had no effect on titre, and was thus eliminated from the model. The response shown is recovered viral titre as a percentage of the positive control (starting titre).).

A 3D plot of the model (see FIG. 24) demonstrates that increasing sucrose concentration results in increased recovered viral activity. The tested range here does not include the optimum sucrose concentration. At high sucrose levels, an intermediate MSM concentration (~1M) enhances the protective effect. In general, the more sucrose present the higher the optimum MSM concentration.

Figure 25:
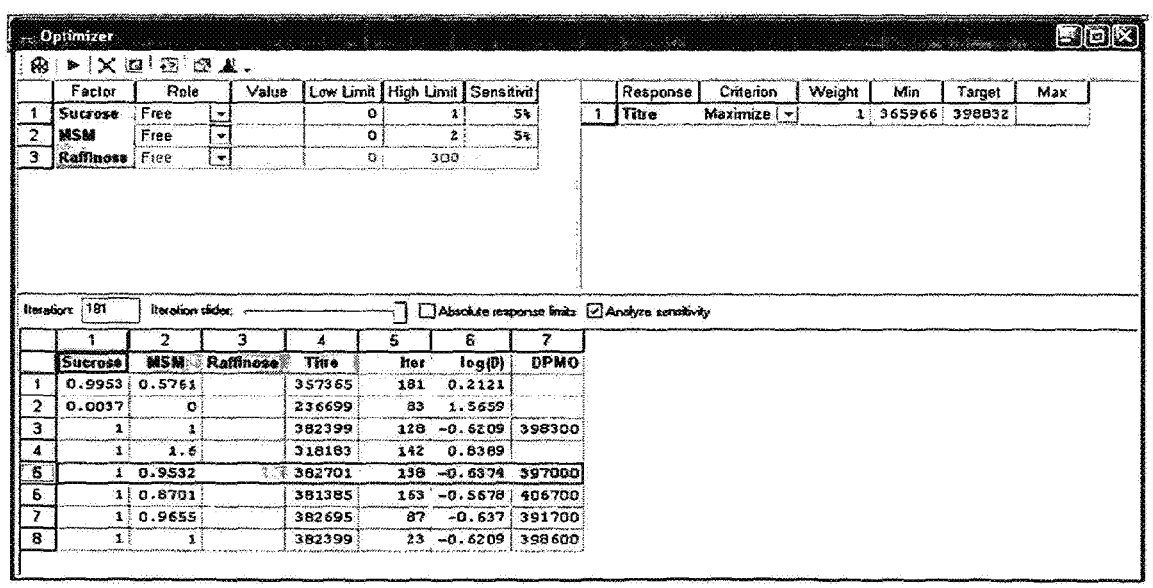
FIG. 25 shows a screen capture of settings and outputs from the optimum predictions based on the model of the data in Example 11, generated using Monte-Carlo simulations. The predicted optimum highlighted sucrose concentration of 1M and an MSM concentration of 0.95M.

Monte-Carlo simulations (FIG. 25) were used to predict an optimum concentration of the excipients. An optimum of 1M sucrose and 0.95M MSM was identified. Since, raffinose has no effect on the model it is not required in the optimum formulation. However, if raffinose was required in the formulation for any other reason it would not have a negative effect either. The optimum formulation is predicted to yield a recovered viral activity of $3.8 \times 10^5$ pfu/ml or 88.4% of initial virus titre (compared to a positive control of $4.3 \times 10^5$ pfu/ml).

Example 12

Materials

| Chemical | Supplier | Product Code | Lot No. |
|---|---|---|---|
| 20x SSC | Sigma | S6639 | 020M8404 |
| Dimethyl glycine | Sigma | D1156 | 077K1856 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Raffinose | Sigma | R0250 | 050M0053 |
| Sucrose | Sigma | 16104 | SZB90120 |
| Water | Sigma | W3500 | 8M0411 |

-continued

| Materials | | |
|---|---|---|
| Chemical | Supplier Product Code | Lot No. |
| Biological | Supplier | Product Code |
| Adenovirus | Vector Biolabs | Ad-CMV-GFP |
| HEK 293 | ECACC | 85120602 |
| Other | Manufacturer | Product Code |
| 5 ml glass vials | Adelphi Tubes | VCD005 |
| 14 mm freeze drying stoppers | Adelphi Tubes | FDIA14WG/B |
| 14 mm caps | Adelphi Tubes | CWPP14 |
| Equipment | Manufacturer | Equipment No. |
| HERA safe class II cabinet | Thermo Fisher | EQP# 011 & 012 |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods
Design of Experiment

Figure 26:
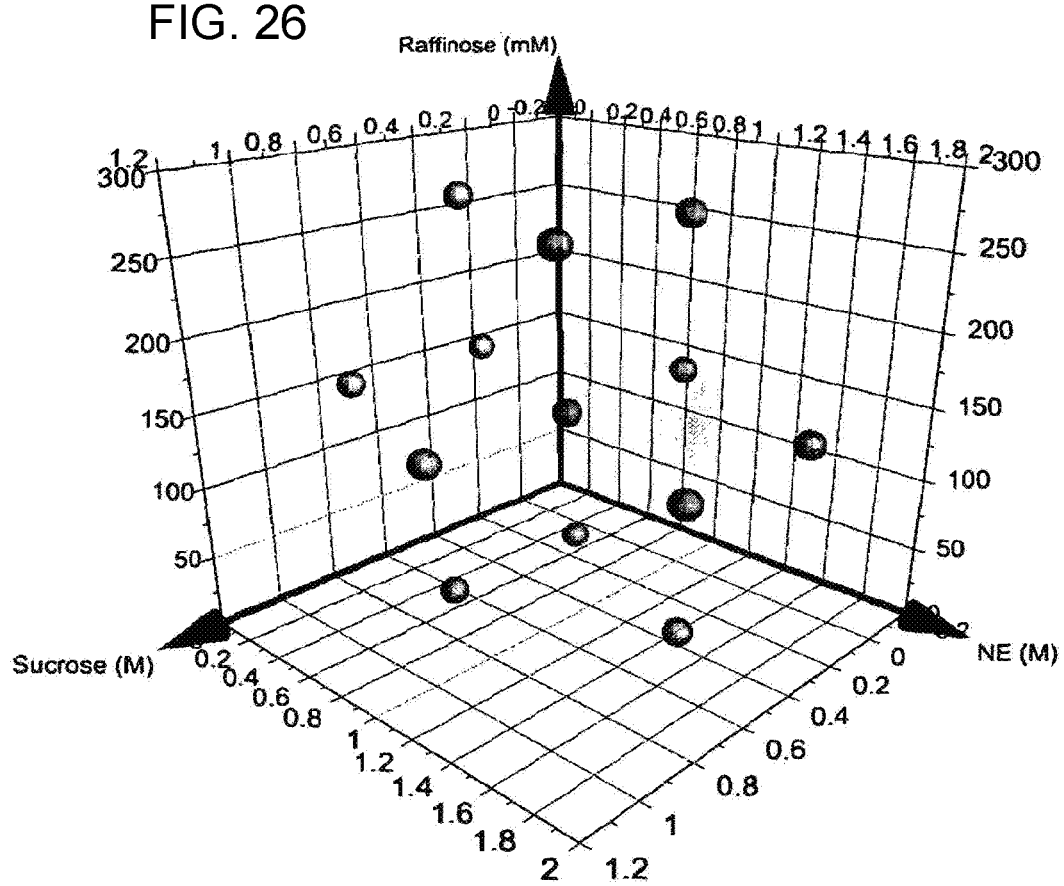
FIG. 26 shows a 3D representation of the design space in Example 12. Spheres represent formulations within the design space that are tested. This design is a Doehlert RSM design.

MODDE 9.0 (Umetrics) was used to generate a Doehlert experimental design (see FIG. 26), as described in Example 9. DMG was tested at seven levels, whilst sucrose was tested at five and raffinose three. This model retains the ability to model for second order effects and interactions. The design included three factors and three replicate centre-points resulting in fifteen test samples.

Sucrose was tested between 0 and 1M. Raffinose was tested over a range of 0 to 300 mM although the nature of the Doehlert design meant that tested levels did not include 0 mM. Instead the following ranges were tested: 27.5, 150.0, and 272.5 mM. DMG was tested over a linear range of 0 to 2M.

Stability of Adenovirus in a Liquid Setting

Recombinant Adenovirus expressing enhanced GFP under a CMV promoter, with a titre (pre-freeze) of $6.7 \times 10^5$ pfu/ml in SSC, was removed from storage at −80° C. and allowed to thaw. Subsequently, 50 µl aliquots of virus were added to 15, 5 ml, glass vials. To each vial 250 µl of an excipient blend was admixed. The excipient blend formulations once mixed with virus are described in Table 9 and were made up in SSC.

TABLE 9

| Formulation No. | Sucrose (M) | Raffinose (mM) | DMG (M) | Titre (pfu/ml) |
|---|---|---|---|---|
| 1 | 0.25 | 150.0 | 0.13 | 1.1E+05 |
| 2 | 0.75 | 150.0 | 0.13 | 2.2E+05 |
| 3 | 0.5 | 272.5 | 0.42 | 3.8E+05 |
| 4 | 0.25 | 27.5 | 0.71 | 2.0E+05 |
| 5 | 0.75 | 27.5 | 0.71 | 2.6E+05 |
| 6 | 0 | 150.0 | 1.00 | 2.2E+05 |
| 7 | 0.5 | 150.0 | 1.00 | 2.2E+05* |
| 8 | 0.5 | 150.0 | 1.00 | 3.1E+05 |
| 9 | 0.5 | 150.0 | 1.00 | 3.4E+05 |
| 10 | 1 | 150.0 | 1.00 | 4.1E+05 |
| 11 | 0.25 | 272.5 | 1.29 | 2.5E+05 |
| 12 | 0.75 | 272.5 | 1.29 | 3.7E+05 |
| 13 | 0.5 | 27.5 | 1.58 | 3.7E+05 |
| 14 | 0.25 | 150.0 | 1.87 | 2.5E+05 |
| 15 | 0.75 | 150.0 | 1.87 | 3.3E+05 |

*indicates an outlier eliminated from the model

The vials were stoppered and capped (screw cap) before being placed at +37° C. for 1 week of thermochallenge and later placed at +4° C. until it was practical to assay them. The adenovirus assay was as described in Example 9.

Results

Figure 27:
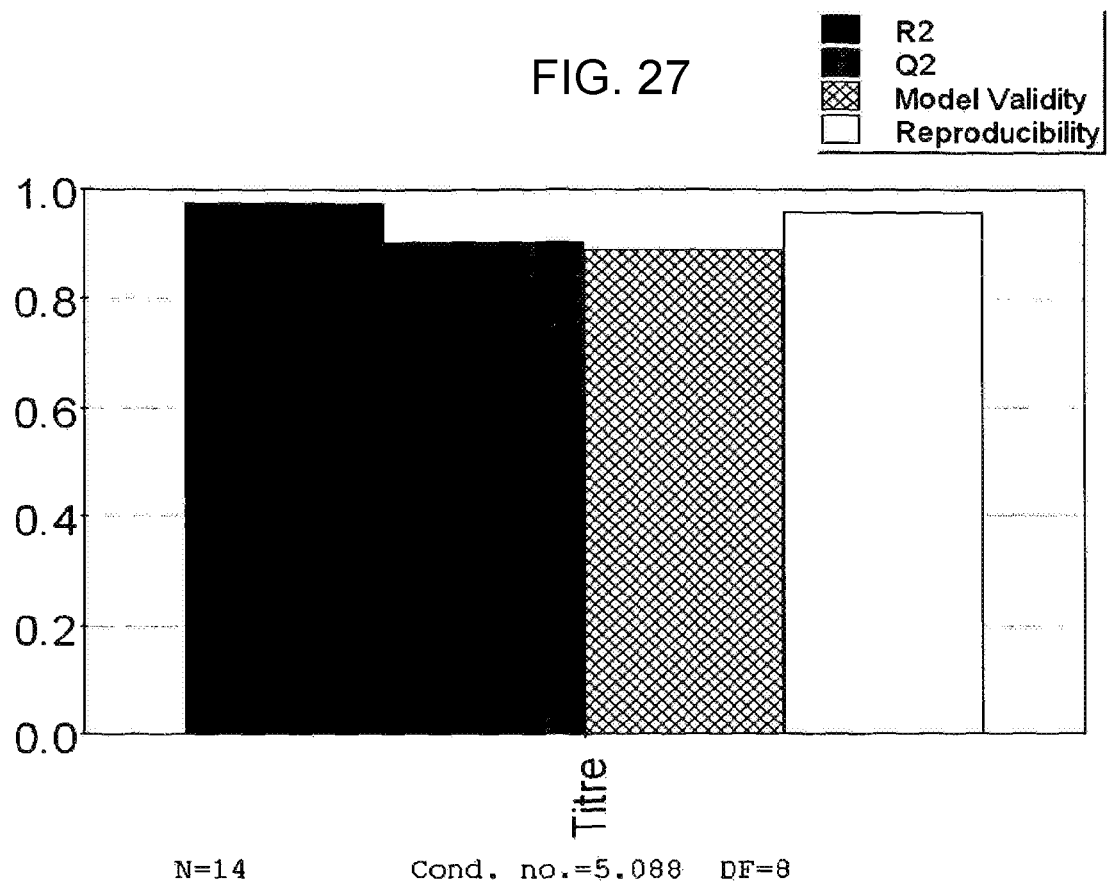
FIG. 27 summarises statistics of the model used to represent the data in Example 12.

A very strong model was generated from this data (see Table 9). The model scored highly with all four indicators ($R^2$=0.97, $Q^2$=0.90, Model Validity=0.89, Reproducability=0.96) (see FIG. 27). The model was enhanced during fine tuning by the elimination of one replicate. This formulation was flagged by the software as an obvious outlier.

Figure 28:
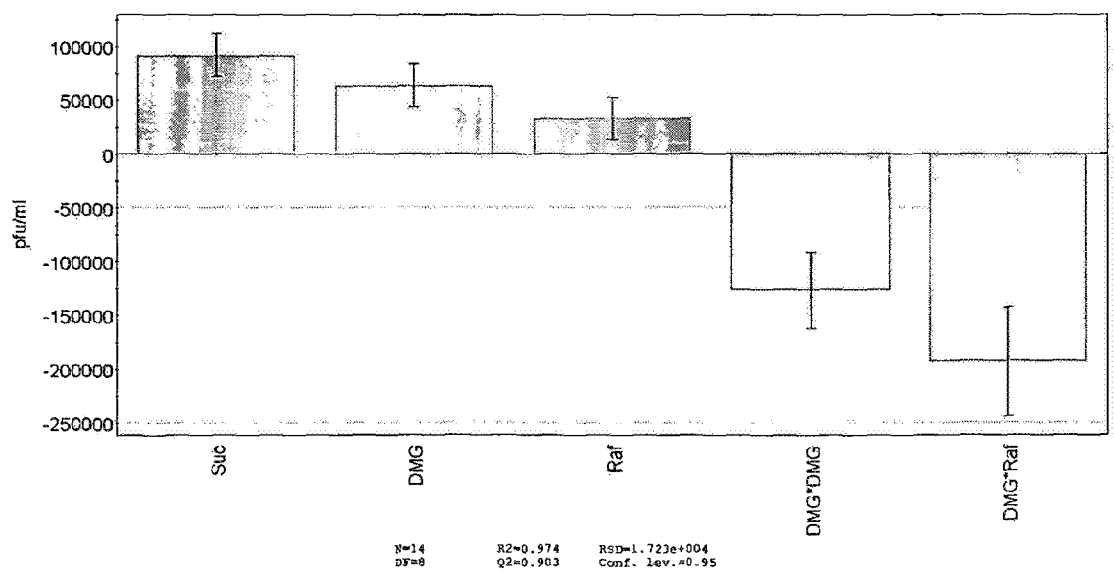
FIG. 28 shows terms retained in the model in Example 12 after fine tuning. Error bars not crossing the origin indicate a significant factor at the 95% C.I.

All three excipients in the formulation were shown to be significant factors in the model (see FIG. 28). Sucrose and raffinose only had 1st order effects whereas DMG had both 1st and 2nd order effects. In addition, there was an interaction between raffinose and DMG.

Figure 29:
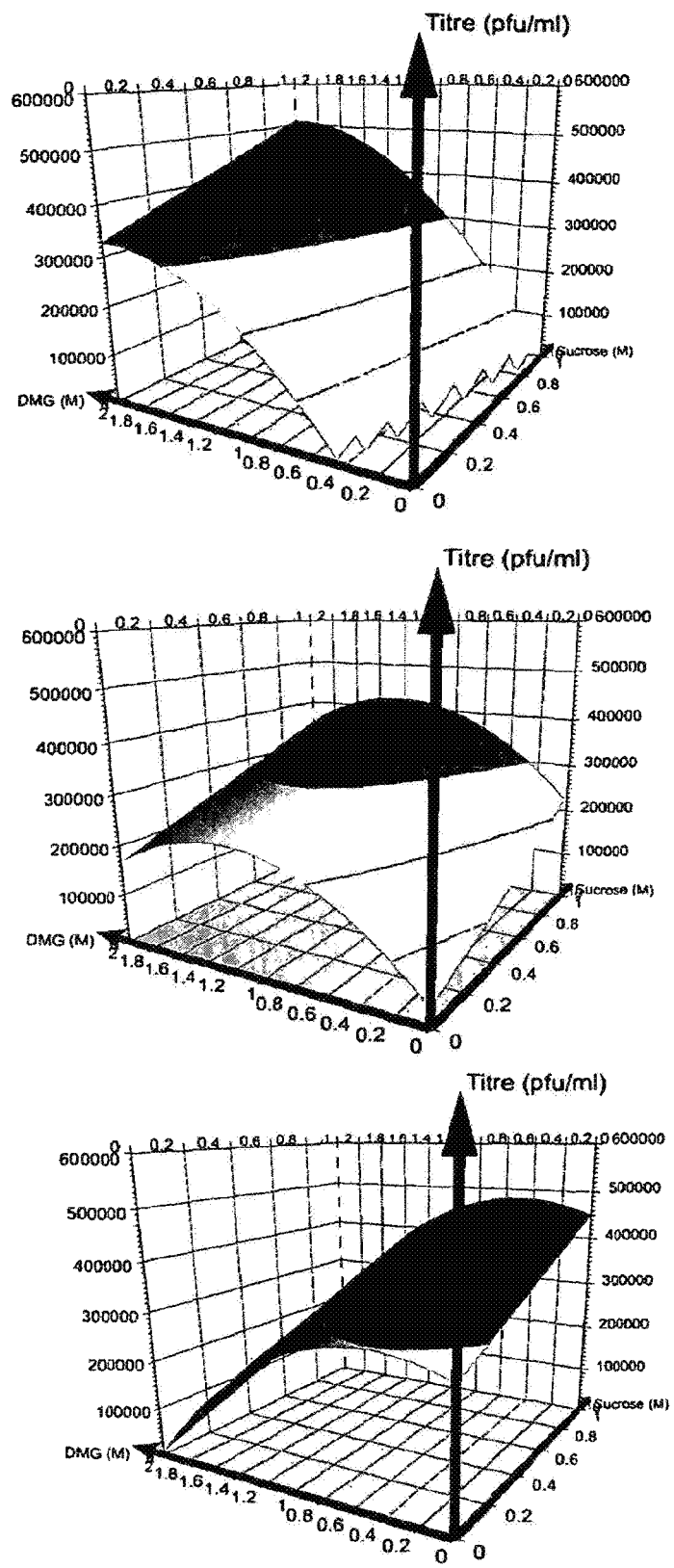
FIG. 29 is a surface response plot of predicted viral titre using the model of Example 12 in formulations of DMG and sucrose at three different levels of raffinose, namely: "Low"=raffinose at 0 mM, "Mid"=raffinose at 150 mM, "High"=raffinose at 300 mM.

FIG. 29 shows that the optimum sucrose concentration is beyond that tested. However, it is unlikely the sucrose concentration would be significantly increased due to constraints on the osmolarity of the product. At some levels DMG enhances the protective effect of the formulation, and raffinose alters the optimum DMG concentration for this purpose.

Figure 30:
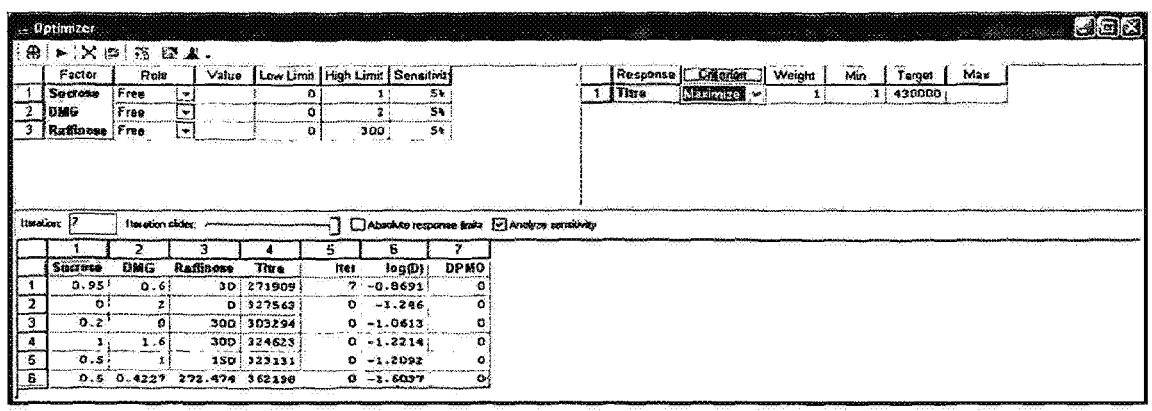
FIG. 30 shows a screen capture of settings and outputs from the optimum predictions based on the model of the data in Example 12, generated using Monte-Carlo simulations. The predicted optima highlighted is sucrose concentration of 0.5M, DMG concentration 0.4M and raffinose concentration of 272.5 mM.

Monte-Carlo simulations were used to predict an optimum formulation (see FIG. 30). The program was set to maximise recovered viral activity to a limit of $4.3 \times 10^5$ pfu/ml (the titre of a positive control). The predicted optimum formulation was 0.5M Sucrose, 0.4M DMG, 272 nM Raffinose and this was predicted to yield a titre of $3.6 \times 10^5$ pfu/ml or 84% of starting titre (based on the positive control).

Figure 31A:
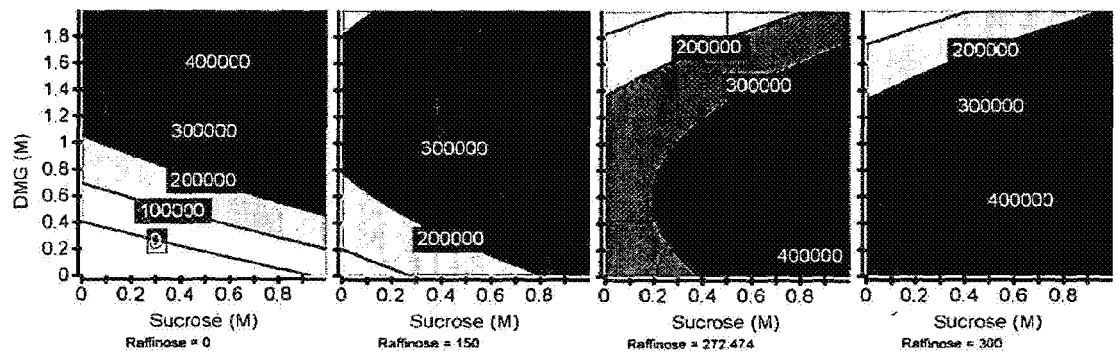
FIG. 31A-B shows an optimum region plot using the model derived from Example 12.
Figure 31B:
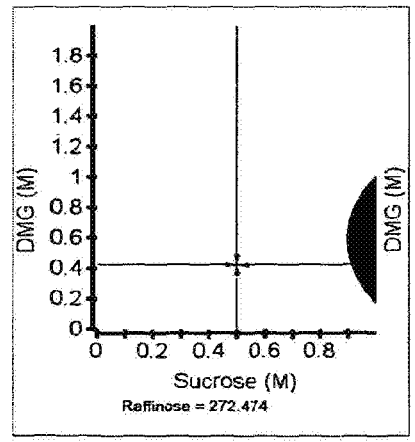

FIG. 31a shows an alternative way of looking at the data. A contour plot shows DMG concentration plotted against sucrose concentration at a number of different raffinose concentrations. The plot shows the darker region (higher recovery of virus activity) moves down the Y-axis (DMG concentration) as raffinose is increased. A black cross marks the predicted optimum formulation. FIG. 31b shows the region where recovery is predicted to be 100% or greater.

Example 13

| Materials | | | |
|---|---|---|---|
| Chemical | Supplier | Product Code | Lot No. |
| Dimethyl glycine | Sigma | D1156 | 077K1856 |
| Dulbeccos Modified Eagles Medium | Sigma | D5796 | RNBB1139 |
| Foetal Bovine Serum | Sigma | F7524 | 109K3395 |
| Raffinose | Sigma | R0250 | 050M0053 |
| Sucrose | Sigma | 16104 | SZB90120 |
| Water | Sigma | W3500 | 8M0411 |
| Biological | Supplier | | Product Code |
| Adenovirus | Vector Biolabs | | Ad-CMV-GFP |
| HEK 293 | ECACC | | 85120602 |
| Other | Supplier | | Product Code |
| 5 ml glass vials | Adelphi Tubes | | VCD005 |
| 14 mm freeze drying stoppers | Adelphi Tubes | | FDIA14WG/B |
| 14 mm caps | Adelphi Tubes | | CWPP14 |

-continued

| Materials | | |
|---|---|---|
| Chemical | Supplier Product Code | Lot No. |
| Equipment | Manufacturer | Equipment No. |
| Dryer | | |
| HERA safe class II cabinet | Thermo Fisher | EQP# 011 & 012 |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods

Recombinant adenovirus expressing enhanced GFP under a CMV promoter, with a titre (after thawing) of $10.2 \times 10^5$ pfu/ml in PBS, was removed from storage at −80° C. and allowed to thaw. Subsequently, 50 µl aliquots of virus were added to 15, 5 ml, glass vials. To each vial 250 µl of an excipient blend was admixed. The excipient blend formulations once mixed with virus are described in Table 10 and were made up in PBS.

From this point onward the following treatment names are used:

TABLE 10

| Formulation Name | Buffer | Raffinose (mM) | Sucrose (M) | DMG (M) |
|---|---|---|---|---|
| Buffer | PBS | 0 | 0 | 0 |
| Raffinose | PBS | 100 | 0 | 0 |
| Sucrose | PBS | 0 | 1 | 0 |
| Sugars | PBS | 100 | 1 | 0 |
| NE | PBS | 0 | 0 | 0.7 |
| Best | PBS | 100 | 1 | 0.7 |

"Buffer" = PBS buffer only no excipients
"Sucrose" = 1M Sucrose in PBS
"Raffinose" = 100 mM Raffinose in PBS
"Sugars" = 1M Sucrose, 100 mM Raffinose in PBS,
"NE" = 0.7M DMG in PBS,
"Best" = 1M Sucrose, 100 mM Raffinose, 0.7M DMG in PBS.

The vials were stoppered and capped (screw cap) before being thermally challenged under the conditions set out in Table 11. At appropriate time points, an adenovirus assay was carried out as described in Example 9.

Results

Many data points gathered were below the detection threshold of the assay (see Table 11).

For convenience these data points have been assigned the threshold value as this is the maximum possible value they could have. It is likely that this will have little effect on the interpretation of the results as any formulation yielding such low recovery of viral activity is of little practical use as anything other than a comparator. The detection threshold for this assay is 600 pfu/ml which equates to 0.03% recovered activity.

Figure 32:
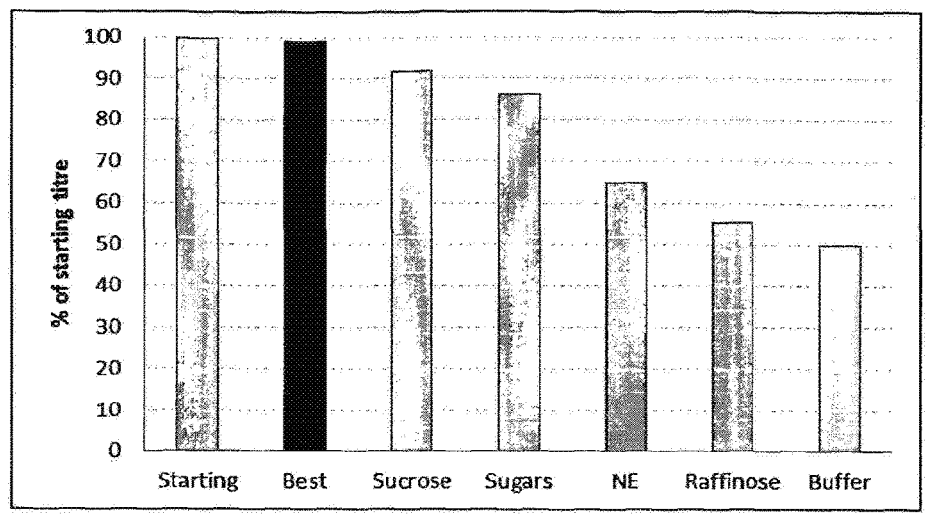
FIG. 32 shows the recovered viral activity from various formulations after 6 months storage at +4° C. in Example 13.

Only one time point was tested for samples held at +4° C. The yield of virus activity after 6 months at this temperature can be seen in FIG. 32. The buffer only treatment gave recovery of 50.1% starting titre and a clear indication that adenovirus used is inherently reasonably stable in this liquid setting. This finding also shows the need for accelerated stability studies.

The "sucrose" treatment recovered 92.1% activity which after 6 months is a major improvement on buffer alone. "Raffinose" in contrast only yielded 55.5%, a slight improvement on "Buffer Alone" but worse than "Sucrose". The combined "Sugars" treatment gave a recovered virus activity of only 86.4%.

The DMG only treatment ("NE") preserved only 65.1% or virus activity, but when used in concert with the sugars a recovered activity of 99.3% was observed. This finding is close to zero loss of adenovirus at +4° C. after 6 months.

Figure 33:
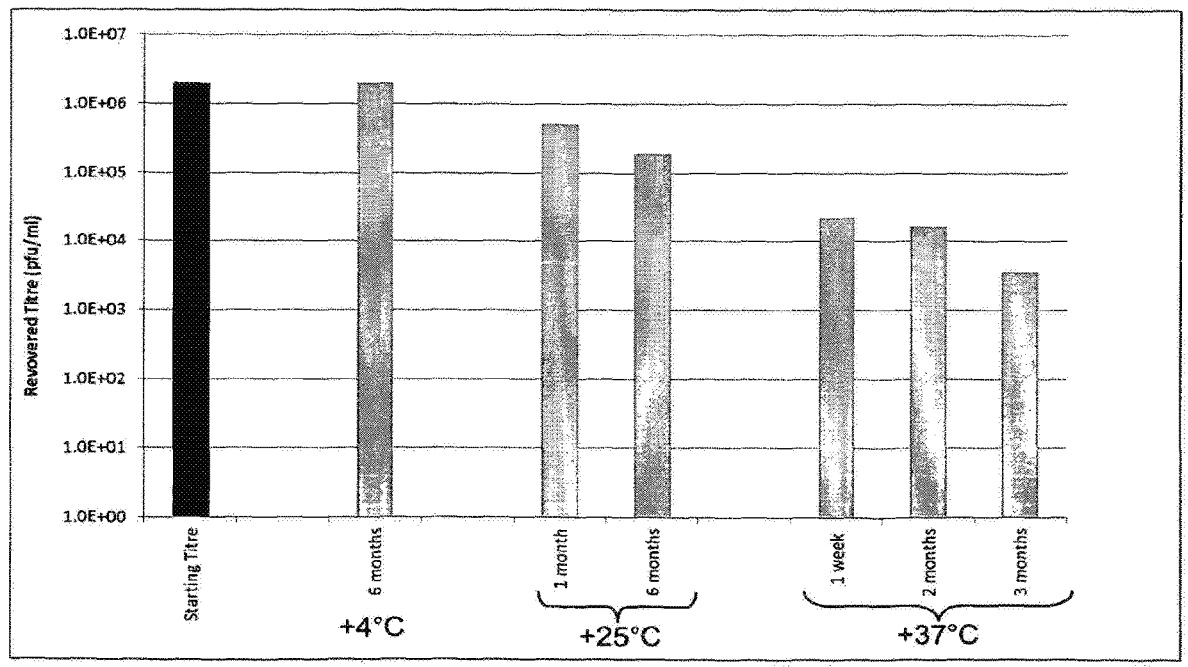
FIG. 33 shows recovered viral activity for the 'best' formulation in Example 13 comprising 1M sucrose, 100 mM raffinose and 0.7M DMG at each time point and thermal challenge.

The recovered viral activity in this "Best" formulation at each time-point and temperature challenge is shown in FIG. 33. As previously discussed after 6 months at +4° C. there is close to zero loss.

Figure 34:
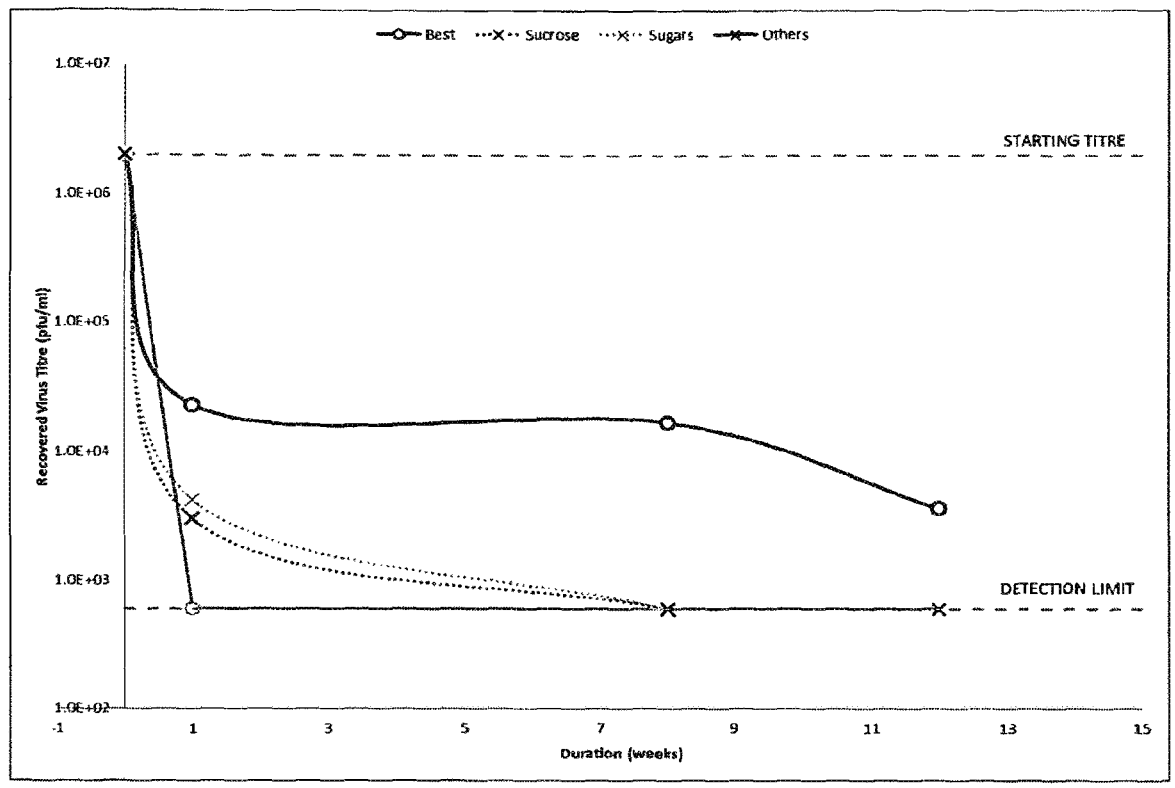
FIG. 34 shows reduction in recovered viral activity over time at +37° C. thermal challenge in various formulations in Example 13.

The results (see Table 11 and FIG. 34) at the +25° C. and +37° C. thermo-challenges demonstrate that the "Best" formulation is more effective in stabilising the adenovirus than its constituent components.

Example 14

| Materials | | | |
|---|---|---|---|
| Chemical | Supplier | Product Code | Lot No. |
| 20x SSC | Sigma | S6639 | 020M8404 |
| Dimethyl glycine | Sigma | D1156 | 077K1856 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Water | Sigma | W3500 | 8M0411 |
| Biological | Supplier | | Product Code |
| BHK-21 cell line | ECACC | | CB2857 |
| MVA | ATCC | | VR-1508 |

TABLE 11

| Thermal Challenge | | Formulation | | | | | |
|---|---|---|---|---|---|---|---|
| Temperature | Duration | Best | Sucrose | Raffinose | Sugars | NE | Buffer |
| +4° C. | 6 months | 2.0E+06 | 1.8E+06 | 1.1E+06 | 1.7E+06 | 1.3E+06 | 1.0E+06 |
| +25° C. | 1 month | 5.2E+05 | 1.9E+05 | 1.6E+05 | 2.0E+05 | 2.3E+05 | 7.2E+04 |
|  | 6 months | 1.9E+05 | 6.0E+02* | 6.0E+02* | 1.0E+05 | 3.0E+04 | 6.0E+02* |
| +37° C. | 1 | 2.3E+04 | 3.0E+03 | 6.0E+02* | 4.2E+03 | 6.0E+02* | 6.0E+02* |
|  | 8 | 1.7E+04 | 6.0E+02* | 6.0E+02* | 6.0E+02* | 6.0E+02* | 6.0E+02* |
|  | 12 | 3.6E+03 | 6.0E+02* | 6.0E+02* | 6.0E+02* | 6.0E+02* | 6.0E+02* |

*data-point below detection threshold

-continued

| Materials | | |
|---|---|---|
| Chemical | Supplier Product Code | Lot No. |
| Other | Manufacturer | Product Code |
| 2 ml glass vials | Adelphi Tubes | VCDIN2R |
| 13 mm freeze drying stoppers | Adelphi Tubes | FDW13 |
| Crimps | Adelphi Tubes | COTW13 |
| Equipment | Manufacturer | Equipment No. |
| HERA safe class II cabinet | Thermo Fisher | EQP# 011 & 012 |
| DMIL LED Inverted Microscope | Leica | EQP#062 |
| Binder $CO_2$ Incubator | Binder | EQP#014 |
| Forma 900 series −80° C, freezer | Thermofisher | EQP#015 |
| ATL-84-1 Atlion Balance | Acculab | EQP#088 |
| IP250 37° C. Incubator | LTE | EQP#016 |

Methods
Design of Experiment

Figure 35:
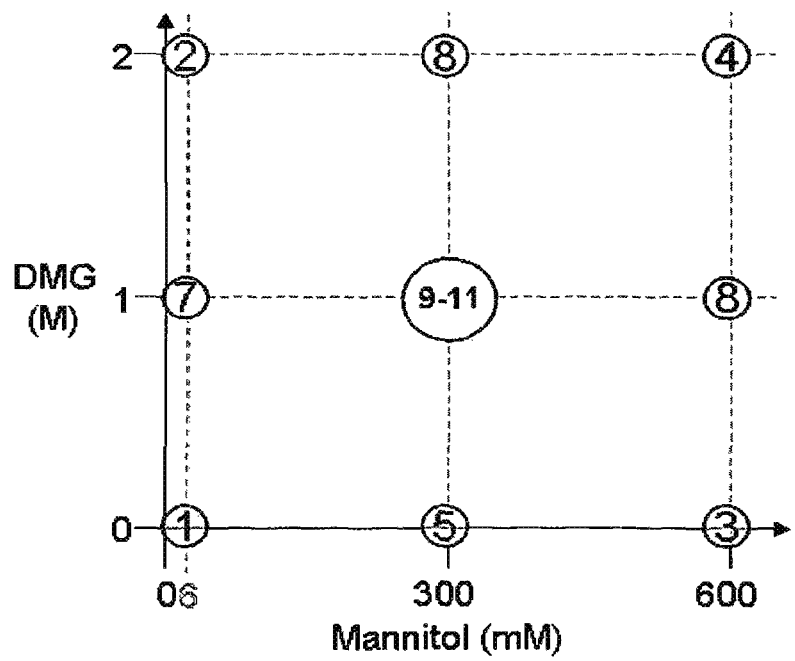
FIG. 35 shows a representation of the design space in Example 14. Numbered circles represent formulations within the design space that were tested. This design is a CCF RSM design.

MODDE 9.0 was used to generate a Central Composite Face-Centred (CCF) design. CCF designs are a form of Response Surface Modelling (RSM) design that tests only 3 levels of each factor but still supports a quadratic model (see FIG. 35). Unlike regular formulation designs non-significant factors can be eliminated from the analysis and so do not become a confounding factor.

Preparation of and Thermal Challenge of Formulated MVA in a Liquid Setting

MVA was recovered from storage at −80° C. and thawed. Subsequently, 50 μl aliquots of virus were added to 15, 5 ml, glass vials. To each vial 250 μl of an excipient blend was admixed. The excipient blend formulations once mixed with virus are described in Table 12 below and were made up in SSC. The vials were stoppered under vacuum, and capped (screw cap) before being placed at +37° C. for 1 week of thermochallenge and later placed at +4° C. until it was practical to assay them.

Assay of MVA

Assay plates (96 well) were seeded with BHK-21 cells (100 μl per well, $10^5$ cells/ml). Cells were diluted in DMEM supplemented with 10% FBS, and 1% PS. The plates were placed at +37° C., +5% $CO_2$ for 1-2 hours.

Meanwhile, a 10 fold dilution series of the formulated MVA samples was prepared (in the same growth media) ranging from 1 in 10 to 1 in 10,000. Each dilution series was prepared as 5 replicates. 100 μl of each dilution was applied to individual wells containing BHK-21 cells (described above).

On 6 d.p.i. the wells were scored for presence or absence of CPE and $TCID_{50}$ calculated. These were then used to estimate the concentration of infectious MVA per ml in the thermo-challenged vials.

Results

The crude $TCID_{50}$ data from this study is shown in Table 12.

TABLE 12

| Sample I.D. | DMG (M) | Mannitol (mM) | Titre ($TCID_{50}$/ml) |
|---|---|---|---|
| 1 | 0 | 6 | 1.90E+5 |
| 2 | 2 | 6 | 4.80E+3 |

TABLE 12-continued

| Sample I.D. | DMG (M) | Mannitol (mM) | Titre ($TCID_{50}$/ml) |
|---|---|---|---|
| 3 | 0 | 600 | 3.00E+4 |
| 4 | 2 | 600 | 4.80E+5 |
| 5 | 0 | 303 | 3.00E+5* |
| 6 | 2 | 303 | 3.00E+5 |
| 7 | 1 | 6 | 3.00E+4 |
| 8 | 1 | 600 | 3.00E+5 |
| 9 | 1 | 303 | 7.60E+5* |
| 10 | 1 | 303 | 1.90E+5 |
| 11 | 1 | 303 | 1.90E+5 |

*Data point excluded from model during fine tuning as an obvious outlier

Figure 36:
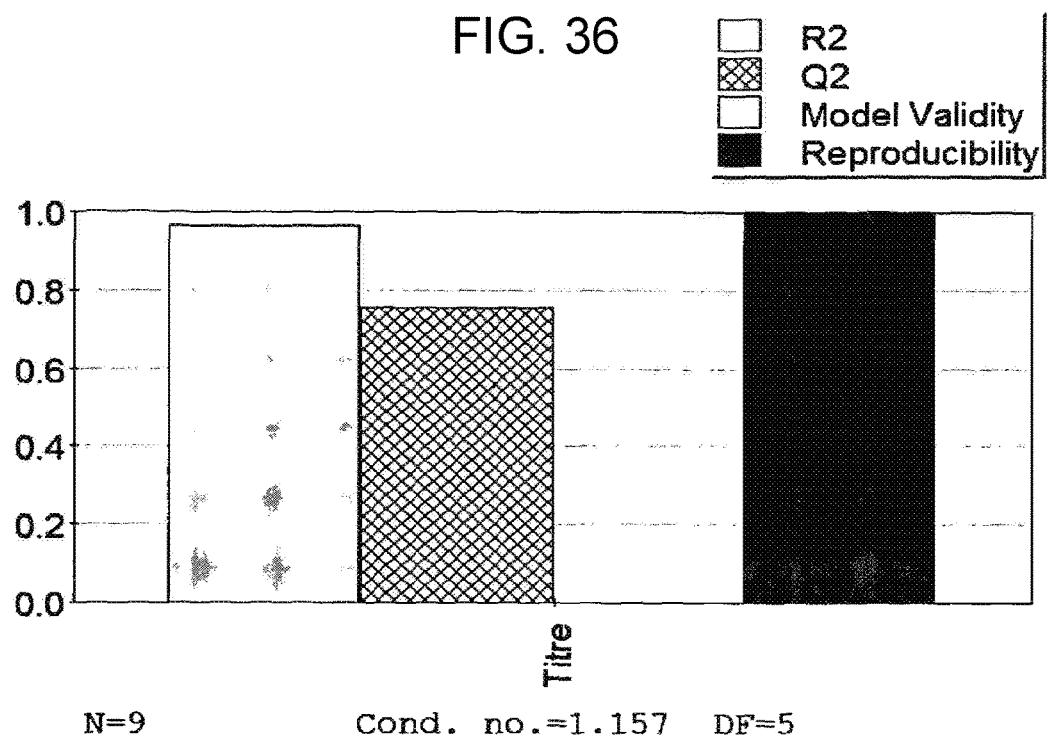
FIG. 36 summarises the statistics of the model used to represent the data in Example 14.
Figure 37:
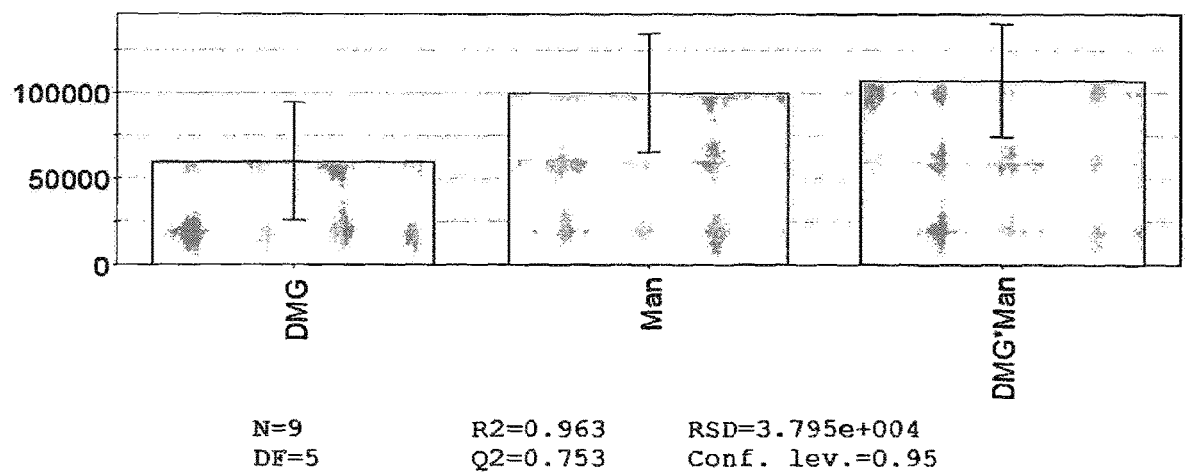
FIG. 37 shows terms retained in the model in Example 14 after fine tuning. Error bars not crossing the origin indicate a significant factor at the 95% C.I.
Figure 38:
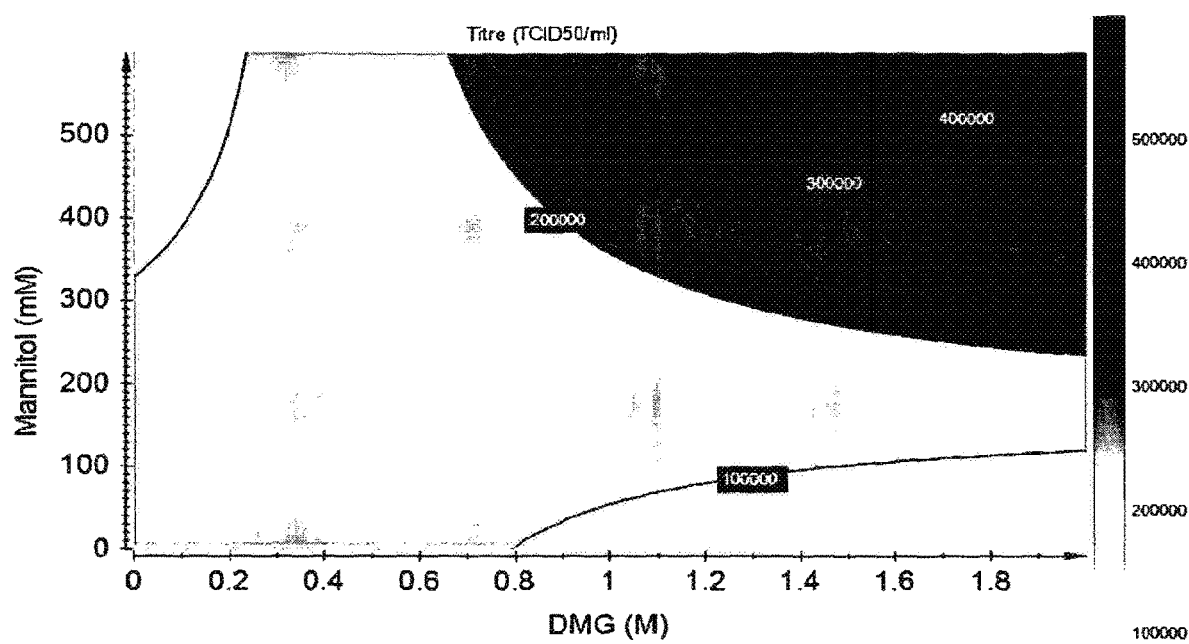
FIG. 38 shows a contour plot of the predicted recovered viral titre in formulations of DMG and mannitol in Example 14.

Responses varied from 0.5 to 74.1% of starting titre. The model predicts $1^{st}$ order effects of both excipients (see FIGS. 36 and 37). In the case of both DMG and mannitol, viral preservation is increased as concentration increases. This is clearly illustrated by the contour plot shown in FIG. 38. Additionally, an interaction between DMG and Mannitol was identified.

Monte-Carlo simulations suggest that with the high concentration of each excipient tested it can be expected to achieve over 66% of starting titre after thermal challenge at +37° C. for 1 week, this represents less than a 0.2 LOG loss.

Example 15

| Materials | | |
|---|---|---|
| Chemical | Supplier | ProductCode Lot No. |
| Dulbecco's phosphate buffered saline | Sigma | D8662 RNBB4780 |
| Polyethyleneimine | Sigma | 482595 05329KH |
| Raffinose | Sigma | R0250 050M0053 |
| Sucrose | Sigma | 161P137904 SZB90120 |
| Tween 20 | Sigma | 087K0197 |
| Skimmed milk powder | Marvel | |
| TMB chromogen | Invitrogen | SB02 72764382A |
| Sulphuric acid | Sigma | 25,8105 S55134-258 |
| Biological | Supplier | Product Code |
| Bivalent F(ab')2 | AbDSerotec | AbD09357.4 |
| Antigen - IgG2b kappa | AbDSerotec | PRP05 |
| Goat anti human HRP | AbDSerotec | STAR12P |
| Rabbit anti mouse HRP | AbDSerotec | STAR13B |
| Normal mouse serum | Sigma | M5905 |
| Other | Manufacturer | Product Code |
| 2 ml Eppendorf tubes | VWR | 16466-058 |
| ELISA immunoplates | NUNC | 439454 |
| Equipment | Manufacturer | Equipment No. |
| Forma 900 series −80° C. freezer | Thermofisher | EQP#015 |
| ATL-84-1 Atlion Balance | Acculab | EQP#088 |
| +56° C. Incubator | Binder | EQP#010 |
| Med Line +4° C. fridge | Liebherr | EQP#019 |
| +40° C. incubator | Binder | EQP#009 |
| Synergy HT Microplate reader | Biotek | EQP#027 |

Methods

The bivalent F(ab')2 was thermally challenged in the presence of various concentrations of excipients and assayed at different points. An ELISA assay was used to assess the residual F(ab')2 activity—this was used to measure the extent of damage sustained.

Preparation of and Thermal Challenge of Bivalent F(ab')2 in a Liquid Setting with Excipients Bivalent F(ab')2 in PBS, was removed from storage at −80° C. and allowed to thaw at room temperature. To determine the protective properties of the excipients in a liquid setting, 900 μl of each formulation with an antibody concentration of 4 μg/ml was made up—this quantity is sufficient to assay three separate timepoints. See Table 13 for details of each formulation.

TABLE 13 details of excipient formulations

| Abbreviation | Description | Suc | Raff | PEI |
|---|---|---|---|---|
| -SR/-P (x2) | no Suc/Raff/PEI, PBS only | — | — | — |
| LoSR/-P | Low [Suc/Raff], no PEI, in PBS | 0.1M | 0.01M | — |
| HiSR/-P | High [Suc/Raff], no PEI, in PBS | 1M | 0.1M | — |
| LoSR/LoP | Low [Suc/Raff], low [PEI], in PBS | 0.1M | 0.01M | 1.67 nM |
| LoSR/MedP | Low [Suc/Raff], medium [PEI], in PBS | 0.1M | 0.01M | 16.67 nM |
| LoSR/HiP | Low [Suc/Raff], high [PEI], in PBS | 0.1M | 0.01M | 166.67 nM |
| HiSR/LoP | High [Suc/Raff], low [PEI], in PBS | 1M | 0.1M | 1.67 nM |
| HiSR/MedP | High [Suc/Raff], medium [PEI], in PBS | 1M | 0.1M | 16.67 nM |
| HiSR/HiP | High [Suc/Raff], high [PEI], in PBS | 1M | 0.1M | 166.67 nM |

Two vials of the -SR/-P (control) formulation were set up—one was stored at +4° C. (as a positive control—no damage expected) and the second was placed at +56° C. with the other formulations (as a negative control; this formulation was not expected to remain stable and retain activity after 24 hours at an elevated temperature).

Assay of Bivalent F(ab')2 Activity

The activity of the Bivalent F(ab')2 was assayed by ELISA. Antigen (Rat IgG2b-kappa) diluted to 0.5 μg/ml in PBS was coated 100 μl/well in row A to G of a 96-well plate, as well as two extra wells in row H for the +4° C. control conditions. Normal mouse serum at a 1:400,000 dilution was also added to two wells of row H as a positive control. These controls were used to normalise data later. Plates were incubated for 18 hours at +4° C. then washed three times with PBS containing 0.05% Tween 20 (wash buffer).

Plates were dried by blotting onto a paper towel. This method of blotting was used in every wash step. Plates were blocked for 1.5 hours with PBS containing 5% skimmed milk powder and 0.05% Tween 20. Plates were washed three times with wash buffer before adding the samples.

After incubation at thermal challenge (or +4° C. for control vial), the F(ab')2 formulations were removed from incubator/fridge and 250 μl was removed from each. This was diluted 1:2 with wash buffer. Each diluted sample was added to the plate in duplicate and was diluted 2-fold down the plate (final concentrations ranging from 2 μg/ml to 0.0625 μg/ml). A condition with no bivalent F(ab')2 was also included to measure the background signal. The plates were incubated at room temperature for 1.5 hours after which time the plates were washed five times with wash buffer.

A goat anti-human HRP conjugated antibody was diluted 1:5000 in wash buffer and 100 μl added to all the wells containing bivalent F(ab')2. Rabbit anti-mouse HRP conjugate was diluted 1:1000 in wash buffer and 100 μl added to the wells containing the normal mouse serum control. The plates were incubated at room temperature for 1.5 hours then washed five times with wash buffer.

100 μl of TMB stabilised chromogen was added to each well and was allowed to react for 10 minutes at room temperature, after which time 100 μl 200 mM sulphuric acid was added to stop the reaction. The plates were read at 450 nm using Synergy HT Microplate reader.

Statistical Analysis

The average and standard deviation was taken for each duplicate and the data points plotted as a line graph or as a bar graph at a designated F(ab')2 concentration.

Results

Figure 39:
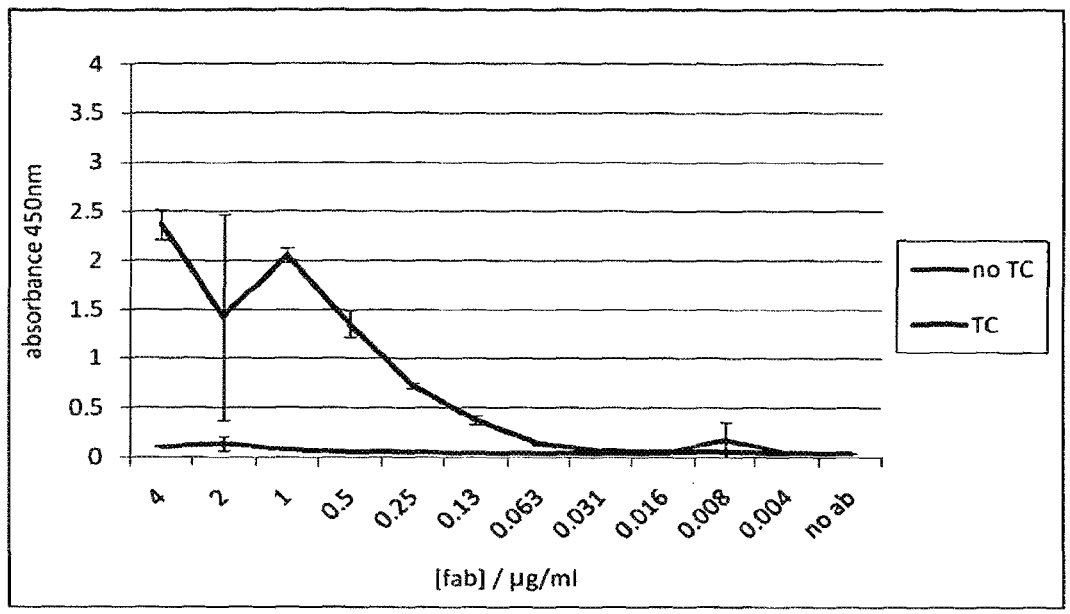
FIG. 39 shows the stability of F(ab')2 after storage at +56° C. for 24 hours.

Activity of Bivalent F(ab')2 Fragments after Thermal Treatment at +56° C. for 24 Hours In a preliminary study, stock F(ab')2 (as supplied by AbD Serotec—concentration 0.73 mg/ml) was stored at +56° C. to assess initial stability at elevated temperatures. The antibody was found to be extremely heat labile with little activity remaining after 24 hours at 56° C., providing an excellent starting point for testing the ability of the excipients to stabilise this antibody (FIG. 39).

Figure 40:
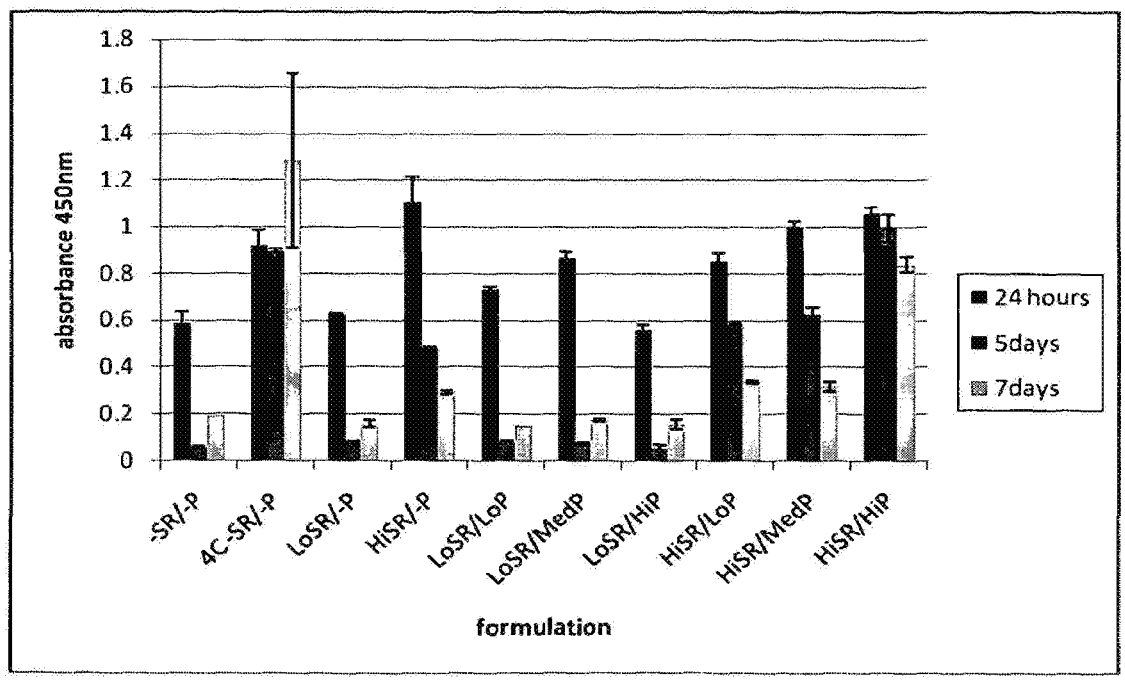
FIG. 40 shows the residual F(ab')2 activity (at 2 µg·ml) remaining in Example 15 at 24 hours, 5 days and 7 days following thermal challenge at +56° C.

Activity of Bivalent F(ab')2 Fragments after Thermal Treatment at +56° C. with and without Excipients The bivalent F(ab')2 was thermally challenged in the presence of various concentrations of the excipients and assayed at different points (see FIG. 40). After 24 hours storage at +56° C. most samples maintained the majority of their F(ab')2 activity (when compared to the control sample stored a +4° C.), however after 5 days samples formulated with low or no sugar, the residual F(ab')2 activity dropped to between 21% and 33% when compared to the activity remaining after 24 hours. Samples which contain high sugar concentration retained at least 44% activity after 5 days storage at +56° C. —this was increased to 63% to 94% with the addition of PEI.

The final timepoint was taken at 7 days thermal challenge at +56° C. The control sample had not lost any activity, as expected. The samples which were formulated with low or no sugar had lost the majority of their F(ab')2 activity. Samples which contained high sugar concentration maintained at least 27% of the 24 hour sample, this was increased to 79% when 10 μg/ml of PEI was added.

Conclusion

Samples stored at +4° C. for seven days do not sustain any loss in F(ab')2 activity, as expected. Samples which contain low sugar concentration, with or without PEI, lose the majority of F(ab')2 activity after 5 days at +56° C. The most protective formulations contained high sugar concentration, and the addition of 10 μg/ml PEI significantly increases the protection. After 5 days TC, all low sugar concentration samples lost the majority of F(ab')2 activity, whereas those which contained high sugar concentration and PEI still maintained a significant level of F(ab')2 activity.

Example 16

| Materials | | | |
|---|---|---|---|
| Chemical | Supplier | Product Code | Lot No. |
| Dulbecco's phosphate buffered saline | Sigma | D8662 | RNBB4780 |
| Dimethyl glycine | Sigma | D1156 | 077K1856 |
| Raffinose | Sigma | R0250 | 050M0053 |
| Sucrose | Sigma | 16104 | SZB90120 |
| Tween 20 | Sigma | P1379 | 087K0197 |

-continued

| Materials | | | |
|---|---|---|---|
| Chemical | Supplier | Product Code | Lot No. |
| Skimmed milk powder | Marvel | — | — |
| TMB chromogen | Invitrogen | SB02 | 72764382A |
| Sulphuric acid | Sigma | 25,8105 | S55134-258 |
| Biological | Supplier | | Product Code |
| Bivalent F(ab')$_2$ | AbDSerotec | | AbD09357.4 |
| Antigen - IgG2b kappa | AbDSerotec | | PRP05 |
| Goat anti human HRP | AbDSerotec | | STAR12P |
| Rabbit anti mouse HRP | AbDSerotec | | STAR13B |
| Normal mouse serum | Sigma | | M5905 |
| Other | Manufacturer | | Product Code |
| 2 ml eppendorf tubes | VWR | | 16466-058 |
| ELISA immunoplates | NUNC | | 439454 |
| Equipment | Manufacturer | | Equipment No. |
| Forma 900 series −80° C. freezer | Thermofisher | | EQP#015 |
| ATL-84-1 Atlion Balance | Acculab | | EQP#088 |
| +56° C. Incubator | Binder | | EQP#010 |
| MedLine +4° C. fridge | Liebherr | | EQP#019 |
| +40° C. incubator | Binder | | EQP#009 |
| Synergy HT Microplate reader | Biotek | | EQP#027 |

Methods
Design of Study

The bivalent F(ab')2 was thermally challenged in the presence of various concentrations of the excipients and assayed at different points. An ELISA assay was used to assess the residual F(ab')2 activity—this was used to measure the extent of damage sustained.

Preparation of and Thermal Challenge of Bivalent F(ab')2 in a Liquid Setting with Excipients Bivalent F(ab')2 in PBS, was removed from storage at −80° C. and allowed to thaw at room temperature. To determine the protective properties of the excipients in a liquid setting, 1050 µl of each formulation with an antibody concentration of 4 µg/ml was made up—this quantity is sufficient to assay four separate timepoints. See Table 14 for details of each formulation.

TABLE 14 details of excipient formulations

| Abbreviation | Description | Suc | Raff | DMG |
|---|---|---|---|---|
| -SR/-D (x2) | no Suc/Raff/DMG, PBS only | — | — | — |
| LoSR/-D | Low [Suc/Raff], no DMG, in PBS | 0.1M | 0.01M | — |
| HiSR/-D | High [Suc/Raff], no DMG, in PBS | 1M | 0.1M | — |
| LoSR/LoD | Low [Suc/Raff], low [DMG], in PBS | 0.1M | 0.01M | 0.3M |
| LoSR/MedD | Low [Suc/Raff], medium [DMG], in PBS | 0.1M | 0.01M | 0.7M |
| LoSR/HiD | Low [Suc/Raff], high [DMG], in PBS | 0.1M | 0.01M | 1M |
| HiSR/LoD | High [Suc/Raff], low [DMG], in PBS | 1M | 0.1M | 0.3M |
| HiSR/MedD | High [Suc/Raff], medium [DMG], in PBS | 1M | 0.1M | 0.7M |
| HiSR/HiD | High [Suc/Raff], high [DMG], in PBS | 1M | 0.1M | 1M |

Two vials of the -SR/-D (control) formulation were set up—one was stored at +4° C. (as a positive control—no damage expected) and the second was placed at +40° C. with the other formulations (as a negative control; this formulation was not expected to remain stable after 24 hours at an elevated temperature). After 24 hours, the thermally challenged samples were placed at +56° C. to accelerate damage.

Assay of Bivalent F(ab')2 Activity

The activity of the Bivalent F(ab')2 was assayed as set out in Example 15.

Statistical Analysis

The average and standard deviation was taken for each duplicate and the data points plotted as a line graph or as a bar graph at a designated F(ab')2 concentration.

Results

Figure 41:
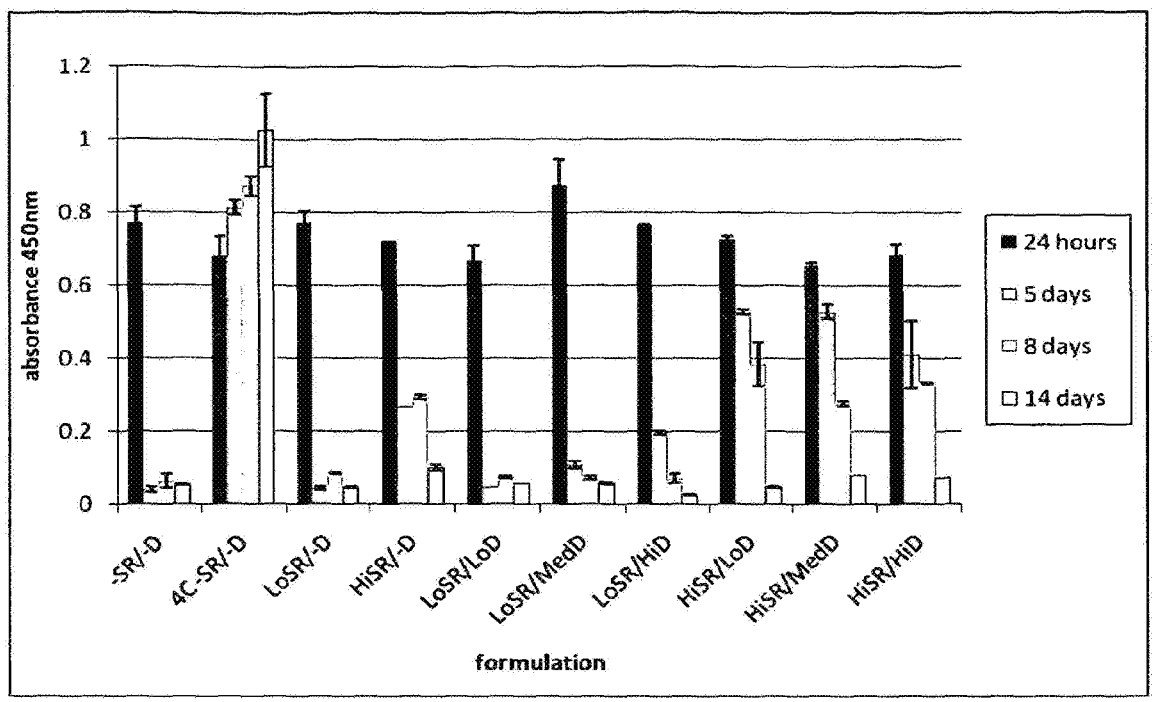
FIG. 41 shows the residual F(ab')2 activity (at 0.5 µg·ml) remaining at various time points in Example 16 after 14 days thermal challenge; 1 day at +40° C. and 13 days at +56° C.

Activity of Bivalent F(ab')2 Fragments after Thermal Treatment with and without Excipients The results are shown in FIG. 41. After 24 hours of storage at +40° C. there is no apparent damage to the F(ab')2 compared to the control condition stored at +4° C. After thermal challenge at +56° C. for a further 4 days, the activity of the unprotected F(ab')2 dropped to 5% of the activity after 24 hours. The samples which contained a low concentration of sugars retained between 6% (no DMG) and 26% (high DMG) of the activity remaining after 24 hours. Samples which contained high sugars retained at least 37% of activity remaining after 24 hours, and this was increased to 60%-81% with the addition on DMG.

The final timepoint was taken at 14 days post thermal challenge (24 hours at +40° C. then 13 days at +56° C.). Every thermally challenged sample had lost the majority of its activity (with between 3% and 14% activity remaining), indicating that the excipients were not sufficient to fully protect F(ab')2 under these harsh degradation conditions at +56° C. for 14 days.

Conclusion

Samples stored at +4° C. for two weeks did not sustain any loss in F(ab')2 activity, as expected. Samples which contain low sugar concentration, with or without DMG, lost the majority of F(ab')2 activity after 5 days at +56° C. The most protective formulations contained DMG and high sugar concentrations.

Example 17

| Materials | | | |
|---|---|---|---|
| | Supplier | Product Code | Lot No. |
| Betaine (aka TMG) | Sigma | B2629 | 069K1514 |
| Dimethyl glycine | Sigma | D1156 | 077K1856 |
| Raffinose | Sigma | R0250 | 050M0053 |
| Sucrose | Sigma | 16104 | SZB90120 |
| Water | Sigma | W3500 | 8M0411 |
| PBS | Sigma | D8662 | RNBB4780 |
| Equipment | | | |
| Component | Manufacturer/Model | | Equipment No. |
| HPLC Separations Module | Waters Alliance e2695 | | EQP021 |
| HPLC PDA Detector | Waters 2998 PDA | | EQP022 |
| HPLC Column Thermal Chamber | Waters Column Oven | | EQP023 |
| HPLC Separations Column | TOSOH TSK-Gel G3000SWxl | | EQP102 |
| HPLC Guard Colulmn | TOSOH TSK-Gel SWxl | | EQP103 |
| 56° C. Incubator | Binder | | EQP010 |

Methods

Sample Preparation

The positive and negative control samples were prepared as 167 μg FAb in PBS (positive control was prepared fresh immediately prior to HPLC analysis). Sucrose-Raffinose mix-only control was prepared as 167 μs FAb in PBS with 0.15 M Sucrose and 0.015M Raffinose. Test samples were prepared as 167 μg FAb in PBS with 0.15 M Sucrose and 0.015M Raffinose with one of the following 0.1M (low) or 1.0M (high) DMG or TMG. All samples except the positive control were subjected to a 130 h heat challenge at 56° C. This resulted in a total of seven samples.

After the challenge, the positive control was prepared as described above before all samples were subjected to centrifugation at 16.3 k·g for 5 minutes at room temperature to remove any insoluble matter. Supernatants were carefully decanted so as not to disturb any pellets. Decanted supernatants were then used for HPLC analysis as described below.

HPLC

Sample Loading and Injection

The sample chamber was kept at 5° C. and the column at 25° C. Samples were injected twice as blocks. GFC molecular weight standards (BioRAD #151-1901) were run before and after each block to ensure correct functioning of the HPLC setup.

25 μL injection volumes were used with a flow rate of 1.0 mL/min in 0.1M $Na_2SO_4$ & 0.1M $Na_2HPO_4$ buffer equilibrated to pH 6.8 at 25° C. with concentrated sulphuric acid solution. A run time of 18 minutes was used for both samples and standards.

Data Processing

Elution profiles were followed at 214 nm. An automated integration method was used for all samples using the Empower 2 software package. The specification of the HPLC method is as follows. The traditional (first derivative) Integration Algorithm was used with a Peal Width of 30.00 and a Threshold of 50.000. Both Minimum Area and Minimum Height were set to zero. An Inhibit Integration event was set between zero and 7.5 minutes elution time. At 7.5 minutes elution time, a Force Baseline by Peak event was used. No other events were invoked.

Four peaks were established: (1) Aggregate at 8.670±0.434 minutes; (2) Monomer at 10.100±0.465 minutes; (3) Shoulder at 10.574±0.529 minutes and (4) Fragment at 11.200±0.500. All further peaks, i.e. peaks eluting after 12 minutes, were discarded. Peak picking parameters for all peaks were as follows: Peak Match was set to Closest; Y Value was set to Area; Fit was set to Linear and Weighting was disabled.

Purity and Monomer Retention Parameters

The peak areas derived from the processing described above were used to generate Purity and Monomer Retention parameters for each condition. Purity was defined as monomer peak area divided by total peak within each sample. Monomer Retention was defined as monomer peak area divided by the monomer peak area in the positive control (non-heat-challenged) sample.

Results

Sample and Standards Traces

Figure 42:
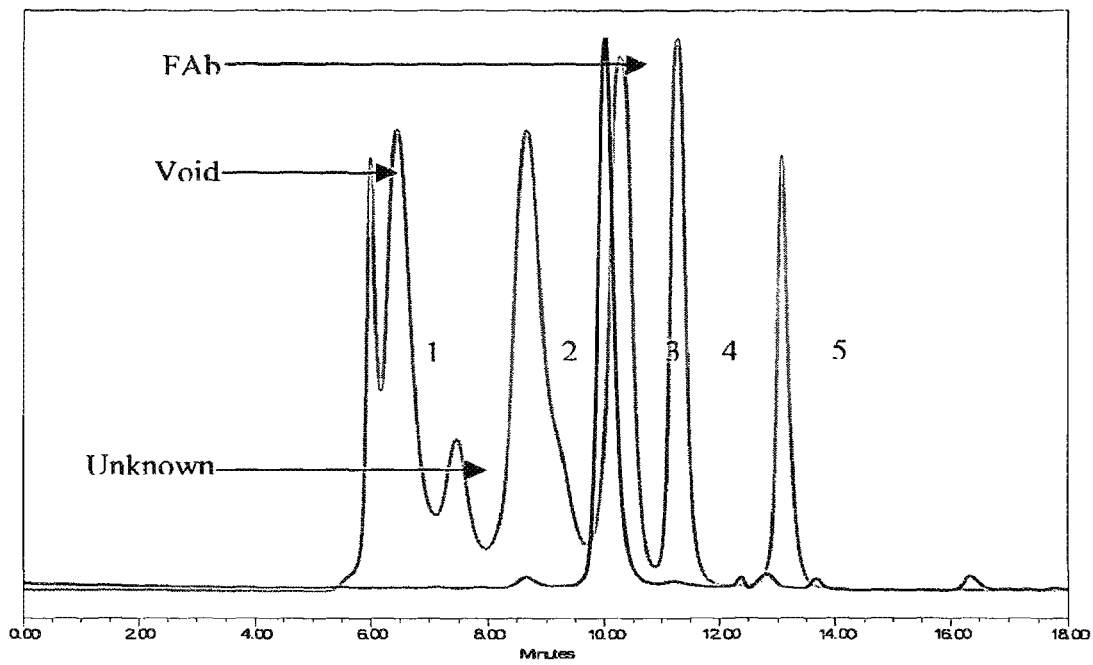
FIG. 42 shows a y-normalised superposition of the standards trace acquired in Example 17 before sample injection and the first injection of the untouched positive control sample. The FAb elutes just before the third weight marker, giving it an estimated hydrodynamic weight of more than 44 kDa. This value is consistent with a monovalent FAb.

FIG. 42 a Y-normalised HPLC overlay trace of molecular weight standards (BioRAD, 151-1901; light grey) and untouched monovalent FAb (dark grey). The molecular weights standards feature an initial void peak (as labelled), five standard components (numbered 1 to 5) and an unknown peak (as labelled). The identity and sizes of the five standards components are as follows: (1) bovine thyroglobin—670 kDa; (2) bovine-globulin—158 kDa; (3) chicken ovalbumin—44 kDa; (4) horse myoglobin—17 kDa and (5) vitamin $B_{12}$ 1.35 kDa. As can be seen, the FAb peak elutes prior to the third standard indicating an hydrodynamic-equivalent size of greater than 44 kDa as would be expected for a monovalent FAb. Thus, the FAb elutes just before the third weight marker, giving it an estimated hydrodynamic weight of more than 44 kDa. This value is consistent with a monovalent FAb.

Figure 43:
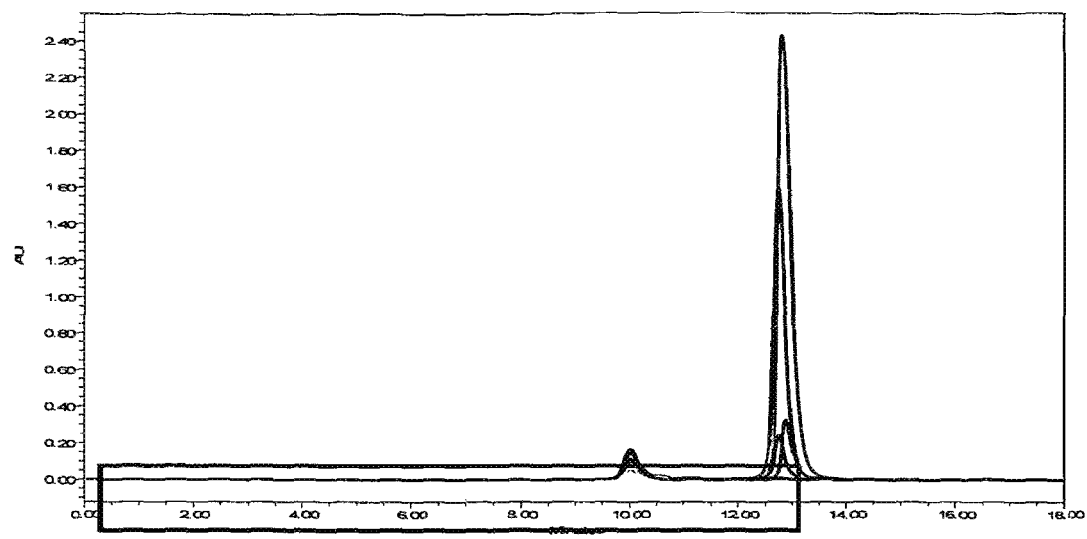
FIGS. 43 to 45 show a superpositions of seven HPLC traces in Example 17 corresponding to the first injection of each condition. The large peaks at 13 minutes (labelled b) in FIG. 44 are due to excipient whilst the smaller peak at ten minutes (labelled a) is due to the FAb. A black rectangle highlights the area that is expanded and shown in FIG. 45.
Figure 44:
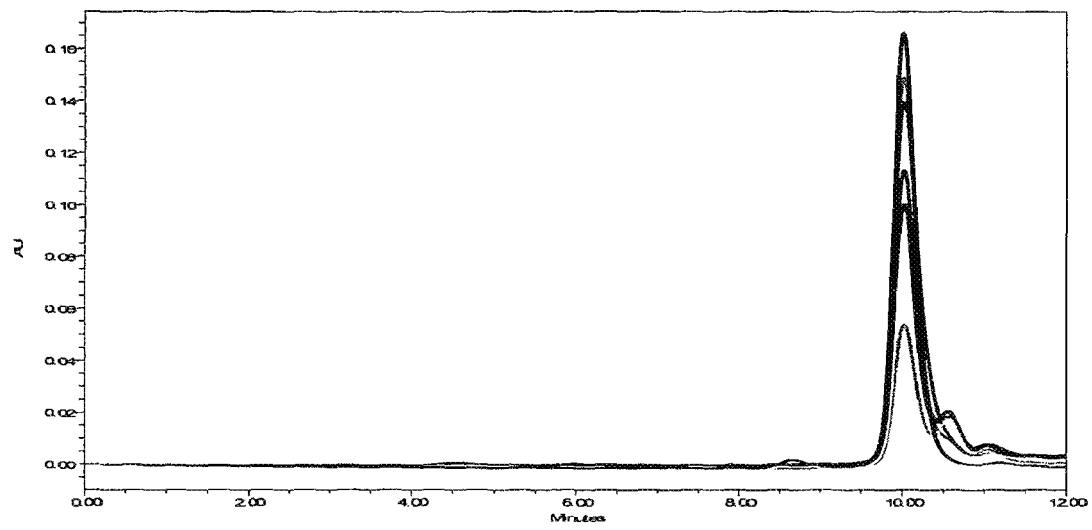
Figure 45:
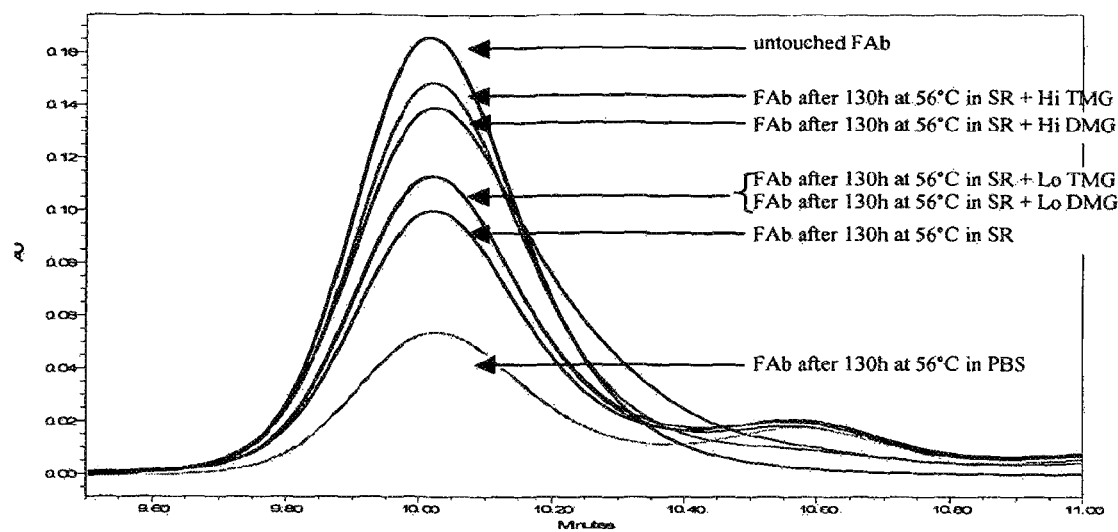

FIGS. 43 to 45 all show a superposition of seven HPLC traces corresponding to the first injection of each condition. The large peaks at 13 minutes (labelled b) in FIG. 43 are due to excipient whilst the smaller peak at ten minutes (labelled a) is due to the FAb. A black rectangle highlights the area that is expanded and shown in FIG. 44.

FIG. 43 is a full scale HPLC trace of all seven conditions described in the main text. The small peak at 10 minutes (labelled a) is the Antibody fragment (FAb) peak. The large peak at 13 minutes (labelled b) is due to excipient. The dark box highlights the area expanded and shown in FIG. 44.

FIG. 44 shows the same superposition of the first injection of all seven conditions as shown in FIG. 43. However, the trace in FIG. 44 is terminated after 12 minutes. FIG. 44 highlights the FAb peak and indicates that some but not all the samples contain a shoulder peak at the tail end of the monomer peak. The FAb peak itself is highlighted in annotated form in FIG. 45

FIG. 44 shows HPLC trace of all seven conditions described in the main text. The trace is shown up to 12 minutes (the Antibody Fragment (FAb) peak occurs at 10 minutes). Distinctions in the magnitude and shouldering of the peak can be seen between the seven conditions. The FAb peak is highlighted in FIG. 45.

FIG. 45 is an annotated HPLC trace of all seven conditions described above. The trace is shown zoomed to highlight the Antibody Fragment (FAb) peak at 10 minutes. The identity of the each of the seven conditions is annotated on the Figure. SR is sugar mix (0.15 M Sucrose and 0.015 M Raffinose), DMG is Dimethyl Glycine and TMG is Trimethyl Glycine. The suffix 'lo' refers to a low concentration of the excipient and is 0.1 M. The suffix 'hi' refers to a high concentration of the excipient and is 1.0 M.

FIG. 45 indicates that of all the heat-challenged samples, those with 1.0 M DMG or TMG (plus SR mix) produce a trace closest to the positive control (non-heat-challenged) sample. At the other end, FAb heat-challenged in PBS alone suffers the greatest loss and also experiences a marked increase in the shoulder peak. The next lowest monomer height occurred with FAb challenged in SR alone. SR mix plus 0.1 M of either DMG or TMG provided medial protection that was better than SR mix alone but inferior to SR mix plus either 1.0M DMG (better) or 1.0M TMG (best).

In summary, maximum monomer peak height with concomitant minimum shoulder peak presence proceeded in this order:

untouched>SR+HiTMG>SR+HiDMG>SR+LoTMG=SR+LoDMG>SR>PBS

This qualitative visual inspection mirrors the quantitative integration results discussed below.

Integrated Sample Traces

The HPLC processing method described above was used to integrate all seven HPLC traces as shown in FIG. 46 (only traces for one of two injections of each sample is shown). Arrows highlight both the baseline to baseline (triangle) and inflection change (diamond) peak events shown on the x-axis along the baseline.

Figure 46A:
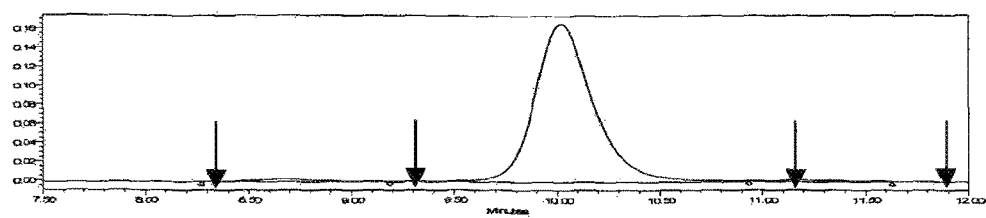
FIG. 46A-G shows a series of integrated HPLC traces in Example 17 as follows.

FIG. 46A: Condition 1: Untouched FAb (positive control).

Figure 46B:
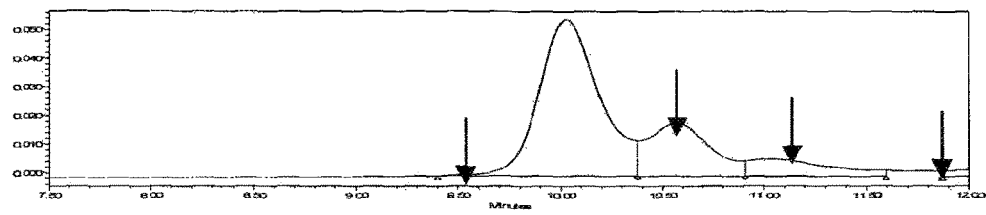

FIG. 46B: Condition 2: FAb after 130 h at 56° C. in PBS (negative control).

Figure 46C:
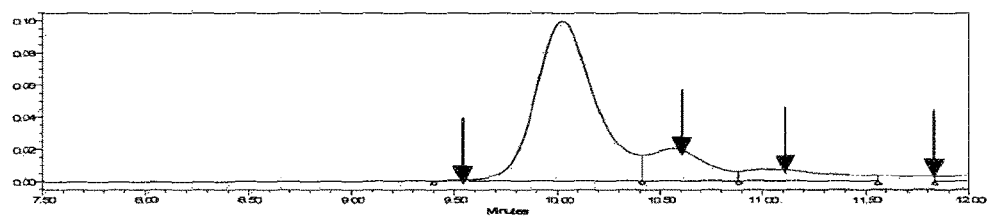

FIG. 46C: Condition 3: FAb after 130 h at 56° C. in SR mix.

Figure 46D:
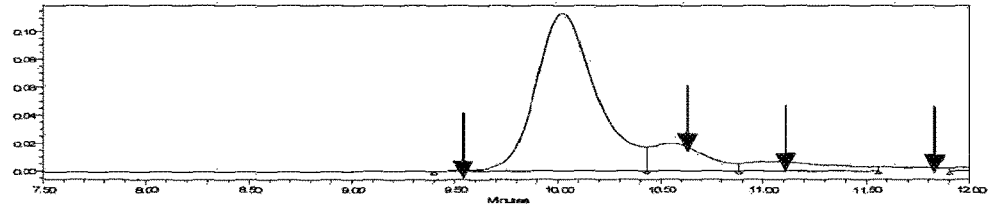

FIG. 46D: Condition 4: FAb after 130 h at 56° C. in SR mix & low (0.1M) DMG.

Figure 46E:
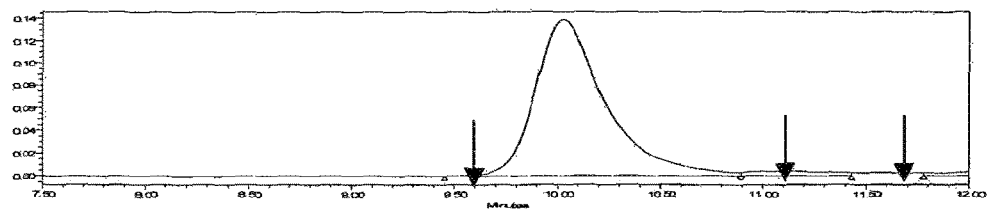

FIG. 46E: Condition 5: FAb after 130 h at 56° C. in SR mix and high (1.0M) DMG.

Figure 46F:
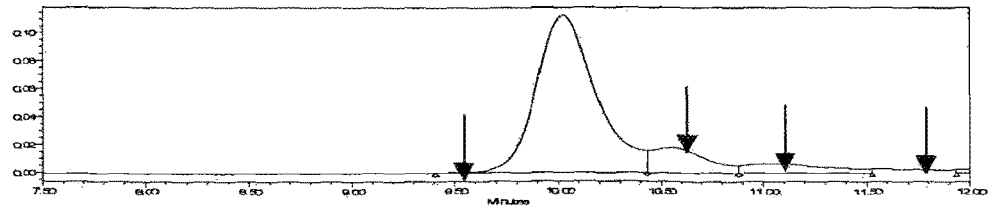

FIG. 46F: Condition 6: FAb after 130 h at 56° C. in SR mix & low (0.1M) TMG.

Figure 46G:
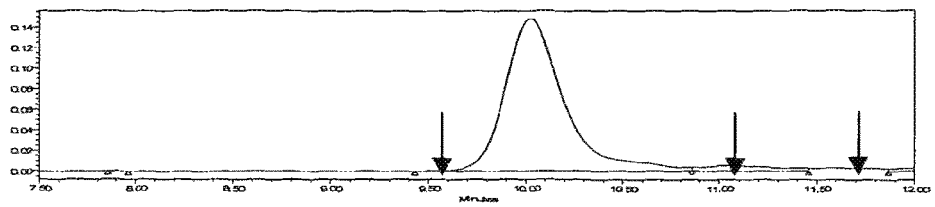

FIG. 46G: Condition 7: FAb after 130 h at 56° C. in SR mix & high (1.0M) TMG.

Summary

Figure 47:
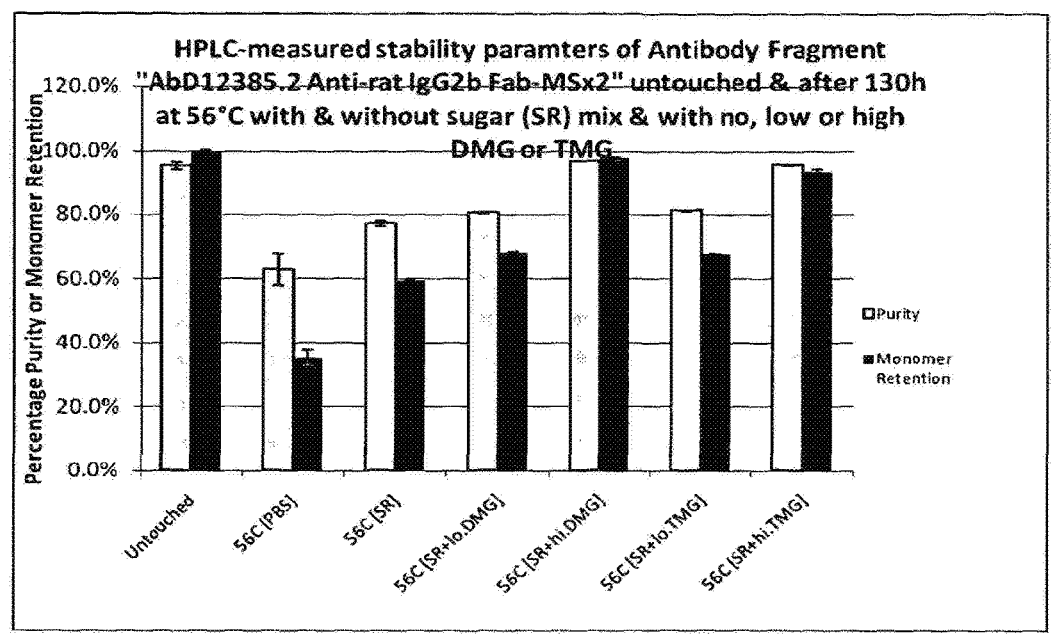
FIG. 47 summarises purity (light grey) and monomer retention (dark grey) parameters for each of the seven conditions in Example 17. All samples were at 167 µg/mL. Untouched was the non-heat-challenged positive control. All other samples were heat-challenged at 56° C. (hence 56 C) for 130 h. Square brackets indicate sample composition.

FIG. 47 summarises purity (light grey) and monomer retention (dark grey) parameters for each of the seven conditions described above. All samples were at 167 μg/mL. Untouched was the non-heat-challenged positive control. All other samples were heat-challenged at 56° C. for 130 hours. Square brackets indicate sample composition:

PBS—FAb diluted with PBS;
SR—FAb with 0.15M Sucrose and 0.015M Raffinose;
SR+lo.DMG—FAb with 0.15M Sucrose and 0.015M Raffinose and 0.1M DMG;
SR+hi.DMG—FAb with 0.15M Sucrose and 0.015M Raffinose and 1.0M DMG;
SR+lo.TMG—FAb with 0.15M Sucrose and 0.015M Raffinose and 0.1M TMG;
SR+hi.TMG—FAb with 0.15M Sucrose and 0.015M Raffinose and 1.0M TMG.

Error bars are ±1 standard deviation from repeat injections onto the HPLC column.

Conclusion

FIG. 47 quantitatively mirrors the qualitative ordinal results from FIG. 45 and indicates that simply diluting the FAb into PBS prior to HC at 56° C. for 130 h causes a one third loss in purity and a two thirds loss in monomer content. These losses are somewhat reduced by incubation with SR mix (0.15M Sucrose and 0.015M Raffinose). Losses are further minimised by incubation with SR mix and 0.1M DMG or TMG.

However, the most pertinent results are that both purity and monomer losses can essentially be completely avoided by addition of SR mix and 1.0M of either DMG or TMG to the FAb solution prior to heat-challenge.

Example 18—Maintenance of Diagnostic Samples in a Liquid Setting

Methods

Human blood samples were diluted with an equal volume of: a) PBS; b) 0.7M DMG; or c) 0.7M DMG/0.1M sucrose. After storage at 25° C. for 30 minutes, 5 μl of blood sample was mixed with 250 ul of Guava© Viacount© reagent in an eppendorf tube. The mixture was incubated at room temperature for 5 minutes. After incubation, the viability of the white cell fraction was assessed using the Guava PCA© cell analyser.

RESULTS AND CONCLUSIONS

The results from the Guava PCA© cell analyzer showed that the DMG and DMG/sucrose excipient mixtures tested exhibited no adverse effects on the white cell viability in the blood sample over the time period tested and at the concentration tested. Thus it can be inferred that such excipients will have minimal impact upon the integrity of less sensitive diagnostic specimens (eg. urine, sputum) and would enhance the stability of virus or protein present in the fluid.

The invention claimed is:

1. A method for the preparation of a ready-to-use, storage-stable aqueous solution which is provided in a sealed container and which contains live viral particles, which method comprises:

(a) providing a solution comprising:

water or physiological saline, which is optionally buffered with a physiologically acceptable buffer;

live viral particles from Adenoviridae, Orthomyxoviridae, Paramyxoviridae, Parvoviridae, Picornaviridae, Poxviridae, Flaviviridae or Herpesviridae;

an excipient which is an N,N-di($C_{1-6}$ alkyl)-glycine or N,N,N-tri($C_{1-6}$ alkyl)-glycine, or a physiologically acceptable salt or ester thereof;

a sulfone compound of formula (IIC):

(IIc)

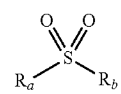

wherein $R_a$ and $R_b$ independently represent $C_{1-6}$ alkyl; and optionally one or more sugars; and (b) sealing the aqueous solution of step (a) in a container, thereby preparing said ready-to-use, storage stable aqueous solution containing live viral particles.

2. The method according to claim 1, in which the viral particles are from an adenovirus, vaccinia virus, influenza virus or measles virus.

3. The method according to claim 1, in which the excipient is N,N-dimethylglycine or N,N,N-trimethylglycine, or a physiologically acceptable salt or ester thereof.

4. The method according to claim 3, in which the excipient is N,N-dimethylglycine or a physiologically acceptable salt or ester thereof.

5. The method according to claim 1, in which the solution comprises sucrose or mannitol.

6. The method according to claim 5, in which the solution comprises sucrose and raffinose.

7. The method according to claim 1, in which the sulfone compound of formula (IIC) is methylsulfonylmethane.

8. The method according to claim 1, in which the solution is isotonic.

9. The method according to claim 1, in which the solution is provided in a sealed container under nitrogen.

10. The method according to claim 1, in which the sealed contained is a sealed vial, ampoule, syringe, cartridge, flexible bag or glass bottle.

11. The method according to claim 1, in which the solution is passed through a sterilising filter in step (a).

12. A ready-to-use, storage-stable aqueous solution containing live viral particles from Adenoviridae, Orthomyxoviridae, Paramyxoviridae, Parvoviridae, Picornaviridae, Poxviridae, Flaviviridae or Herpesviridae which is provided in a sealed container, said live viral particle containing aqueous solution being obtainable by a method as defined in claim 1.

13. The aqueous solution according to claim 12, in which the solution of the method comprises sucrose or mannitol.

14. The aqueous solution according to claim 12, in which the solution of the method comprises a sulfone of formula (IIC) which is methylsulfonylmethane.

15. The method according to claim 1, in which the solution comprises sucrose.

16. The method according to claim 1, in which the solution comprises mannitol.

17. The method according to claim 1, in which the solution comprises sucrose and mannitol.

* * * * *